US012399126B2

(12) United States Patent
Bergholt et al.

(10) Patent No.: US 12,399,126 B2
(45) Date of Patent: Aug. 26, 2025

(54) RAMAN SPECTROSCOPY METHOD AND SYSTEM

(71) Applicants: King's College London, London (GB); Trustees of Boston University, Boston, MA (US)

(72) Inventors: Mads S. Bergholt, London (GB); Michael B. Albro, Boston, MA (US); Brian D. Snyder, Boston, MA (US); Magnus Jensen, London (GB)

(73) Assignees: King's College London, London (GB); Trustees of Boston University, Boston, MA (US)

( * ) Notice: Subject to any disclaimer, the term of this patent is extended or adjusted under 35 U.S.C. 154(b) by 280 days.

(21) Appl. No.: 17/796,412

(22) PCT Filed: Jan. 28, 2021

(86) PCT No.: PCT/US2021/015485
§ 371 (c)(1),
(2) Date: Jul. 29, 2022

(87) PCT Pub. No.: WO2021/154991
PCT Pub. Date: Aug. 5, 2021

(65) Prior Publication Data
US 2023/0341330 A1 Oct. 26, 2023

Related U.S. Application Data

(60) Provisional application No. 62/967,203, filed on Jan. 29, 2020.

(51) Int. Cl.
*G01N 21/65* (2006.01)
*G01N 33/483* (2006.01)

(52) U.S. Cl.
CPC ......... *G01N 21/65* (2013.01); *G01N 33/4833* (2013.01)

(58) Field of Classification Search
CPC ............... G01N 21/64; G01N 15/147; G01N 2035/00237; G01N 2035/00326;
(Continued)

(56) References Cited

U.S. PATENT DOCUMENTS 10,674,919 B2 * 6/2020 Banke ............... G01J 3/0216
2001/0052979 A1 12/2001 Treado et al.
(Continued)

FOREIGN PATENT DOCUMENTS

CA 2917308 A1 * 1/2014 ......... A61B 1/00165
CN 106124478 A * 11/2016
(Continued)

OTHER PUBLICATIONS

InPhotonics: Polarization Probe, retrieved Dec. 7, 2023 from https://www.inphotonics.com/probepolarization.htm.
(Continued)

*Primary Examiner* — Michael P Stafira
(74) *Attorney, Agent, or Firm* — Banner & Witcoff, Ltd.

(57) ABSTRACT

Methods and systems for obtaining biochemical and/or structural information relating to tissues using Raman spectroscopy. Polarised light is directed to tissue using a probe. The light is reflected from the tissue, producing Raman scattering. The Raman scattering is collected by the system and split into two polarised components. The two polarised components are simultaneously imaged using a spectrometer to produce two Raman spectra. The Raman spectra are then processed and analysed using a computer program to obtain biochemical and/or structural information relating to the tissue.

18 Claims, 30 Drawing Sheets

(58) Field of Classification Search
CPC .... G01N 35/08; G01N 21/65; G01N 21/4795; G01N 21/6445; G01N 21/6458; G01N 21/05; G01N 2021/0346; G01N 2201/024; G01N 27/3275; G01N 21/21; G01N 2021/653; G01N 2201/0675; G01N 21/6408; G01N 21/6486; G01N 2500/00; G01N 33/5008; G01N 33/542; G01N 15/1459; G01N 2015/1006; G01N 21/6428; G01N 1/38; G01N 2021/1787; G01N 2021/6471; G01N 21/49; G01N 2201/0638; G01N 33/58; G01N 21/55; G01N 33/5375; G01N 33/54313; G01N 33/54353; G01N 2021/6421; G01N 2021/6463; G01N 2035/00158; G01N 33/582; G01N 21/47; G01N 21/636; G01N 21/6456; G01N 21/19; G01N 21/4133; G01N 21/645; G01N 33/573; G01N 15/149; G01N 2021/216; G01N 2021/6441; G01N 2021/655; G01N 21/4738; G01N 21/8422; G01N 2201/129; G01N 33/5302; G01N 21/41; G01N 21/45; G01N 21/6402; G01N 21/6452; G01N 2201/0221; G01N 2201/0633; G01N 2201/068; G01N 2201/08; G01N 33/536; G01N 33/54386; G01N 2021/4792; G01N 2021/638; G01N 2021/6484; G01N 21/23; G01N 21/31; G01N 33/4833; G01N 2021/178; G01N 21/88; G01N 21/8806; G01N 2201/061; G01N 2201/063; G01N 2333/19; G01N 2021/1704; G01N 2021/1765; G01N 2021/4714; G01N 2021/4733; G01N 2021/656; G01N 2021/8829; G01N 2021/8848; G01N 21/1702; G01N 21/1717; G01N 21/255; G01N 21/39; G01N 15/0205; G01N 15/0227; G01N 2021/1706; G01N 2021/213; G01N 2021/3137; G01N 2021/317; G01N 2021/3177; G01N 2021/3196; G01N 2021/4721; G01N 2021/4797; G01N 2021/6419; G01N 2021/8816; G01N 2021/8825; G01N 2021/8835; G01N 2021/8845; G01N 21/253; G01N 21/274; G01N 21/35; G01N 21/3504; G01N 21/3563; G01N 21/359; G01N 21/474; G01N 21/4788; G01N 21/53; G01N 21/554; G01N 21/648; G01N 21/76; G01N 21/7743; G01N 2201/0635; G01N 2201/0833; G01N 2201/0846; G01N 2201/10; G01N 2201/1248; G01N 2291/02475; G01N 29/2418; G01N 29/46; G01N 33/02; G01N 33/025; G01N 33/15; G01N 33/442; G01N 33/49; G01N 33/52; G01N 33/533; G01N 33/54306; G01N 33/54373; G01N 33/56983; G01N 33/6893; G01N 33/6896; G01N 33/94; G01N 33/9453; G01N 35/085

See application file for complete search history.

(56) References Cited

U.S. PATENT DOCUMENTS

| | | |
|---|---|---|
| 2005/0283058 A1 | 12/2005 | Choo-Smith et al. |
| 2008/0212180 A1* | 9/2008 | Zhang ............... G01J 3/02 359/491.01 |
| 2009/0002702 A1* | 1/2009 | Maier ............... A61B 5/7264 702/19 |
| 2013/0215422 A1* | 8/2013 | Kimura ............... G01J 3/44 356/301 |
| 2017/0284940 A1* | 10/2017 | Butte ............... G01J 3/0218 |
| 2019/0343394 A1 | 11/2019 | Sato |
| 2019/0383747 A1* | 12/2019 | He ............... G01N 21/658 |

FOREIGN PATENT DOCUMENTS

| | | | | |
|---|---|---|---|---|
| CN | 110207822 A | | 9/2019 | |
| WO | WO-2005009236 A1 | * | 2/2005 | ......... A61B 5/0059 |
| WO | WO-2009138738 A1 | * | 11/2009 | ......... A61B 5/0075 |
| WO | WO-2016003371 A1 | * | 1/2016 | ............. A61B 1/018 |
| WO | WO-2016075694 A1 | * | 5/2016 | ............... G01J 3/26 |
| WO | WO-2018085687 A1 | * | 5/2018 | ............. G01J 3/0218 |
| WO | WO-2018134980 A1 | * | 7/2018 | ......... A61B 5/0075 |
| WO | WO-2018213698 A1 | * | 11/2018 | ......... A61B 5/0075 |
| WO | WO-2019004944 A1 | * | 1/2019 | ......... A61B 10/0233 |
| WO | 2020011560 A1 | | 1/2020 | |
| WO | WO-2020000712 A1 | * | 1/2020 | ............. G01N 21/65 |

OTHER PUBLICATIONS

May 18, 2021—(WO) International Search Report and Written Opinion—PCT/US2020/015485.
Apr. 29, 2025—Ep Examination Report—App. No. 21707525.8.

* cited by examiner

RAMAN SPECTROSCOPY METHOD AND SYSTEM

CROSS-REFERENCE TO RELATED APPLICATIONS

This application is a U.S. National Stage application under 35 U.S.C. § 371 of International Application PCT/US2021/015485, filed Jan. 28, 2021, which claims the benefit of priority to U.S. Provisional Application No. 62/967,203, filed Jan. 29, 2020, and the present application claims the benefit of the filing date of each of these prior applications, both of which prior applications are hereby incorporated by reference in their entireties. This application claims priority to U.S. Provisional Application No. 62/967,203, filed on Jan. 29, 2020, whose contents are expressly incorporated herein by reference in its entirety.

TECHNICAL FIELD

Embodiments of the present invention described herein relate to methods and systems for obtaining structural and biochemical information of tissues by using Raman spectroscopy.

BACKGROUND TO THE INVENTION AND PRIOR ART

Osteoarthritis (OA) is a chronic, debilitating painful condition, characterized by the structural degeneration of articular cartilage, the load-bearing connective tissue that lines the ends of long bones. It is the most widespread cause of disability in adults; over 20% of the adult population of the US, or over 50 million individuals, are afflicted with the disease and its incidence is predicted to rise sharply over coming decades. Currently, no clinical therapy exists to halt the progression of the disease.

Articular cartilage degeneration during osteoarthritis (OA) occurs in stages. Early stage degeneration is marked by difficult-to-detect tissue changes: an initial loss of glycosaminoglycans (GAG) from the topmost cartilage layers and disorganization (alignment loss) of collagen at the articular surface (FIG. 1.1). This is followed by far more substantial physical erosion of the collagen matrix, until bone-on-bone contact is reached. Interestingly, the early stage of the disease, before substantial tissue erosion has occurred, represents a critical clinical window, when intervention strategies (e.g., drug therapies, physical therapy, lifestyle changes) may be most effective at reversing the onset of cartilage degeneration. However, the ability to diagnose early-stage OA remains a considerable clinical challenge; conventional imaging platforms (e.g., radiography, CT, MRI) are predominantly suited for diagnosing late stages of the disease due to lack of resolution and molecular specificity. For this reason, there is a great need to introduce novel biomolecular sensitive optical techniques for the in vivo early-stage diagnosis of OA.

The structure and composition of hyaline cartilage is optimized for its mechanical performance. It is comprised of a type-II collagen (COL) fibril network that affords structure and tensile strength, complemented by a negatively charged sulfated glycosaminoglycan (GAG) matrix that provides compressive properties and retains interstitial water. More than 90% of applied joint load is supported by pressurization of entrapped water (interstitial fluid load support), yielding the tissue's characteristic low frictional properties. Additionally, cartilage is inhomogeneous and structurally anisotropic, where the collagen configuration varies with depth (segregated into zones) and is optimized for the mechanical loading of each zone: superficial zone (SZ)—comprised of collagen arranged parallel to the articular surface and resists surface shear and improves gliding; transitional (middle) zone (MZ)—composed of mix-aligned collagen and GAGs responsible for generating interstitial fluid load support; deep radial zone (DZ)—collagen fibers perpendicular to the subchondral plate, anchors cartilage to subchondral bone. During OA, degradation of cartilage occurs in stages. Early on, GAG is depleted from the SZ with concomitant loss of superficial collagen fiber organization and alignment. Loss of GAG and COL alignment reduces fluid load support, transferring loads to the collagen matrix, and leading to cartilage erosion through the MZ and DZ, culminating in significant cartilage volume loss until bone-on-bone contact is reached.

As a major clinical challenge, changes in joint structure and function that account for OA morbidity and disability appear relatively late in the disease process. Currently, OA is diagnosed from clinical symptoms (pain, swelling, impaired function) and image-based assessments (radiographs and magnetic resonance imaging (MRI)) that are biased towards late-stage OA pathoanatomy (cartilage volume loss, bone marrow edema, subchondral bone thickening, cysts, and osteophytes) 10. The irreversible breakdown of cartilage occurs before clinical symptoms and radiographic signs are evident. Therefore, OA diagnosed at a late stage, after changes in tissue structure have transpired, restricts treatment options. The inability to identify mild or early cartilage damage, when therapeutic strategies will be most effective, remains a significant clinical obstacle.

Raman spectroscopy is an inelastic light scattering technique that offers an in vivo optical biopsy of tissues at the molecular level. Using fiber-optic probes, Raman spectra can be obtained from tissues in vivo (e.g., by the use of endoscopes). The Raman spectrum scales linearly with concentrations and therefore contains a wealth of quantitative information, allowing for the potential extraction of contents of key extracellular matrix (ECM) constituents in the tissue. We have major experience in Raman spectroscopy of cartilage as well as clinical translation of Raman technologies: At National University of Singapore (NUS), Dr Bergholt pioneered real-time "Raman endoscopy" for non-invasive in vivo "optical biopsy" in the gastrointestinal (GI) tract (Gastroenterology 2014: IF 20.877). This technique was applied in more than 800 patients over 5 years, lead to 3 patent applications that has recently been commercialised in form of a medical device for endoscopy (IMDX™, Endofotonics Pte Ltd). In turn, this work allowed expansion of this system as a platform technology to a plurality of organs including: oral cavity, nasopharynx, larynx, esophagus, gastric and colon in humans (J Raman spectroscopy, 2012; J Biomed Opt, 2012; J Biophotonics, 2016a). In contrast, there exists no clinical Raman technique for the diagnosis of OA.

In more detail, Raman spectroscopy is predicated on the inelastic scattering of photons. When monochromic laser light induces a change in molecular polarizability during vibrations, a small proportion of the incident photons (~1 in $10^8$) are scattered with a change in wavelength. The Raman scattered light indicates the vibrational modes of constituent molecules; the absorbed energy corresponds to specific Raman active vibrational modes that define a molecule's "fingerprint". Therefore, the Raman spectra of cartilage carry information about individual molecular vibrational bonds that correspond to specific biochemical building blocks (amides, sulfates, carboxylic acids, hydroxyls) of the constituents of hyaline cartilage (GAG, COL, H2O). Prior work demonstrates that Raman spectra of cartilage exhibit statistical changes in response to mechanical damage and OA. However, the implementation of Raman spectroscopy as a diagnostic tool for cartilage health has been impeded by: 1) lack of clinically compatible intra-articular, fiber-optic Raman needle probes for in vivo diagnostics, and 2) inability to extract specific and quantitative biochemical and structural metrics diagnostic of early stage OA. As a consequence, to date, a platform capable of achieving in vivo Raman diagnostics of early-OA has not been demonstrated.

US 2019/0343394 A1 describes a cartilage-tissue analysis device which uses univariate analysis (single peaks) to try to measure the major ECM constituents in articular cartilage (GAG and collagen) and cartilage thickness (via subchondral bone signal measures). However, this technique encounters limitations in terms of lack of molecular specificity and lack of structural assessments of the tissue. This lack of molecular specificity arises due to the overlap of vibrational bands within the spectra that cannot be easily deciphered as specific molecules in the complex tissue. Indeed, achieving identification (molecular specificity) is the grand challenge in diagnostic Raman spectroscopy. Our regression analysis offers far greater performance in terms of specificity and accuracy and offers the potential for quantification of a myriad of additional important components of the cartilage ECM (e.g. GAG subtypes [hyaluronan, chondroitin sulfate, keratin sulfate, heparin] and collagen subtypes [COL-I, COL-II, COL-X]). Further, our polarized Raman spectroscopy allows for assessment of the structure of articular cartilage through measures of the alignment of the collagen ECM.

SUMMARY OF THE INVENTION

Embodiments of the present invention address the above problem, by providing a new method for monitoring and diagnosing abnormal tissues. The Raman system comprises a polarised probe that may be compatible with arthroscopic portals or hypodermic needles. These needles can be inserted into joints and the Raman probe can be placed in contact with the articular cartilage surface. The invention includes a Raman system that offers simultaneous biochemical (collagen, GAGs and water, and molecular subtypes) and structural analysis (of structural components such as collagen). Methods and systems described herein may be used to obtain biochemical information alone or structural information alone. It is not essential that both biochemical and structural information are obtained simultaneously, although this is an advantageous embodiment. It is well accepted that diffusion of light scrambles the light polarisation in tissue. For this reason (and to target early superficial OA) we integrate a microlens at the tip of the Raman probe. Using a multiplexed acquisition principle, we can in parallel read out the Raman scattered light from two light polarisations and image them through a spectrometer onto a 2D CCD camera. This allows us to in one snapshot to obtain both biochemical and structural information for diagnosis. The data readout (two polarized Raman spectra) are analysed in real-time (<20 ms) using multivariate analysis in order to provide a quantitative assessment of collagen, GAG and water content as well as collagen structure factor. The probe further includes a lens at the probe tip, allowing for diagnostic targeting of different depths of the cartilage surface: e.g. targeting the cartilage surface where early-stage OA is most prominent or deeper tissue regions, where later stage degeneration manifests.

Assessing both biochemical quantification of GAG, collagen, and water in the cartilage ECM, as well as the structural characterization of the alignment of the collagen matrix is imperative for early diagnosis of osteoarthritis. This system can serve as: 1) a valuable clinical and pre-clinical research tool to examine the efficacy of novel OA therapeutics, and 2) in the future, an outpatient-based real-time diagnostic platform to guide early OA treatment courses. The invention can further achieve widespread use in a host of biomedical applications, such as diagnostics of cancer and fibrosis.

A thin, fiber-optic Raman spectroscopy probe is directed intra-articularly, via a hypodermic-needle-cannula, to "optically biopsy" cartilage at specific anatomic sites under image guidance. We first establish the potential of Raman arthroscopy to diagnose pathognomonic features of cartilage degeneration in early stage OA through parametric analysis of a series of ex vivo model systems: 1) Raman quantification of GAG content in enzymatically depleted bovine cartilage and aging human cartilage explants, 2) Raman quantification of zonal collagen network organization in mechanically abraded bovine cartilage explants, 3) Raman measurements of cartilage thickness. We finally perform an in vivo Raman arthroscopy assessment of the composition of an ovine femoral condyle, demonstrating the clinical feasibility of Raman OA diagnostics.

In view of the above, from a first aspect, the present disclosure relates to a system for obtaining structural information relating to tissue. The system comprising: (i) a probe configured to direct polarised light to the tissue and collect Raman scattering; (ii) a lens mounted at a distal tip of the probe, wherein the lens is configured to focus the polarised light onto the tissue such that the polarised light is reflected from the tissue, producing Raman scattering which is collected by the probe; (iii) a beam splitter configured to split the Raman scattering into two polarised components; and (iv) a spectrometer configured to simultaneously and separately image the two polarised components to produce two Raman spectra.

Several advantages are obtained from embodiments according to the above described aspect. For example the design of the probe and spectrometer input coupling enables two polarisations to be measured simultaneously. This allows for rapid structural information (e.g. collagen alignment) measurement. The beam splitter may be located within the probe itself. The spectrometer may be configured to simultaneously and separately image the two polarised components onto a camera to produce two Raman spectra.

In some embodiments, the system further comprises: a processor; and a memory including computer program code. The memory and the computer program code configured to, with the processor, cause the processor to process and analyse the two produced Raman spectra to obtain structural information relating to the tissue. Analysis described herein may be performed by a machine learning program.

The computer program is able to almost instantly analyse each polarized Raman spectra. This enables the real-time capabilities of the methods and systems described herein. Real-time capabilities are described in more detail below. The computer program reads out the two spectra separately but simultaneously.

In some embodiments, the system simultaneously obtains biochemical and structural information relating to the tissue.

Using a multiplexed acquisition principle, the Raman scattered light from two light polarisations can be read out in parallel and imaged through a spectrometer onto a 2D CCD camera. This allows us to in one snapshot obtain both biochemical and structural information for diagnosis and/or monitoring of conditions.

In some embodiments, the processing and analysing of the two produced Raman spectra obtains biochemical information and structural information relating to the tissue.

In some embodiments, a first polarised component of the two polarised components is parallel to polarisation of the polarised light, and a second polarised component of the two polarised components is perpendicular to polarisation of the polarised light.

In some embodiments, the structural information is obtained by calculating a difference between the first and second polarised components and/or a ratio between the first and second polarised components and/or an anisotropy between the first and second components.

The difference between the first and second polarised components and/or the ratio between the first and second components and/or an anisotropy between the first and second components produces a collagen organisation spectrum. For example, the ratio may reveal differences in Raman spectra due to integrity of superficial zone (SZ) collagen.

The anisotropy between the first and second components may be defined as:

$$r = \frac{I_\parallel - I_\perp}{I_\parallel + 2I_\perp}$$

where $I_\parallel$ is the first, parallel component and $I_\perp$ is the second, perpendicular component.

In some embodiments, the structural information comprises a measure of structural alignment in the tissue.

This is advantageous as low structural alignment can indicate different conditions. For example, disorganised tissue structure is a symptom of cancerous tissue, and in OA, parallel alignment disappears. The structural information may be classified using machine learning to decide whether the tissue structure is aligned or not.

In some embodiments, the biochemical information is obtained by quantifying relative contributions of extracellular matrix (ECM) constituents of the produced Raman spectra.

In some embodiments, biochemical information is obtained by calculating a sum of the first and second polarised components.

Quantifying relative contributions of ECM constituents allows depletion of particular constituents to be identified. This can aid diagnosis and/or monitoring of conditions.

From a second aspect, the present disclosure relates to a system for obtaining biochemical information relating to tissue. The system comprises: (i) a probe configured to direct light to the tissue and collect Raman scattering; (ii) a lens mounted at a distal tip of the probe, wherein the lens is configured to focus the light onto the tissue such that the light is reflected from the tissue, producing Raman scattering which is collected by the probe; (iii) a spectrometer configured to image the Raman scattering to produce a Raman spectrum; (iv) a processor; and (v) a memory including computer program code. The memory and the computer program code configured to, with the processor, cause the processor to process and analyse the produced Raman spectrum to obtain biochemical information relating to the tissue, wherein the biochemical information is obtained by quantifying relative contributions of ECM constituents of the produced Raman spectrum.

As mentioned above, quantifying relative contributions of ECM constituents allows monitoring of changes to specific constituents in the tissue. This can aid diagnosis and/or monitoring of conditions. This can be done without polarised light, as the Raman spectrum used to obtain biochemical information in the first aspect is the sum of the two polarised components (i.e. unpolarised light). Therefore, in situations where only biochemical information is required, polarised light is not required. As such, it may be advantageous to have a system and method where structural information is not obtained.

In some embodiments, the quantifying of the relative contributions of ECM constituents of the produced Raman spectra comprises using regression coefficients derived from multivariate least-squares-regression analysis. This analysis may be performed by a machine learning program.

The Raman spectral contribution of GAG and water are characteristically "buried" under the much stronger COL signal, thereby obscuring assessment of tissue GAG and water content. By decomposing and isolating the relative contribution of the major cartilage ECM constituents (GAG, COL, and H$_2$O) to the Raman cartilage spectra using regression coefficients derived from the multivariate least-squares-regression analysis, biochemical information can be obtained relating to the content of the constituents.

In some embodiments, the least-squares-regression analysis comprises comparing the produced Raman spectra to reference Raman spectra of the ECM constituents.

$$Cartilage_{spectra} = GAG_{score}*(GAG_{REF}) + COL_{score}*(COL_{REF}) + H2O_{score}*(H2O_{REF})$$

where $GAG_{REF}$, $COL_{REF}$, and $H2O_{REF}$ are the component spectra of purified reference chemicals of each ECM constituent (i.e. "reference Raman spectra of the ECM constituents"). The $GAG_{score}$, $COL_{score}$, and $H_2O_{score}$ "scores" are the regression coefficients that reflect the contribution of the spectra of each constituent element to the cumulative Raman cartilage spectra, i.e. the biochemical information output which can be used to aid diagnosis of conditions and/or monitor conditions. The scores for each component are proportional to the amount of each component in the tissue.

In some embodiments, the ECM constituents comprise one or more of glycosaminoglycan, collagen, and/or water.

It is advantageous to measure glycosaminoglycan (GAG) content, as GAG loss is a hallmark of early-stage OA. This allows earlier diagnosis of OA, and therefore earlier and more successful treatment. However, the ECM constituents could be any constituent as long as the constituent has a strong enough spectra to be identified within the produced Raman spectra. This opens the door to a wide range of uses of the methods and systems described herein—from cancer diagnosis to fibrosis diagnosis, and from enamel analysis to brain surgery. For example, methods and systems described herein can be used to differentiate between different collagen subtypes (e.g. type-I, type-II, and type-X collagen) or glycosaminoglycan subtypes (e.g. hyaluronan, chondroitin sulfate, heparin, keratin sulfate).

In some embodiments, the biochemical and/or structural information is obtained in real-time.

Methods and systems described herein allow data readout and analysis in real-time (less than 20 ms). This allows near-instant information relating to a current position of the probe. This is very useful as the clinician can instantly see biochemical and/or structural information relating to the tissue where they are holding the probe.

In some embodiments, the tissue is a musculoskeletal connective tissue.

In some embodiments, the biochemical and/or structural information is used to identify tissue abnormalities.

Depletion of particular biochemical (i.e. biochemical information) in tissue can be used to identify tissue abnormalities. Disorganised structure (i.e. structural information) in tissue can be used to identify tissue abnormalities. Identifying these tissue abnormalities can be used to aid a diagnosis and/or monitoring of a condition.

In some embodiments, the tissue abnormalities are cancerous.

In some embodiments, the biochemical and/or structural information is used to diagnose connective tissue degenerative disorders, such as osteoarthritis and/or degenerative disc disease. The biochemical and/or structural information may also be used to monitor treatment response. For example, tissue response to drugs, therapies, surgical interventions, graft implantation (e.g. osteochondral allografts, engineered tissue constructs, and/or cell implantation (e.g. autologous cell implantation).

In some embodiments, the tissue is engineered tissue and the biochemical and/or structural information is used to measure growth and/or regeneration of the engineered tissue. The probe may be used to monitor tissue growth/regeneration/stability from surgical graft procedures, such as implantation of osteochondral allografts, engineered tissue constructs, or cell implantation (e.g. autologous cell implantation).

In some embodiments, a source of the light or polarised light is a laser.

In some embodiments, the probe comprises a needle, and the lens is mounted at a tip of the needle and configured to be in contact with the tissue.

The needle embodiment is advantageous for in vivo use as it can be inserted into joints and placed in contact with the articular cartilage surface.

In some embodiments, the lens is a ball lens, preferably a sapphire ball lens.

As described herein, it is well accepted in the art that diffusion of light scrambles the polarisation in tissue. Using a lens with a tight focus, e.g. a ball lens, overcomes the problem of preserving polarisation information of the tissue. Without tightly focused lens, polarisation information would not be retrievable. The ball lens also allows for targeting the cartilage surface, where early-stage OA is most prominent. The tight focus may have an optical depth of around 200-300 µm.

Different lenses can be used to ascertain information from different tissue depths. For example, if interested in biochemical information relating to deep tissue regions, a lens with a longer focal length may be used. If interested in superficial tissue regions, a lens with a shorter focal length may be used. However, for the purposes of using polarisation information, the focal length must be short to preserve this information. Therefore, structural information which relies on polarised spectra cannot be obtained for deep tissue, as the tissue scrambles the polarisation. Only biochemical information can be obtained for deep tissue.

In some embodiments, the probe comprises a long-distance focusing Raman probe.

In the long-distance focusing Raman probe embodiment, the method further comprises directing the polarised light to the tissue through a Raman transparent window, the tissue being maintained in a suitable environment (e.g. in a tissue culture plate).

This ex vivo embodiment achieves in situ Raman measurements on specimens while they are maintained in culture. The Raman plate reader can serve as a high-throughput, non-destructive platform to monitor the composition of musculoskeletal connective tissue explants (e.g. cartilage, meniscus, tendons, ligaments, intervertebral disk) or engineered tissues over time. This platform has outstanding utility for studying tissue behaviour in response to mechanochemical stimuli, mechanisms of pathologic tissue degeneration, and the efficacy of therapeutics to inhibit or reverse degeneration, and the development of engineered tissues.

From a third aspect, the present disclosure relates to a method for obtaining structural information relating to tissue. This method corresponds to the system of the first aspect.

As such, any embodiments and advantages described above in relation to the first aspect are equally applicable to this corresponding method. The method comprises: (i) directing polarised light to the tissue using a probe; (ii) focusing the polarised light onto the tissue using a lens, wherein the lens is mounted at a distal tip of the probe and focuses the polarised light onto the tissue such that the polarised light is reflected from the tissue, producing Raman scattering; (iii) collecting the Raman scattering using the probe; (iv) splitting the Raman scattering into two polarised components using a beam splitter; (v) simultaneously and separately imaging the two polarised components using a spectrometer to produce two Raman spectra; and (vi) processing and analysing the two produced Raman spectra using a computer program to obtain structural information relating to the tissue.

In some embodiments, the method simultaneously obtains biochemical and structural information relating to the tissue.

From a fourth aspect, the present disclosure relates to a method for obtaining biochemical information relating to tissue. This method corresponds to the system of the second aspect. As such, any embodiments and advantages described above in relation to the second aspect are equally applicable to this corresponding method. The method comprises: (i) directing light to the tissue using a probe; (ii) focusing the light onto the tissue using a lens, wherein the lens is mounted at a distal tip of the probe and focuses the light onto the tissue such that the light is reflected from the tissue, producing Raman scattering; (iii) collecting the Raman scattering using the probe; (iv) imaging the Raman scattering using a spectrometer to produce a Raman spectrum; (v) processing and analysing the produced Raman spectrum using a computer program to obtain biochemical information relating to the tissue, wherein the biochemical information is obtained by quantifying relative contributions of major cartilage ECM constituents of the produced Raman spectra.

From a fifth aspect, the present disclosure relates to a system for simultaneously obtaining biochemical and structural information relating to tissue. The system comprises: (i) a probe configured to direct polarised light to the tissue and collect Raman scattering; (ii) a lens mounted at a distal tip of the probe, wherein the lens is configured to focus the polarised light onto the tissue such that the polarised light is reflected from the tissue, producing Raman scattering which is collected by the probe; (iii) a beam splitter configured to split the Raman scattering into two polarised components; (iv) a spectrometer configured to simultaneously and separately image the two polarised components to produce two Raman spectra.

This aspect is advantageous as it provides the capability to do both conventional Raman (by summing the spectra for biochemical analysis) and polarized Raman (for structural analysis e.g., by division) all at the same time. The combination of: (a) the polarisation probe, (b) the capability to multiplex these two polarisations simultaneously producing two distinct Raman spectra, and (c) having the distal lens (with a very tight focus of around 200-300 μm) which is key to preserve polarisation from the surface is very advantageous. Further, this system has the capability to do this in real-time so we can offer biochemical and structural information in one go.

This aspect relates to the simultaneous capture of biochemical and structural information. As such, any embodiments and advantages described above in relation to the first (describes the system being used for structural information) and second (describes the system being used for biochemical information) aspects are equally applicable to this system.

Embodiments of the fifth aspect may further comprise a processor and a memory including computer program code. The memory and the computer program code configured to, with the processor, cause the processor to process and analyse the two produced Raman spectra to obtain biochemical information and structural information relating to the tissue.

From a sixth aspect, the present disclosure relates to a method for simultaneously obtaining biochemical and structural information relating to tissue. This method corresponds to the system of the fifth aspect. As such, any embodiments and advantages described above in relation to the first, second and fifth aspects are equally applicable to this corresponding method. The method comprises: (i) directing polarised light to the tissue using a probe; (ii) focusing the polarised light onto the tissue using a lens, wherein the lens is mounted at a distal tip of the probe and focuses the polarised light onto the tissue such that the polarised light is reflected from the tissue, producing Raman scattering; (iii) collecting the Raman scattering using the probe; (iv) splitting the Raman scattering into two polarised components using a beam splitter; (v) simultaneously and separately imaging the two polarised components using a spectrometer to produce two Raman spectra; and (vi) processing and analysing the two produced Raman spectra using a computer program to obtain biochemical information and structural information relating to the tissue.

Embodiments described above provide considerable advancements over the existing methodologies by diagnosing early stage OA (GAG loss and collagen disorganization) with a platform that is safe and minimally invasive. The systems and methods described herein may also be used to diagnose other conditions where biochemical and structural information allows identification of the condition. For example, cancerous tissue can be identified from structural information as cancer tissue is structurally disorganised. Additionally, the system is low cost (relative to conventional radiology equipment) and non-ionising, and thus will serve as the first biochemical-based diagnostic platform that can be performed in a clinician's office environment.

Conventional diagnostic techniques such as CT and MRI are only able to assess late stage OA after considerable cartilage erosion has occurred as disease modifying therapies are no longer viable. New diagnostic technologies, such as contrast enhanced MRI (dGEMRIC) have been shown to diagnose early-stage OA GAG loss, but encounter a host of limitations, including the use of potentially harmful contrast agents, a highly extended patient prep/imaging durations, and the need for large, highly expensive equipment infrastructure. Our proposed polarized confocal needle probe provides considerable advancements over the existing methodologies by diagnosing early stage OA (GAG loss and collagen disorganization) with a platform that is safe and minimally invasive.

No needle-based Raman methods exist for diagnosing OA. This invention offers the following concrete advantages over other Raman techniques in general:

1) The invention offers real-time biochemical information (GAG/collagen content) and structural information (collagen alignment) of tissues in vivo.
2) The design of the probe and spectrometer input coupling enables two polarisations to be measured simultaneously. This allows for rapid collagen alignment measurement.
3) The needle probe with integrated lens focuses the light tightly so that polarisation information of tissue can be maintained.
4) Lens-interface further allows for measurement of GAG loss from cartilage surface, a hallmark of early-stage OA.

BRIEF DESCRIPTION OF THE DRAWINGS

Embodiments of the invention will now be further described by way of example only and with reference to the accompanying drawings, wherein.

DESCRIPTION OF THE EMBODIMENTS

Overview

Figure 1A:
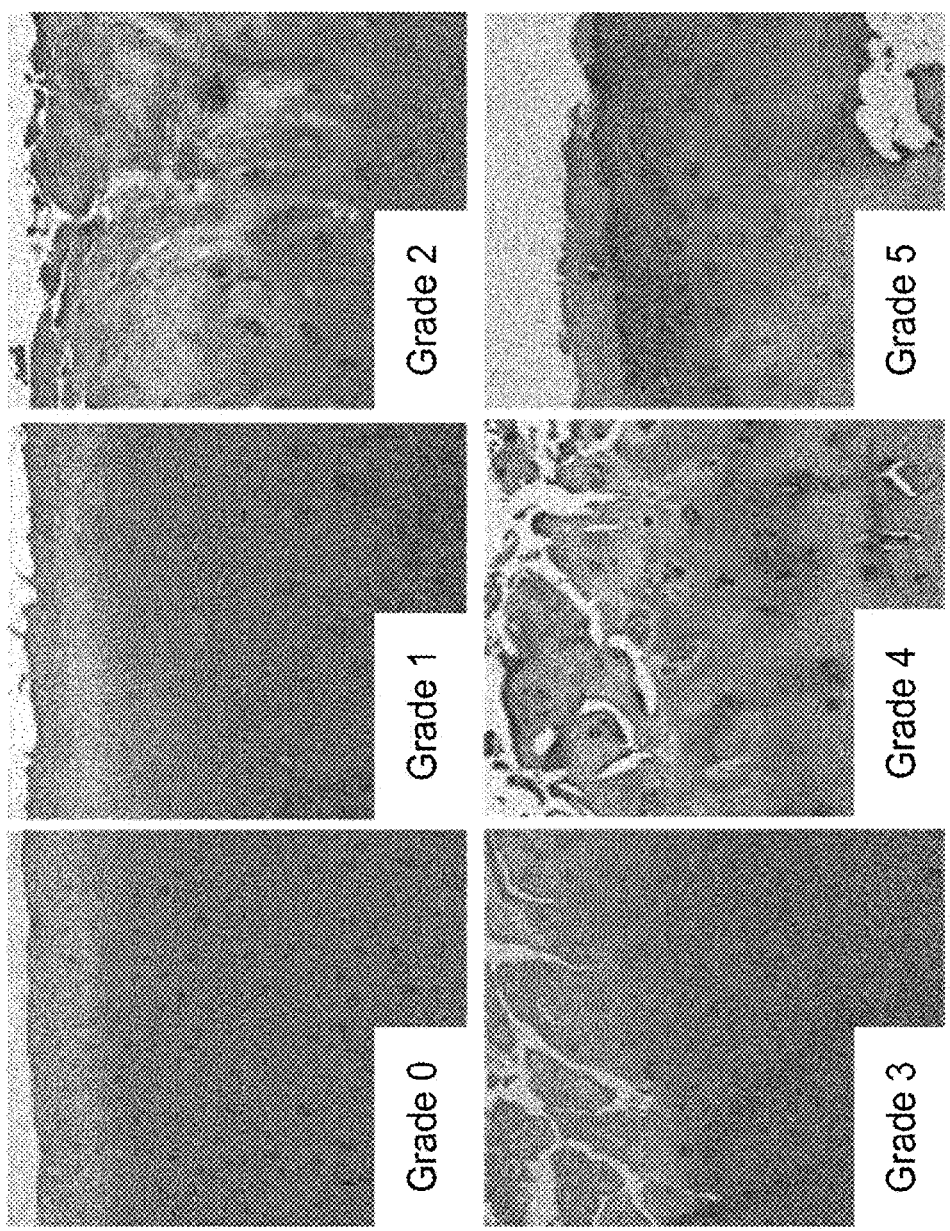
FIG. 1A shows OARSI grades of safo/fast green stained condyle cartilage from TKA (1). Early stage OA (grade 1-2) is marked by loss of GAG and increased COL disorganization at the cartilage surface. Late-stage OA (grade 3-5) is marked by progressive COL erosion.
Figure 1B:
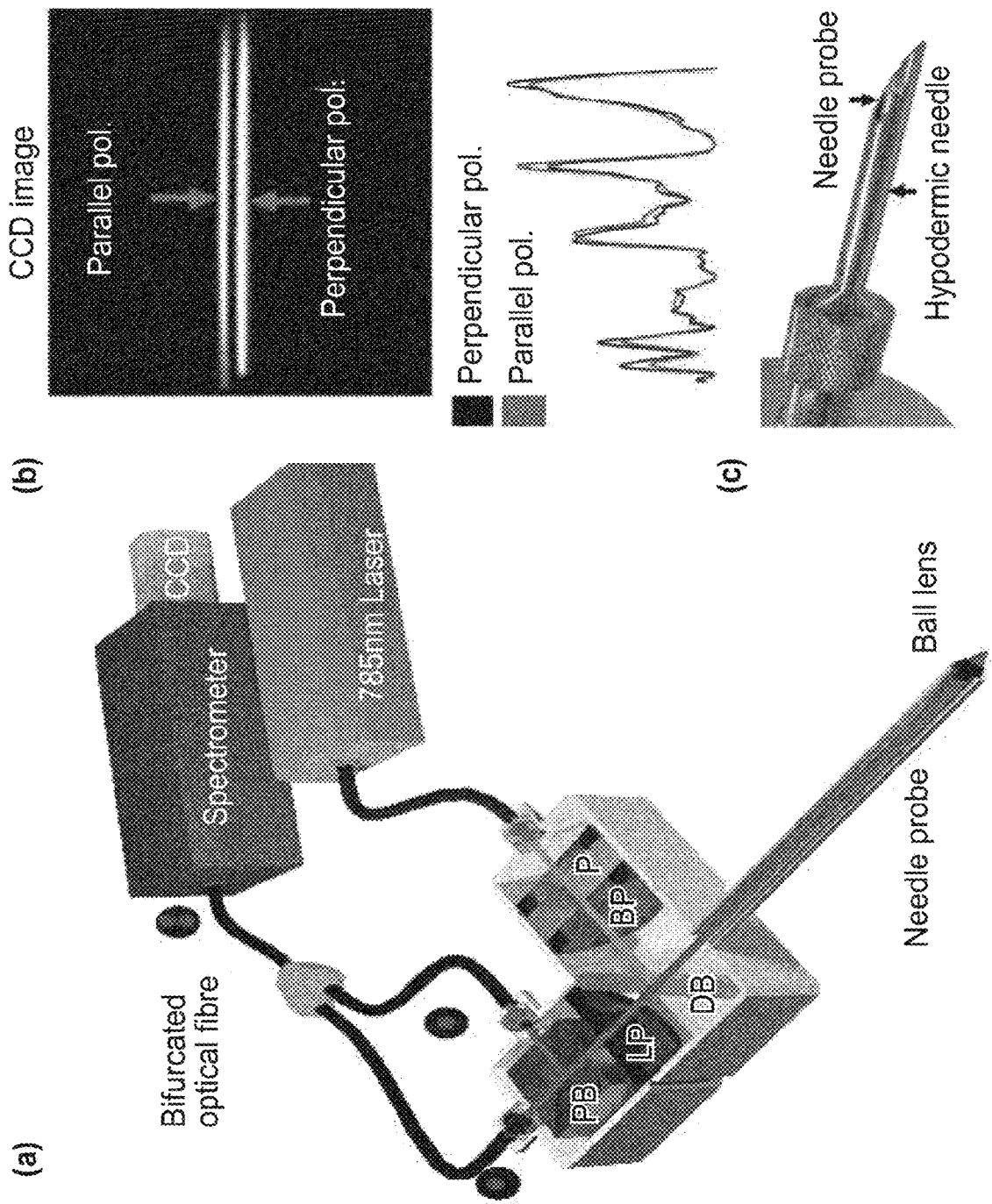
FIG. 1B shows schematics of the developed multiplexed polarized needle probe for biochemical and structural analysis of tissues. PB: polarisation beam splitter, LP: long pass filter, DB: Dichroic beam splitter, BP: Band pass filter, P: linear polarizer.
Figure 1C:
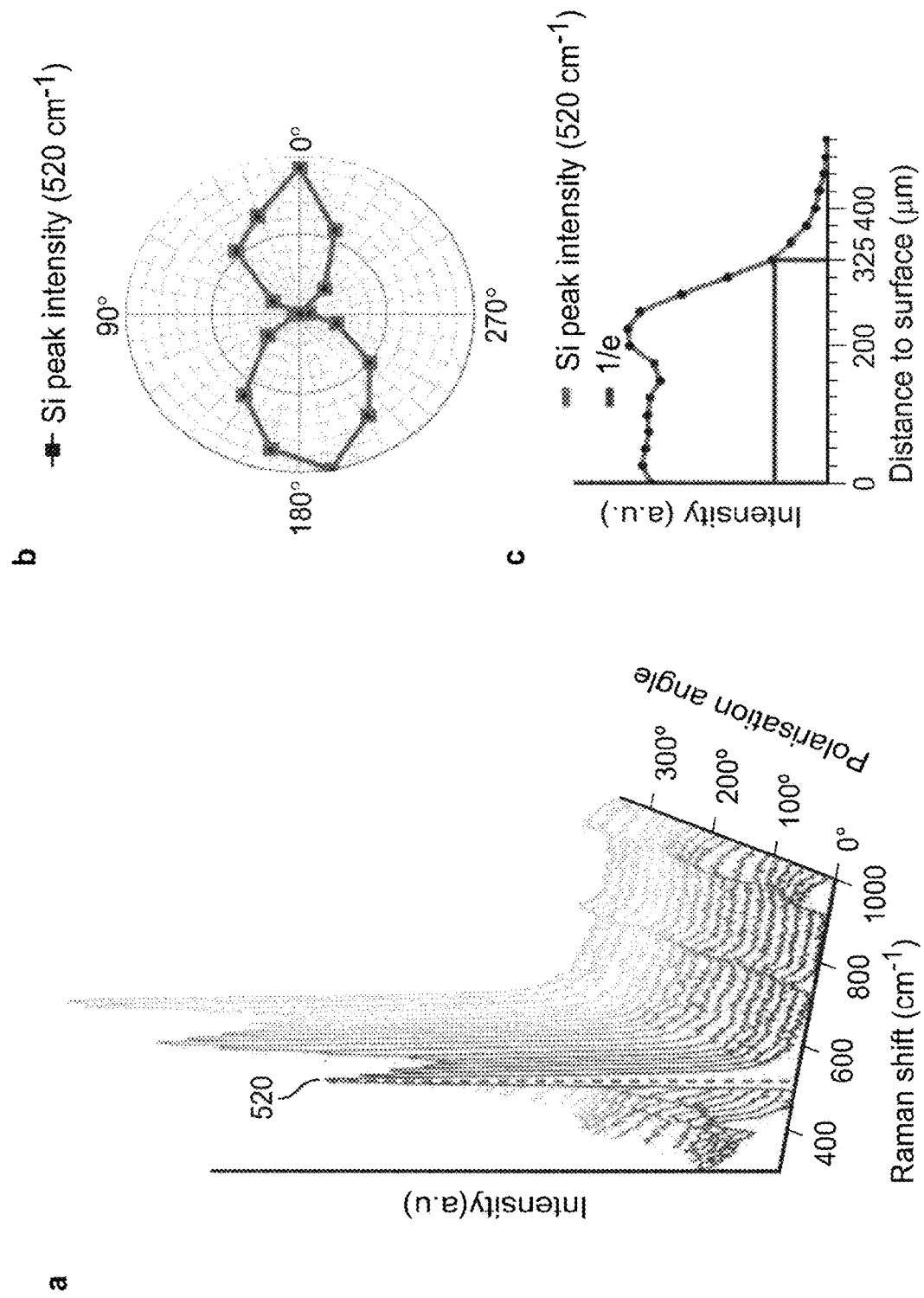
FIG. 1C shows (a) Raman spectra of silicon under full rotation of the incident laser polarisation, (b) Polar diagram of the 520 cm-1 peak intensity under a full polarisation rotation.
Figure 1D:
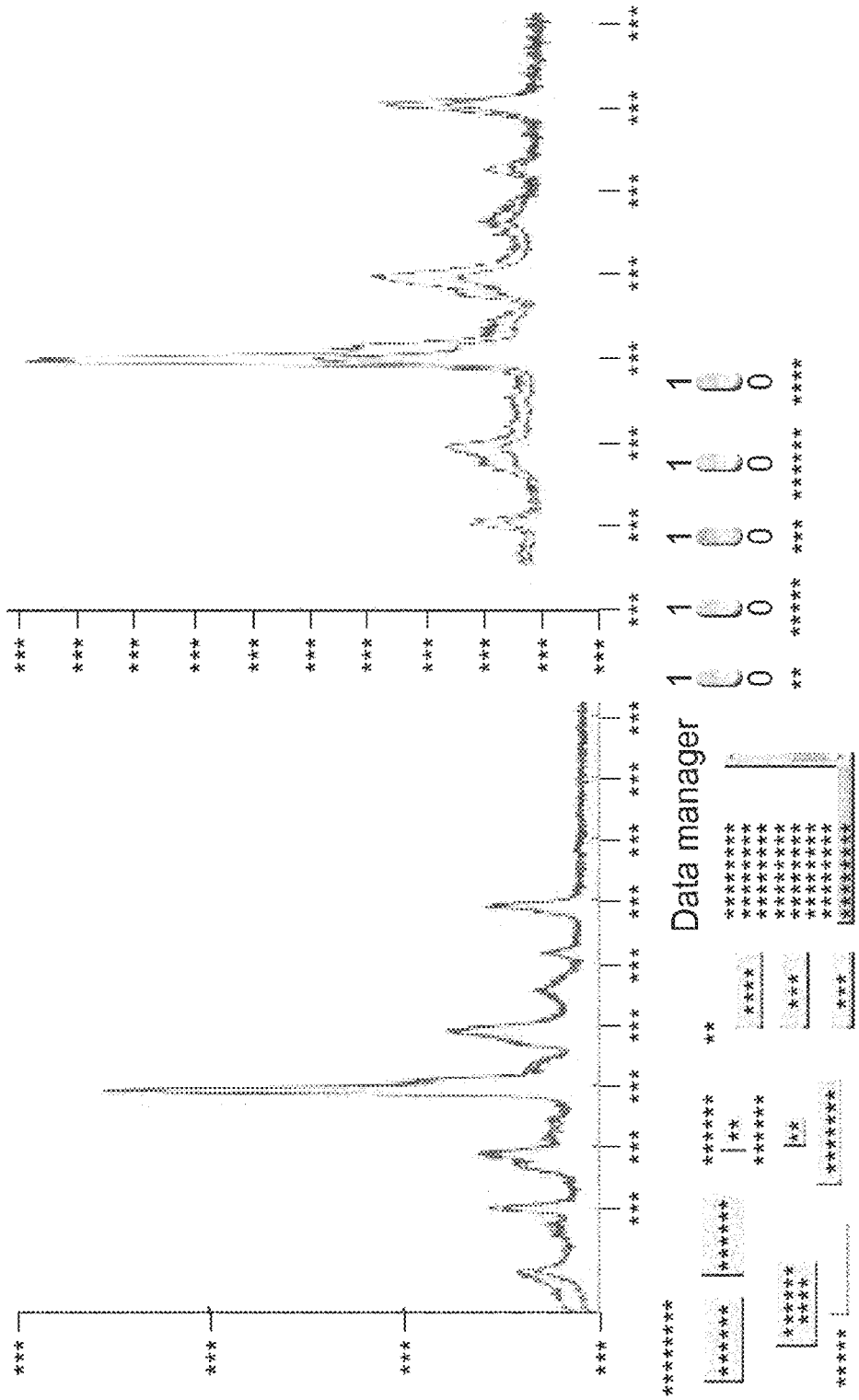
FIG. 1D shows a screenshot of the developed software that implements multiplexed polarized Raman acquisition (perpendicular+parallel) and analysis.
Figure 1E:
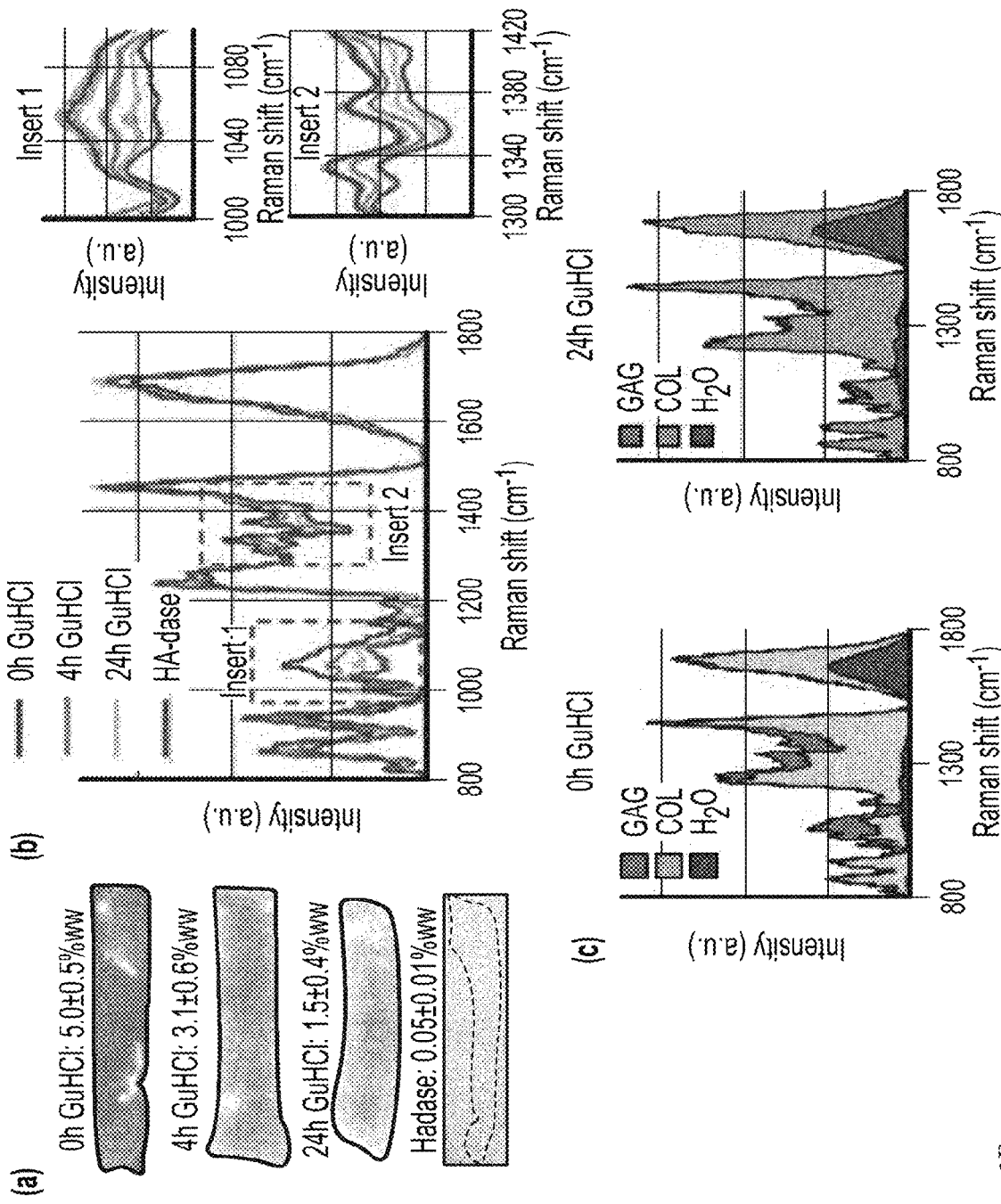
FIG. 1E shows a Raman probe GAG Measurements: (A) GuHCl/HAdase-induced GAG depletion of cartilage explants (saf-0 histology and DMMB measurements). (B) GuHCl/HAdase-induced decrease of Raman intensity in 1000-1100 $cm^{-1}$ and 1300-1450 $cm^{-1}$ wavenumber ranges (mean±SD). (C) Linear regression decomposition of cartilage Raman spectra into component spectra and concentrations of GAG, COL, and $H_2O$. GAG contribution to Raman spectra is attenuated after 24 h GuHCl treatment. (D) Extracted scores of GAG, COL, $H_2O$ for each treatment. (E) Correlation between Raman GAG score and (F) Raman GAG:H2O score ratio to assay-measured GAG content. (F) GAG score correlation to explant $E_y$.
Figure 1E:
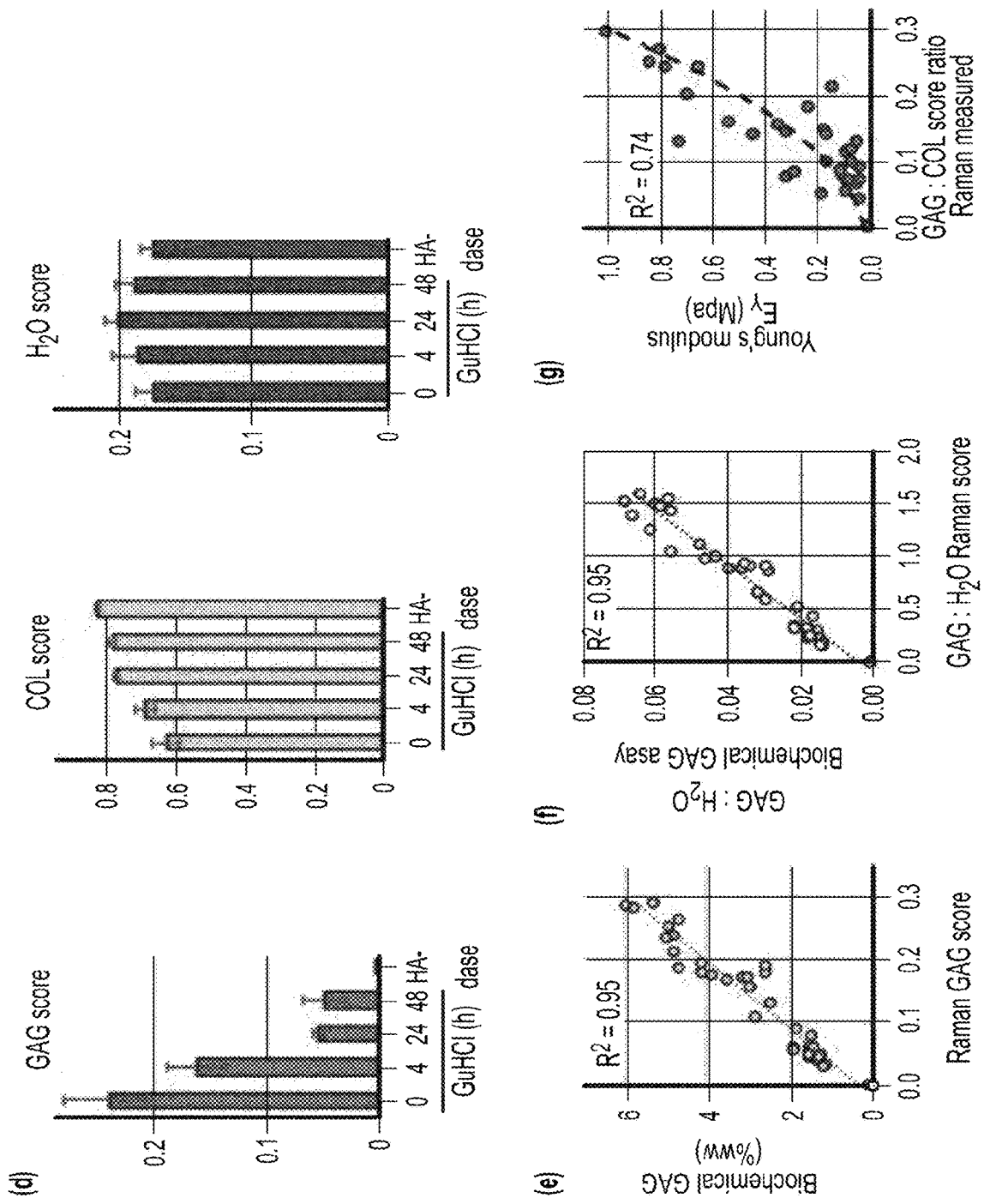
Figure 1F:
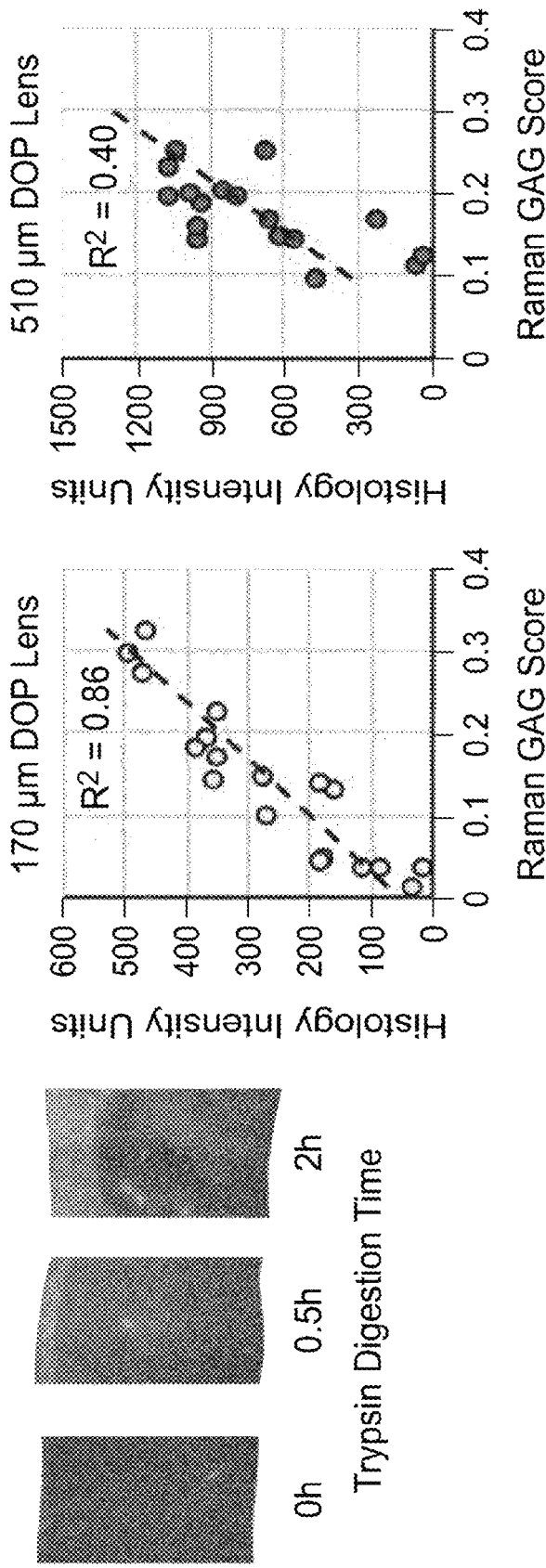
FIG. 1F shows cartilage surface targeting: (A) Trypsin-induced surface GAG depletion from cartilage explants. (B) Surface targeting fiber-optic ball lens improves sensitivity of measures of surface GAG loss.
Figure 1G:
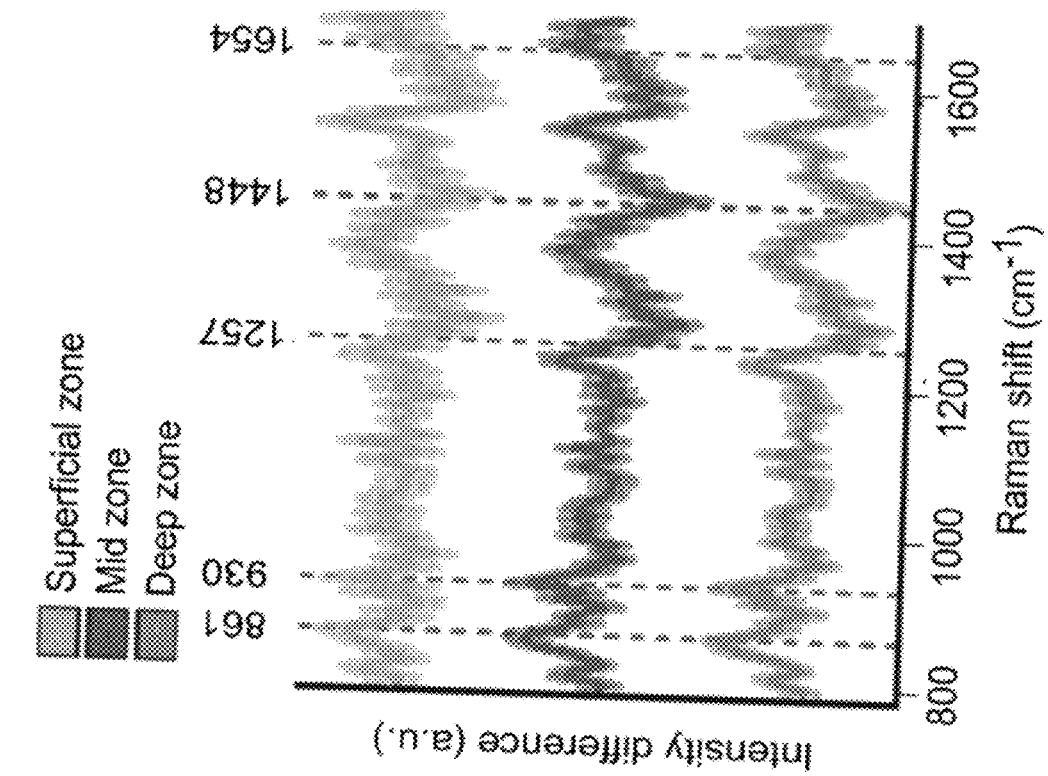
FIG. 1G shows: (a) polarized Raman spectra±1 standard deviation (SO) of superficial (n=45 spectra), mid (n=45 spectra) and deep zone (n=45 spectra) articular cartilage, using the Raman needle probe. (b) Difference spectra±1 SD of the three tissue types.
Figure 1G:
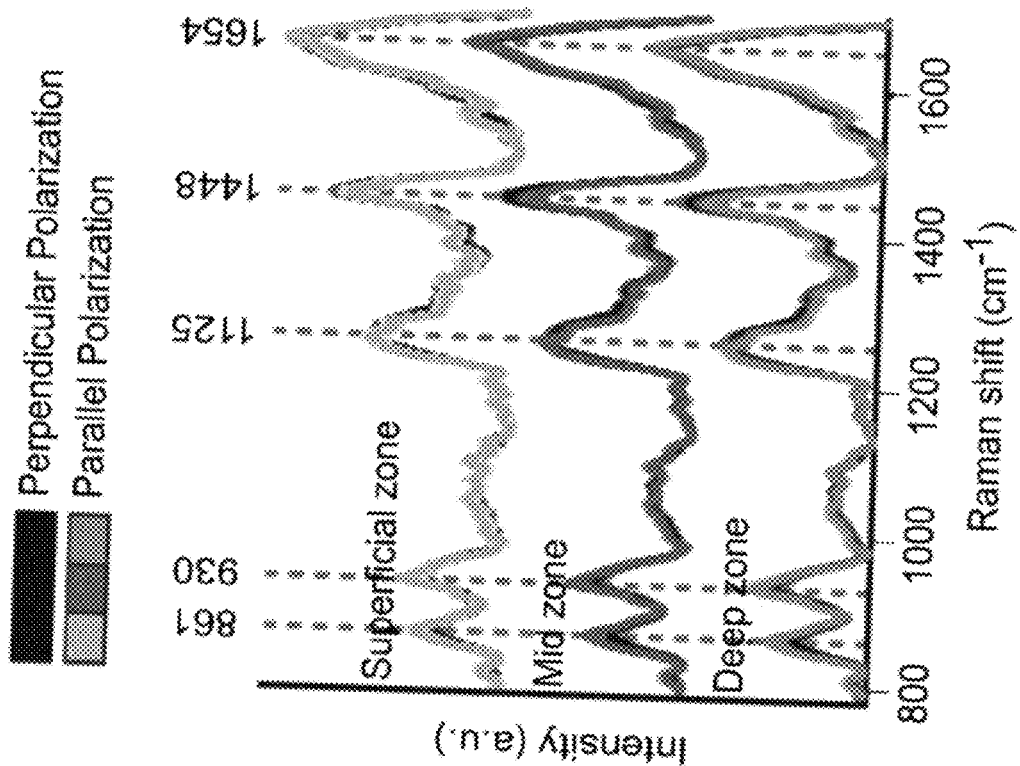
Figure 1H:
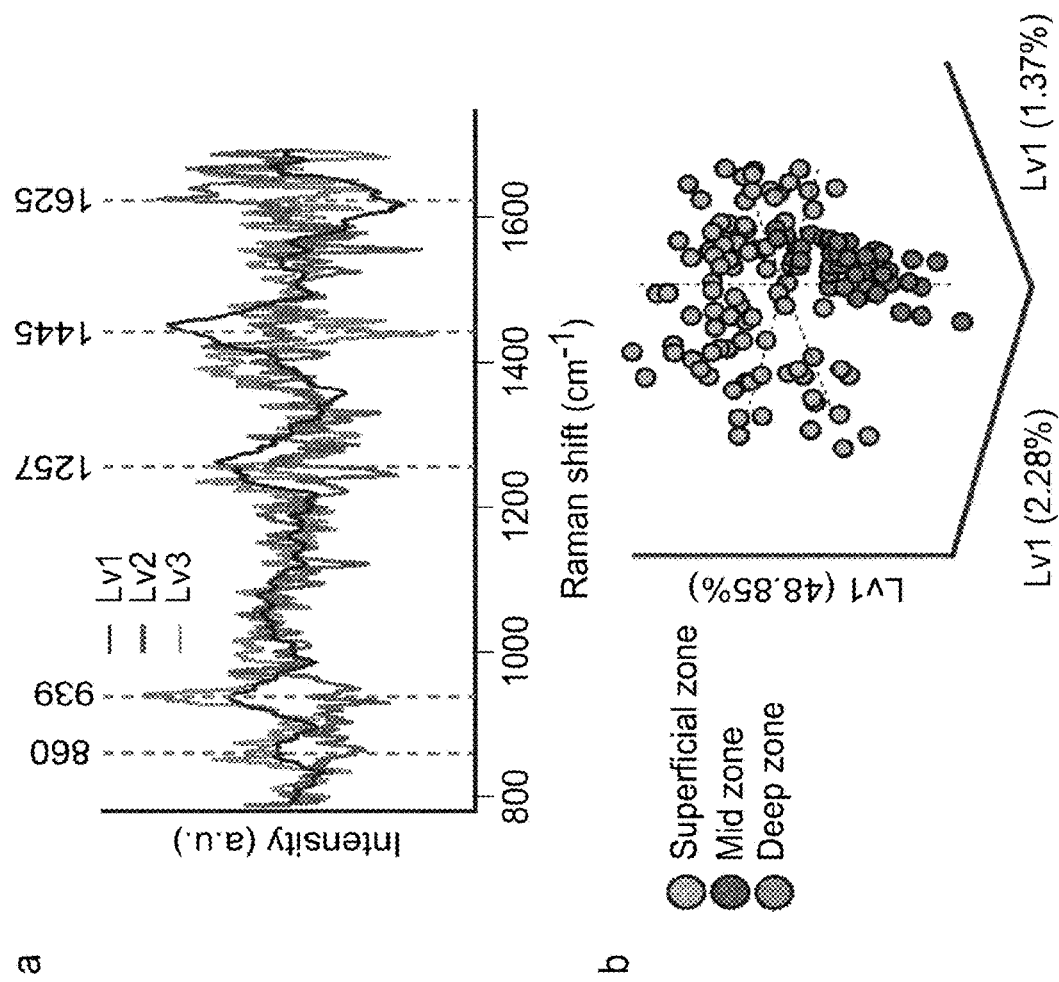
FIG. 1H shows: (a) PLS-DA latent variable (LV) loading of the depolarisation ratio Raman spectra showing distinct peaks associated with collagen (b) PLS-DA latent variable (LV) score plot showing the separation of superficial and deep zone cartilage.
Figure 1I:
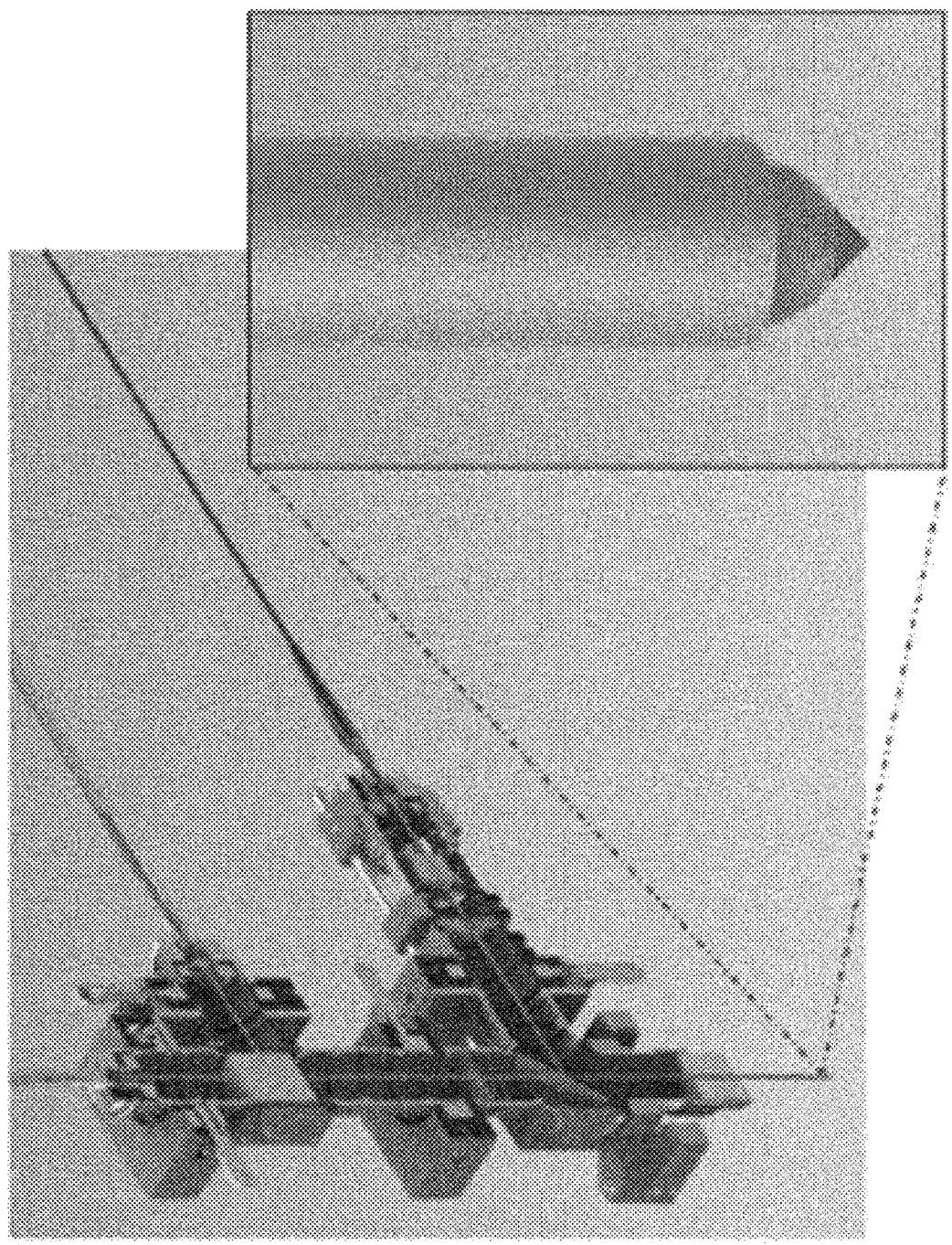
FIG. 1I shows a needle probe in accordance with embodiments of the invention.
Figure 2A:
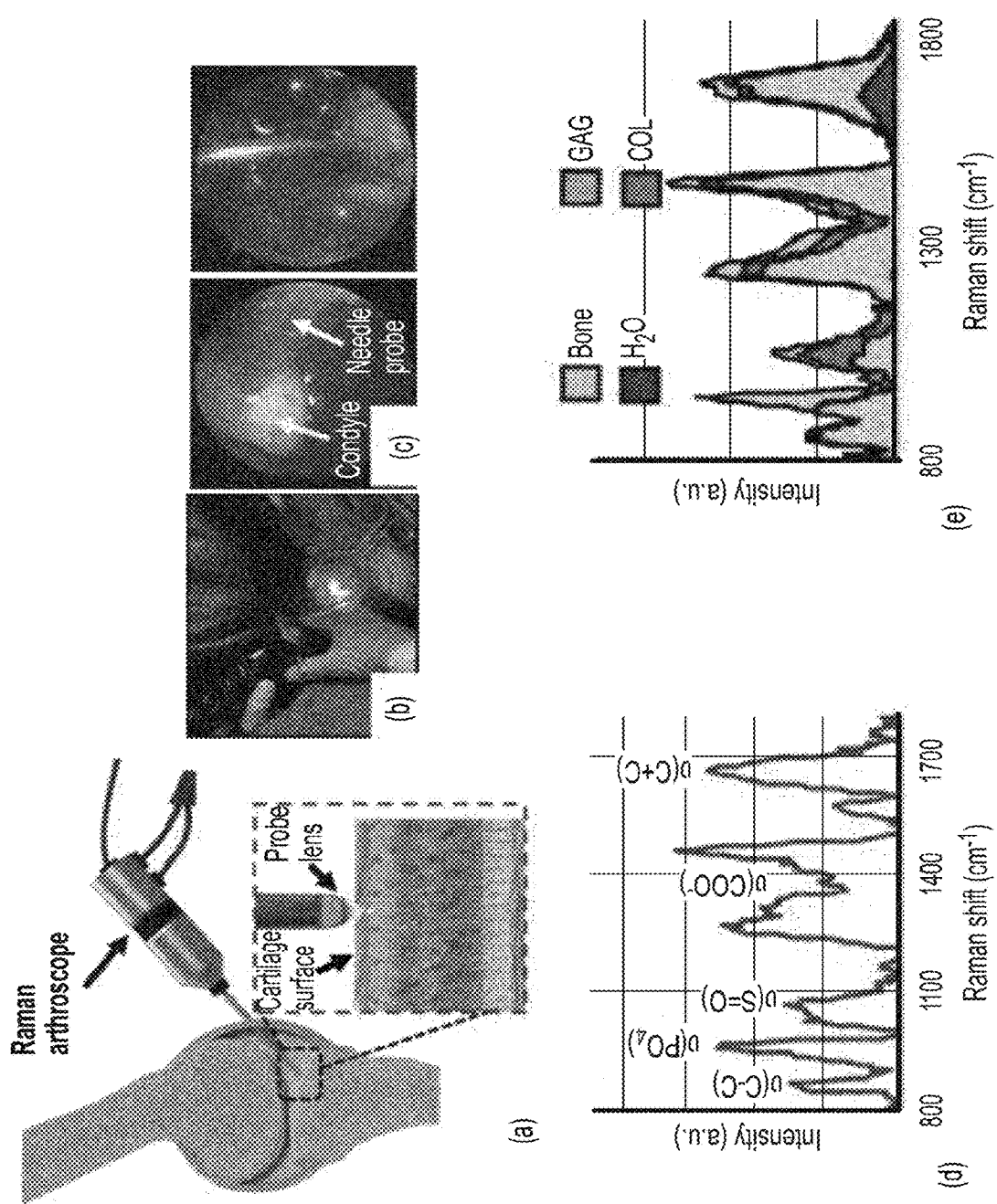
FIG. 2A shows in vivo Raman arthroscopy diagnostics.
Figure 2B:
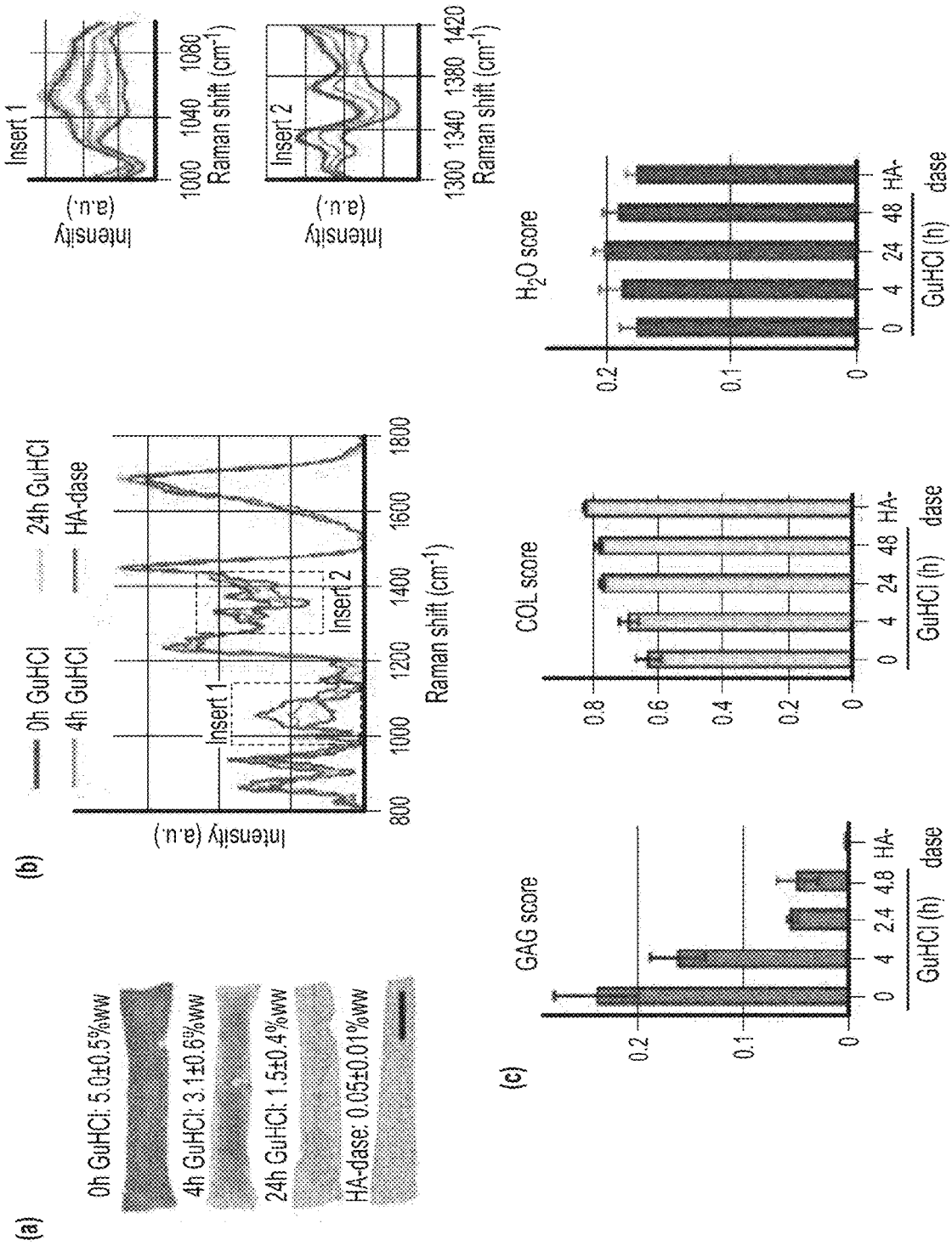
FIG. 2B shows Raman arthroscopy GAG measurements.
Figure 2B:
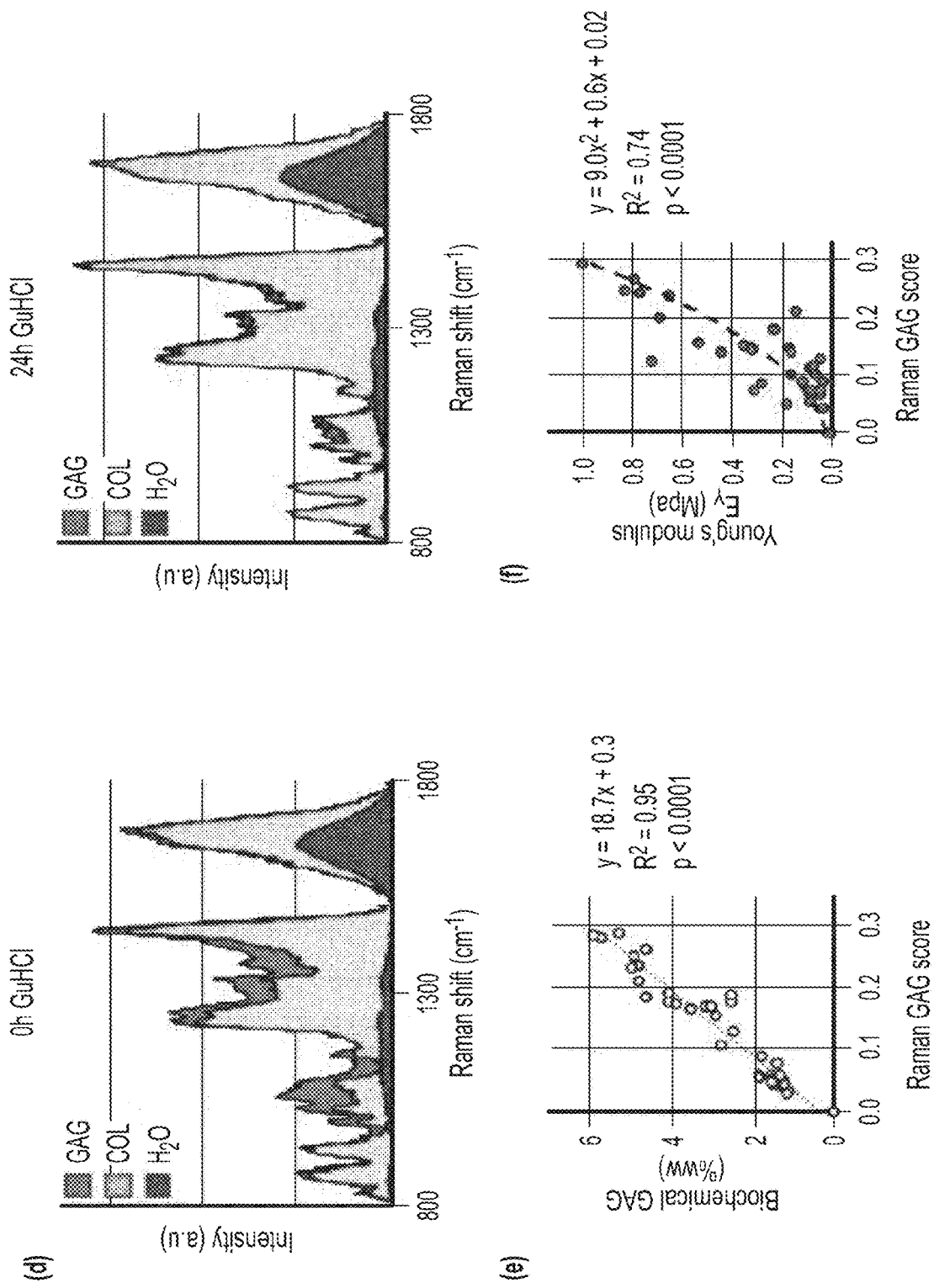
Figure 2C:
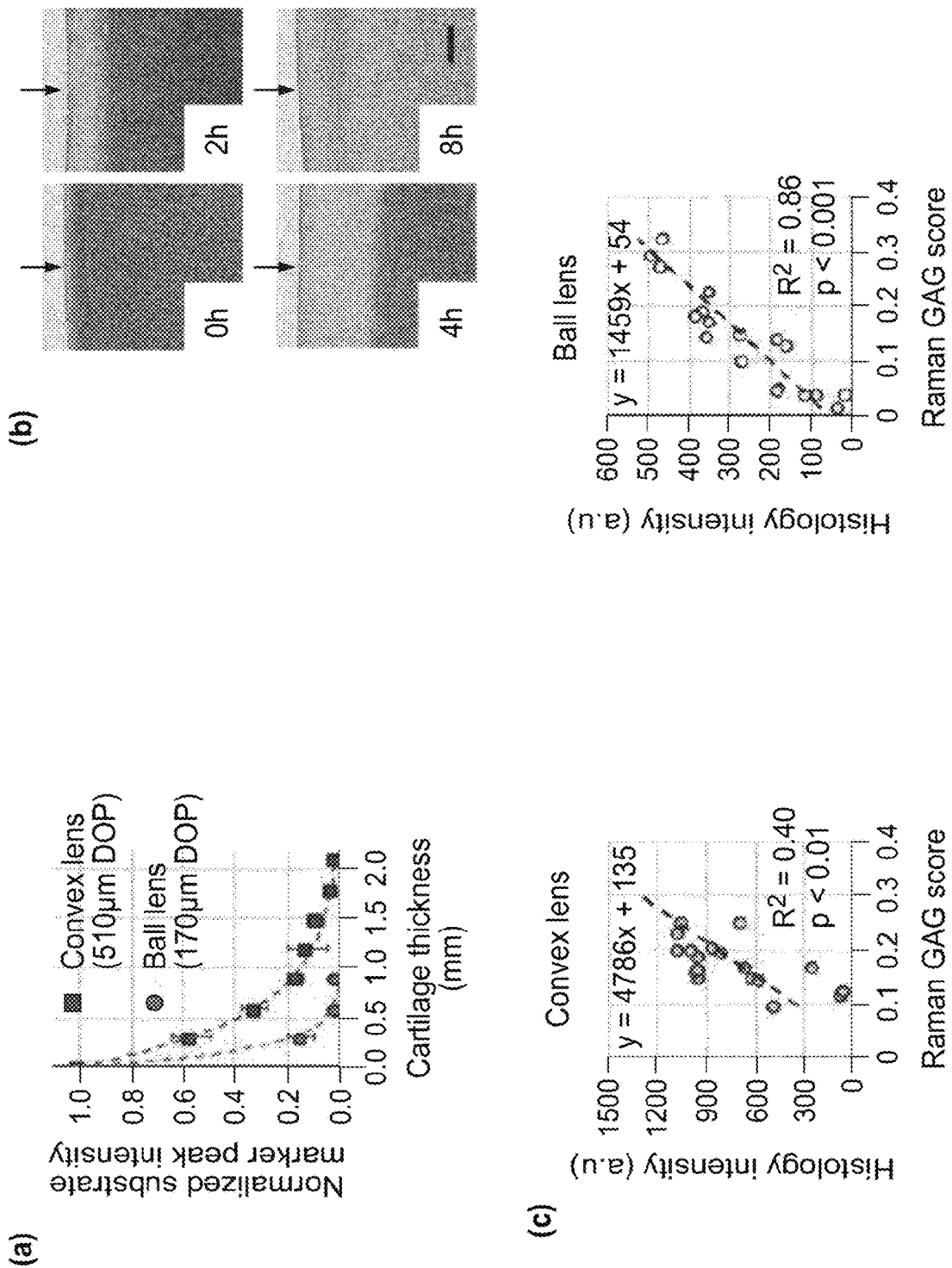
FIG. 2C shows Raman arthroscopy depth selective measurements.
Figure 2D:
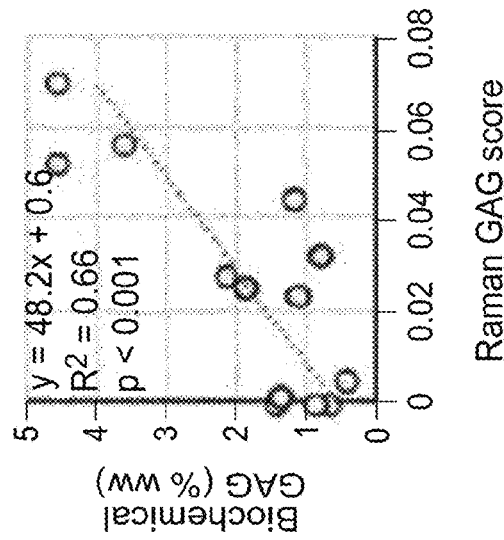
FIG. 2D shows Raman arthroscopy GAG measurements in human cartilage ex vivo.
Figure 2D:
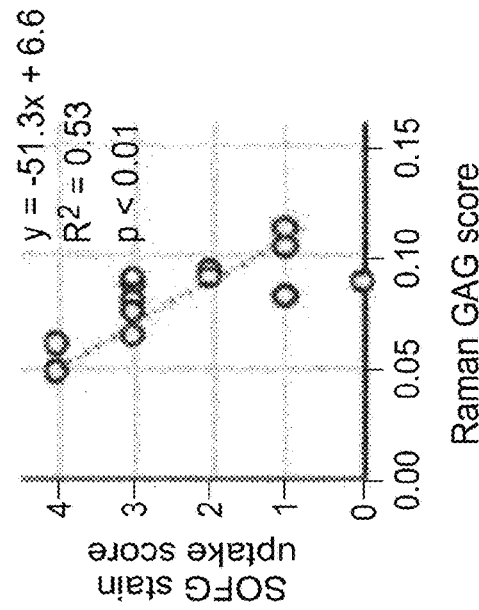
Figure 2D:
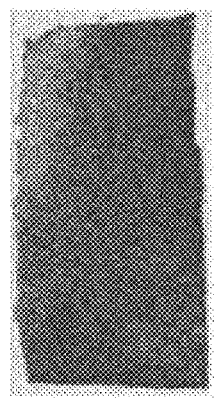
Figure 2D:
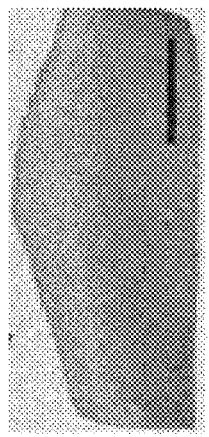
Figure 2D:
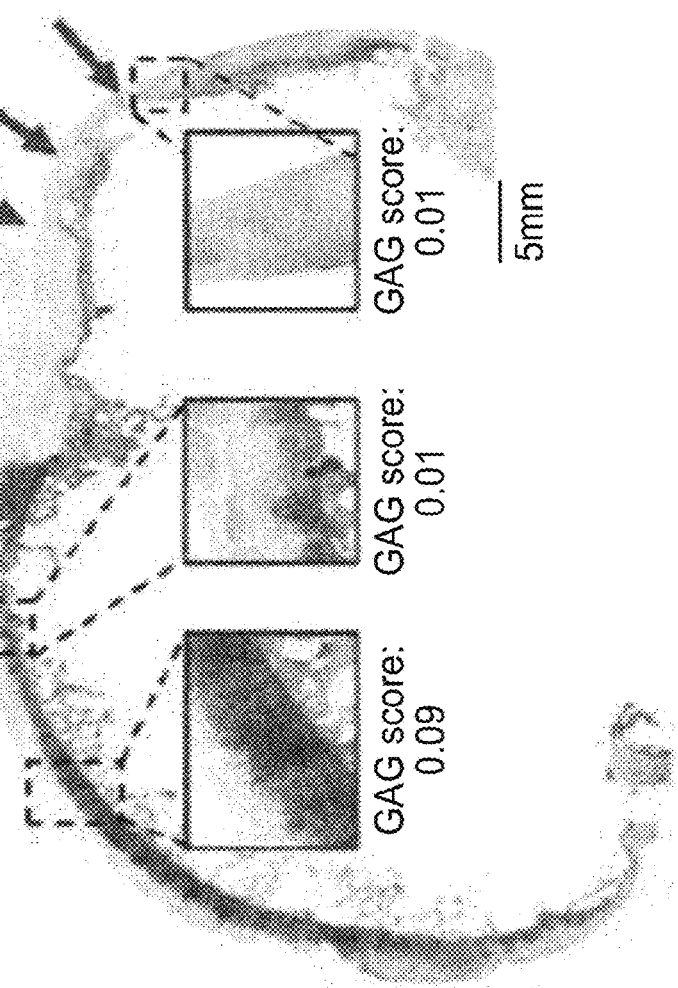
Figure 2D:
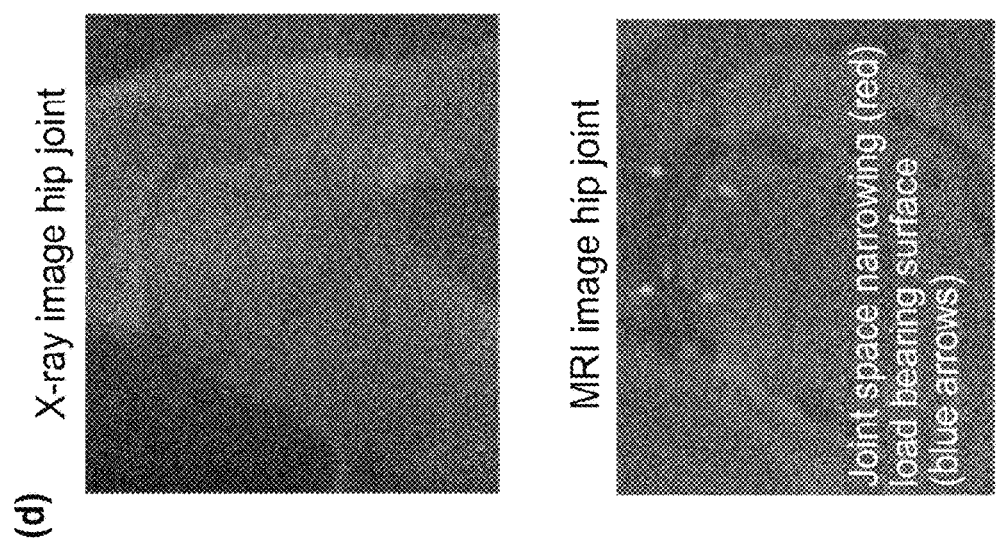
Figure 2E:
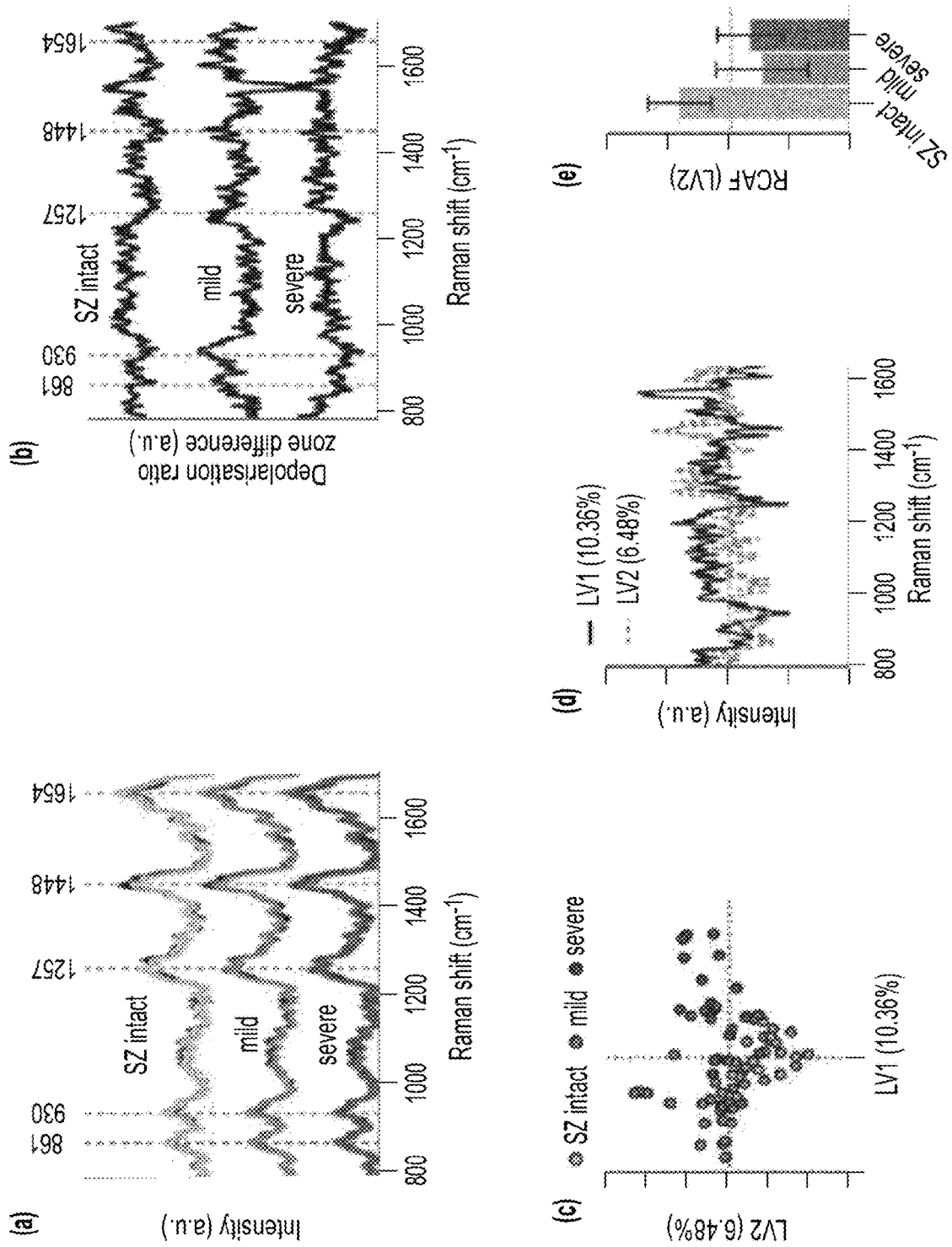
FIG. 2E shows polarized Raman arthroscopy collagen alignment measurements.
Figure 2F:
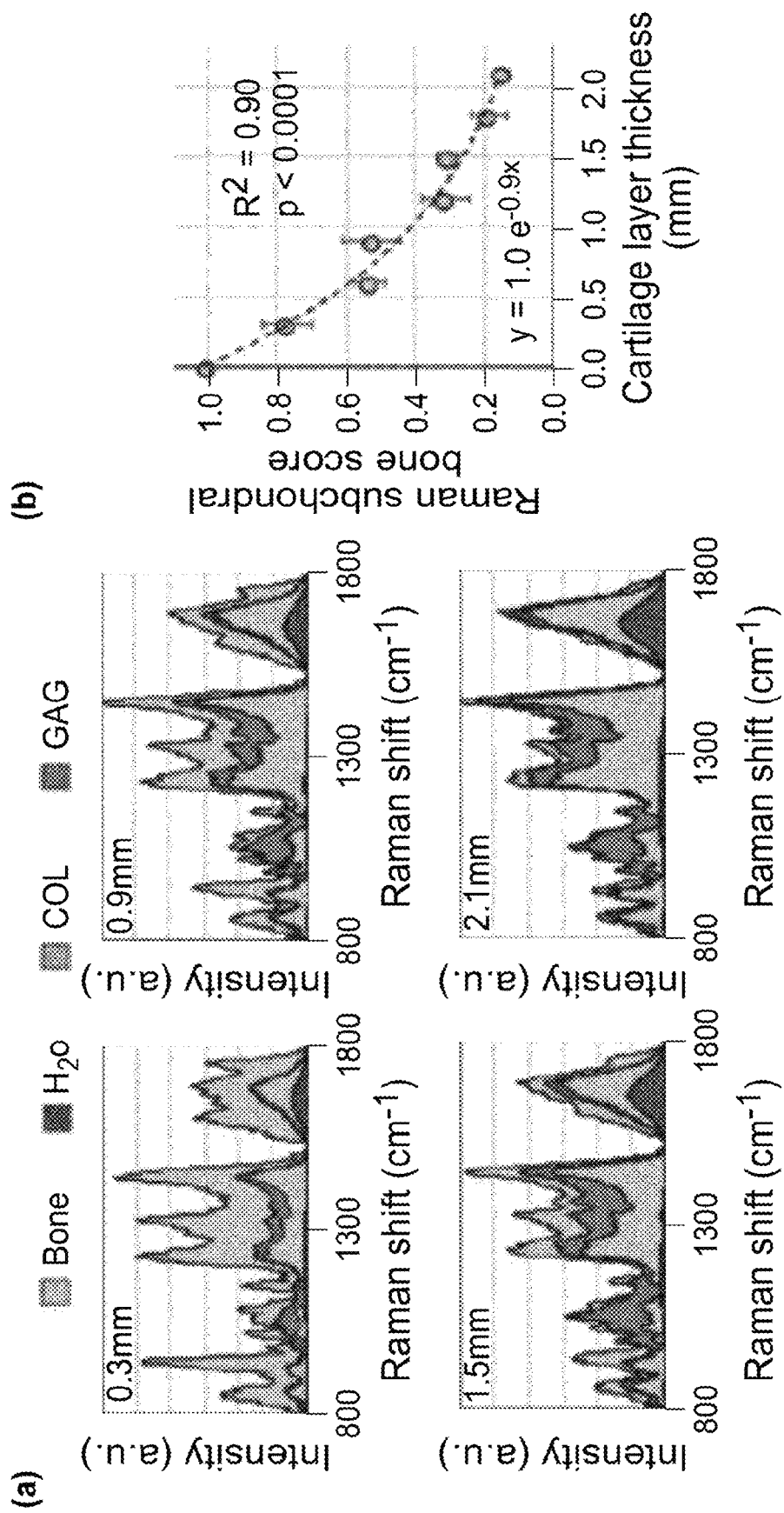
FIG. 2F shows Raman arthroscopy cartilage thickness measurements.

In summary, embodiments of the present invention relate to methods and systems for obtaining biochemical and/or structural information relating to tissue. In some embodiments, a laser beam is sent through a polariser to produce polarised light. The polarised light is then directed down a probe to a lens. The lens focuses the light onto the tissue. The light is reflected off the tissue, producing Raman scattering. The Raman scattering is collected by the probe and directed to a beam splitter, which may be within the probe itself. The beam splitter splits the Raman scattering into two polarised components, parallel and perpendicular to the polarisation of the polarised light. The two polarised components are directed to a spectrometer via bifurcated optical fibres. The bifurcated fibres serve as a slit for the spectrometer, and the separation of the fibres creates two distinctly separated Raman spectra on a CCD camera. The two Raman spectra are then processed and analysed to obtain biochemical and structural information relating to the tissue using a computer program, the computer program being run by a processor.

The present invention has both in vivo and ex vivo applications. In some in vivo embodiments, the probe comprises a needle, the lens is mounted at the distal tip of the needle, and the lens is in contact with the tissue. In order to tightly focus the polarised light onto the tissue, the lens may be a ball lens, for instance, a sapphire ball lens. In some ex vivo embodiments, the probe may comprise a long-distance focusing planoconvex lens to be used alongside a Raman-compatible tissue culture chamber.

Some embodiments of the present invention are directed to a polarised probe that is compatible with hypodermic needles. Embodiments of the present invention relate to a system for obtaining biochemical and structural information relating to tissues, the system comprising a hypodermic hollow needle with an integrated lens positioned at the tip of the needle. The lens is able to collect Raman photons (i.e. Raman scattered light) at the cartilage surface. The system comprises a Raman system that offers simultaneous biochemical (of collagen, GAGs and water) and structural analysis (of collagen). The needle and lens allow polarized Raman photons from collagen fibrils to be preserved. Simultaneous multiplexed measurements of two (perpendicular and parallel) polarisations are made by: (a) splitting the detected Raman scattered light using a polarisation beam splitter; and (b) coupling the split light with two separate fibers to a spectrometer input slit and segmenting a CCD for multiplexing. The system further comprises a computer program which reads out the two Raman spectra simultaneously and performs pre-processing and multivariate analysis on the Raman spectra (perpendicular and parallel), as well as analysis of the perpendicular and parallel polarized Raman spectra for collagen analysis.

By focusing excitation light extremely tightly onto the tissue surface using a confocal lens-based needle probe, polarized Raman spectra can be acquired. The focusing of light achieves the added benefit of collecting Raman spectral acquisition from the topmost cartilage zones, the region where early-stage OA is most prevalent. To this end, embodiments of the invention comprise a new Raman technique that measures two directional polarizations simultaneously (perpendicular and parallel) to extract structural information of the alignment of the collagen matrix. Further, embodiments of the invention comprise a confocal lens-based needle probe which can measure the GAG, collagen, and water content in the topmost zones of articular cartilage, where early stage OA is most prevalent. The simultaneous acquisition of both biochemical (GAG/collagen contents) and structural information (collagen alignment) through the present invention could potentially improve the diagnosis and detection of diseases.

Various aspects and details will be described below with reference to the Figures.

In more detail, we describe herein the development of a novel intra-articular fiber-optic Raman diagnostic platform for the first ever comprehensive assessment of the hallmark degenerative changes that occur in early-stage OA: surface GAG depletion and surface collagen disorganization (alignment loss). The platform consists of: 1) a hypodermic-needle compatible fiber-optic probe, allowing for rapid intra-articular Raman spectral acquisitions of articular cartilage through routine skin puncture, 2) the acquisition of polarized Raman spectra to measure the alignment of collagen in articular cartilage and 3) a lens interface to assess GAG loss and collagen alignment loss at the cartilage surface layers, where early-stage OA degeneration is most prominent (FIG. 1.1). Intra-articular Raman spectroscopy can serve as a revolutionary platform, offering the first ever fully quantitative biochemical diagnostics of early-stage OA. A Raman platform can be label free, minimally invasive, and cost efficient. The successful development of this system can serve as a transformative clinical tool, allowing for: 1) novel assessments of the efficacy of developing OA therapeutics, and 2) a routine clinical diagnostic platform to guide future treatment courses. The implementation of a hypodermic needle-probe interface will allow for the first ever biochemical-based diagnostic platform that can be performed in a clinician's office environment.

A fundamental challenge for the implementation of this platform is the development of novel optic-based hardware that can achieve requisite Raman spectral acquisitions and analysis. It is important to note that previously developed hypodermic-needle compatible fiber-optic Raman probes rely on silica fibers, which are limited by the intense background signal of silica obscuring the tissue Raman signal. As an alternative, hollow needle Raman probes have been developed. However, these systems omit distal optics to increase the numerical aperture (NA) of the probe, leading to the requirement of extended acquisitions times (>60 s), which are not clinically viable. Based on our previous in vivo work in humans, integration times less than 0.5 sec is required to be clinically viable.

Assessing both biochemical quantification of GAG, collagen, and water in the cartilage ECM, as well as the structural characterization of the alignment of the collagen matrix is imperative for early diagnosis of osteoarthritis. An interesting aspect of Raman spectroscopy is that scattered Raman light can be perpendicular or parallel polarized revealing specific information about molecular structures. Few examples of polarized Raman spectroscopy for tissues have been demonstrated and these have only been implemented on microscope setups. It is however well accepted in the biomedical field that polarized Raman spectroscopy of tissue scrambles the polarization due to ballistic (diffuse) light scattering. For this reason, it has not been considered possible to utilize the polarization properties of Raman light for evaluating tissues. The hypothesis of our work was that by focusing excitation light extremely tightly onto the tissue surface, using a confocal lens-based needle probe, polarized Raman spectra can be acquired. The focusing of light achieves the added benefit of collecting Raman spectral acquisition from the topmost cartilage zones, the region where early-stage OA is most prevalent. To this end, we aimed to develop a new Raman technique that measures two directional polarizations simultaneously (perpendicular and parallel) to extract structural information of the alignment of the collagen matrix. Further, we propose that our confocal lens-based needle probe can measure the GAG, collagen, and water content in the topmost zones of articular cartilage, where early stage OA is most prevalent. The simultaneous acquisition of both biochemical (GAG/collagen contents) and structural information (collagen alignment) through our novel platform could potentially improve the diagnosis and detection of diseases.

There are several key challenges that must be solved for Raman spectroscopy to be viable for diagnosis of OA as it must offer both chemical and structural information (i.e., detect both GAG/collagen content and collagen alignment in the joint):

(i) The concentration of tissue components (collagen, GAG, and water) in variable tissue regions of cartilage must be measured (e.g. superficial zone versus deep zone).

(ii) To extract structural information from collagen, the polarization of Raman signals from tissues must be preserved. Conventional Raman probes does not preserve the polarization due to diffuse light scattering. Direct collection of the Raman scattered light with fiber-optics further scrambles the polarization, (iii) Polarized Raman spectra must be measured simultaneously in real-time (<0.5 s) from tissue in both perpendicular and parallel polarized directions. This is currently possible but requires sequential acquisitions in a manner that is not clinical viable.

Multiplexed Polarized Needle Raman Probe

FIG. 1.2 shows a schematic of the multiplexed polarised Raman needle probe system. The Raman spectroscopy system consists of a 785 nm Laser (B&W Tek BRM-785-0.55-100-0.22-FC, 600 mW), a high-throughput near-infrared (NIR) Lens spectrometer (Princeton Instruments Acton LS 785, 750-1100 nm). For the Raman probe, the laser is coupled through a Glan-Laser Calcite polariser (Thorlabs GL10-B, Extinction Ratio=10^5:1) and a 785 nm MaxLine® laser clean-up filter (Semrock LL01-785-25), to polarise and sharpen the laser line before it is directed through the uncoated aluminium needle (Ø=2 mm, l=50 mm) and tightly focused onto the tissue using a sapphire ball lens (AWI 2 mm AR-coated sapphire lens). The Raman scattered light reflected from the tissue is passed back through the needle through an 801 nm edge BrightLine® single-edge dichroic beam splitter (Semrock FF801-Di02-25×36), a 785 nm EdgeBasic™ long-pass edge filter (Semrock BLP01-785R-25), and into a polarising beam splitter Cube (Thorlabs CM1-PBS252, 620-1000 nm, Extinction Ratio=10^3:1). The Raman signal is split into two separate polarised components, parallel and perpendicular to the laser polarisation, and passed through a bifurcated optical fibre (105 um Thorlabs BFY105LS02). The bifurcated fibre serving as the slit is coupled directly into the spectrometer, and the separation of the fibre cores create two distinctly separated Raman spectra on the CCD camera (Princeton Instruments Pixis 400, 120-1100 nm), see FIG. 1.2(*b*).

A polarisation experiment was performed to ensure that the system maintains the laser and Raman polarisation throughout the system. Polarized Raman measurements were performed on a silicon wafer. Due to the high crystalline structure of silicon, the corresponding Raman peak intensity is highly dependent on the polarisation of the incident laser. The laser polariser was adjusted such that rotation of 0 degrees corresponds to the parallel laser polarisation. Each measurement was performed using a 1 s acquisition time. FIG. 1.3(*a*) shows the polarized Raman spectra across a full 360-degree rotation. FIG. 1.3(*b*) shows a polar plot of the intensity change of the dominant Silicon peak at 520 cm$^{-1}$ across a full rotation. From FIG. 1.3(*a*)-(*b*), the oscillating peak intensity demonstrates that the laser polarisation is maintained throughout the system.

In order to determine the depth of field of the system in air, a depth of penetration test was performed on the same silicon sample. The needle was placed on the surface of the sample and raised at a 25 µm interval until the silicon signal was lost. FIG. 1.3(c) shows the depth of penetration through an air medium, resulting in an effective focal length of 325 µm that exactly can target the superficial cartilage layer associated with early OA.

Software Package for Real-Time Data Processing

To control the multiplexed polarized Raman needle system, we have developed a comprehensive real-time software package that reads out the two spectra and pre-processes them individually. The software has been developed in the Matlab scripting environment with C interface for camera control. Data pre-processing including dark signal subtraction, autofluorescence removal and normalisation in order to standardize the Raman spectra prior to multivariate statistical analysis. Following pre-processing the Raman spectra are analysed in two ways: 1) summing the perpendicular and parallel Raman spectra equals non-polarized Raman spectra that can be used for conventional biochemical analysis. Non-negativity linear least squares regression of spectra from purified collagen, GAG and water are to estimate their concentrations in tissues in situ. 2) Calculating a collagen organisation spectrum given by the difference Raman spectra in polarisations (perpendicular-parallel) as well as a ratio spectra (perpendicular/parallel) or anisotropy.

The platform implements critical steps to promote improved diagnosis through both biochemical and structural analysis for diagnostics:

1) A needle with an integrated lens on the tip, to collect Raman photons at the cartilage surface where there is early onset of OA. A hollow needle with a lens allows us to preserve polarized Raman photons from collagen fibrils. In the field, this is an unexpected finding since it is well accepted that tissue scrambles the polarisation.

2) Multiplexed measurements of two (perpendicular and parallel) polarisations simultaneously by splitting the Raman scattered light using a polarisation beam splitter and coupling this with two separate fibers to the spectrometer input slit and segmenting the CCD for multiplexing. Only in this way the technique becomes clinical viable through fast acquisitions.

3) A software package that reads out the two Raman spectra simultaneously and performs pre-processing, and multivariate analysis on the Raman spectra (perpendicular+parallel) and analysis of the perpendicular and parallel polarized Raman spectra for collagen analysis.

In order to demonstrate the functionality of the developed system here we assess the ability of the novel multiplexed fiber-optic polarized Raman probe to assess the key degenerative change that occurs in early-stage OA: i) GAG depletion from the cartilage surface as well as ii) detection of changes to collagen structural alignment:

Quantification of GAG Depletion in Articular Cartilage Using the Multiplexed Polarized Probe In order to assess the capability of the multiplexed polarized Raman probe for quantification of GAG, we compared measures from the technique to conventional biochemical assays. Here, two unique model systems are employed: 1) Thin cartilage explant slices where varying levels of GAG depletion are induced uniformly throughout the tissue, and 2) Full thickness explants, where GAG is depleted from the articular surface, as encountered in early-stage OA.

Uniform GAG Depletion Model:

We initially examined of the ability of our fiber-optic Raman probe with multivariate spectral analysis to quantify the GAG content of articular cartilage in uniform depleted tissues. Deep-zone bovine cartilage explants (Ø×0.8 mm) served as a simplified model system due to their low ECM heterogeneity (4). Explants were treated with to 4M guanidine-HCl (GuHCl) for 0 h, 4 h, 24 h, or 48 h to induce varying degrees of uniform GAG depletion, or to hyaluronidase (HAdase; 24 h at 5 mg/mL) to induce full GAG depletion (FIG. 1.5A). COL contents were statistically unaltered by treatments and water content changes were minor. Raman spectra were acquired and pre-processed (background subtraction, 5th order polynomial baseline subtraction, area-under-curve normalization). GAG-depletion induced a prominent Raman signal intensity decrease at the 1000-1100 $cm^{-1}$ and 1200-1300 $cm^{-1}$ wavenumber ranges (FIG. 1.5B). Spectra were subjected to multivariate regression using the normalized Raman spectra of purified reference chemicals of cartilage ECM constituents (GAG [chondroitin sulfate], COL [chicken sternal COL-II], $H_2O$ [PBS]; Sigma), yielding the "score" or relative contribution of each constituent to the cartilage Raman spectra. FIG. 1.5C depicts the cumulative contribution of each constituent based on regression scores. GAG scores decreased with depletion treatments (FIG. 1.5D). COL and $H_2O$ scores were relatively unaltered (FIG. 1.5D). Results demonstrated that Raman GAG score exhibited exceptional agreement with the biochemical-assay measured GAG contents, with an $R^2$ value of 0.95 (FIG. 1.5E-F). The GAG score further strongly correlated with tissue mechanical properties (FIG. 1.5G). The results of this study demonstrate for the first time that the multiplexed polarized Raman needle probe can indeed accurately measure the GAG content of articular cartilage, thus supporting its use as an early-stage OA diagnostic tool.

Surface GAG Depletion Model:

To demonstrate the surface targeting capability of our Raman probe, full thickness bovine cartilage explants were treated with trypsin (1000 µg/mL at 4° C. for 0, 0.5, 2, 4, or 8 hours), inducing progressive surface GAG depletion, akin to early OA. Raman spectra were acquired through the articular surface with a shallow focus fiber-optic ball lens (170 µm depth of penetration [DOP]) and a deep focus lens (510 µm DOP). Multivariate regression was applied, yielding Raman GAG scores for each lens. GAG scores were compared to direct GAG measures, computed from integration of depth dependent colorimetric GAG profiles from saf-O histology sections (weighed by the lens-specific DOP profile (FIG. 1.5), yielding the GAG in the Raman acquisition window). The low DOP focus lens substantially improved the correlation and sensitivity of Raman measurements (FIG. 1.6). This experiment demonstrates the critical dependency of lens DOP for the diagnostic accuracy of Raman spectroscopy.

Multiplexed Polarized Raman Spectroscopy of Collagen Structure in Articular Cartilage We then aimed to investigate if the polarised Raman signal could be used to detect subtle changes in an ex vivo tissue model for early OA. In early-stage OA, the parallel aligned superficial layer is disrupted, exposing the middle zone (isotropic structure) of the tissue, In late-stage OA, the superficial and mid cartilage layer is absent, and the deep zone cartilage is exposed. To assess the capacity of our multiplexed polarised Raman probe to assess changes to collagen alignment, measurements were performed on cartilage tissues with different zones removed. Here, articular cartilage explants (Ø×3 mm) with the articular surface initially intact were procured from the femoral condyles of 2-month-old bovines. Zones of the tissue were selectively trimmed from the tissue via a custom cutting device. Groups of explants were generated as: 1) articular surface intact (0 μm excised), 2) superficial zone removed (topmost 300 μm excised), 3) superficial/middle zones removed (600 μm excised). After trimming, explants were treated with hyaluronidase (5 mg/mL for 24 h) to remove interfering GAG Raman signal, fixed in 3.7% paraformaldehyde, and washed in PBS before Raman analysis. This is because it is well known that the concentration of GAG varies through the depth of articular cartilage that might obscure the polarized Raman signal. The Raman needle probe was placed in gentle contact with the tissue and sets of polarized Raman spectra were measured. FIG. 1.7(a) shows polarised Raman spectra±1 standard deviation (SD) of the bovine cartilage explants. A total of 30 explants (superficial zone (n=10), mid zone (n=10) and deep zone (n=10)) were measured (n=5 spectra per sample) using 10 s acquisition time to obtain a very high signal to noise ratio (SNR). The power on the sample was 140 mW.

Intense Raman peaks were observed for both polarisations at 861, 930, 1257, 1448, and 1654 $cm^{-1}$. The peaks tentatively correspond to hydroxyproline, C—C stretch, Amide HI, CH2 bending, and Amide I, respectively. These peaks are due to the collagen that is abundant in cartilage. We found very consistent differences between the parallel and perpendicular polarisation in all three tissue types, in particular at 861, 930, 1251 and 1448 $cm^{-1}$. This can be observed in the polarisation difference spectra±1SD FIG. 1.7(b). Most importantly, we also found that there were subtle but very consistent differences between the three zones spectra.

To take advantage of the fill range of polarisation modulated Raman peaks, we employ partial least squares discriminant analysis (PLS-DA) with cross-validation on the depolarisation spectra (parallel/perpendicular). We developed a robust model with a complexity of only one latent variable (LV) significantly reducing the risk of overfitting. FIG. 1.8(a) shows the loading for the first LV1 from the PLS-DA. The LV1 accounted for a total of 48.85% of the variance in the X-Block and 22.58% in the Y-Block. Four peaks related to C—C stretch, Amide in, CH2 bending, and Amide I were prominent in LV1, strongly suggesting that LV1 is related to collagen orientation. FIG. 1.8(b) shows a histogram, with normal distribution, of the first PLS-DA score for each of the three tissue tissues. We found clear discrimination between the superficial vs mid zone/deep zone cartilage. PLS-DA could classify the tissues with sensitivity/specificity of (superficial zone: 73.3%/81.1%, mid zone: 95.6%/57.8%, deep zone: 55.6%/47.8%). Not surprisingly, we found that the model is best at discriminating between the superficial zone and the deeper zones. This correlates well with the structure of cartilage, suggesting the system has great potential for early OA detection capabilities.

Our previous studies have shown that Raman spectroscopy can detect GAG, which is a hallmark of OA. Here we demonstrate through a hypodermic needle that we can detect the second major characteristic of OA; destruction of the superficial collagen alignment. In the future, we aim to apply this technology and combine GAG and collagen analysis to offer complementary information for OA diagnosis in humans. Further, this technology can potentially be used to monitor the efficacy of therapeutic compounds. For instance, very recently there are promising therapeutic interventions under investigation such as Sprifermin. With the relatively low resolution of MRI and contrast CT the needle probe can become a crucial technology to sense the degeneration and repair of the cartilage surface in the earliest stages.

In summary, we have built a novel multiplexed Raman needle probe system. The Raman needle probe was tested on a model for OA in articular cartilage tissue. We report a good sensitivity and selectivity for detecting subtle structural changes in the superficial zone of an OA tissue model. We have shown that through a combination of the multiplexed polarisation needle probe and the diagnostic model, we can distinguish collagen alignment, which shows great potential for future early-stage OA diagnosis.

Advantages

Conventional diagnostic techniques such as CT and MRI are only able to assess late stage OA after considerable cartilage erosion has occurred as disease modifying therapies are no longer viable. New diagnostic technologies, such as contrast enhanced MRI (dGEMRIC) have been shown to diagnose early-stage OA GAG loss, but encounter a host of limitations, including the use of potentially harmful contrast agents, a highly extended patient prep/imaging durations, and the need for large, highly expensive equipment infrastructure. Our proposed polarized confocal needle probe provides considerable advancements over the existing methodologies by diagnosing early stage OA (GAG loss and collagen disorganization) with a platform that is safe and minimally invasive. The platform is low cost (relative to conventional radiology equipment) and thus will serve as the first biochemical-based diagnostic platform that can be performed in a clinician's office environment.

No needle-based Raman methods exist for diagnosing OA. This invention offers the following concrete advantages over other Raman techniques in general:
1) The invention offers real-time biochemical information (GAG/collagen content) and structural Information (collagen alignment) of tissues in vivo.
2) The design of the probe and spectrometer input coupling enables two polarisations to be measured simultaneously. This allows for rapid collagen alignment measurement.
3) The needle probe with integrated lens focuses the light tightly so that polarisation information of tissue can be maintained.
4) Lens-interface further allows for measurement of GAG loss from cartilage surface, a hallmark of early-stage OA.

Uses

Embodiments of the invention may be used in the following applications within the clinical orthopaedics field:
Clinical osteoarthritis diagnostics
Veterinary osteoarthritis diagnostics
Clinical and pre-clinical research models to understand osteoarthritis degeneration and identify novel drug/treatment candidates.
Biochemical/structural assessments of degeneration of other synovial joint/connective tissues (tendon, ligament, meniscus, intervertebral disk)
Tissue bank tissue quality assessments (e.g. cartilage allografts). Selection of optimal tissues for clinical implantation.

Regenerative medicine applications: 1) Assessments of cartilage repair progress in vivo, 2) In vitro quality assessments of engineered tissues prior to implantation.

Embodiments of the invention may be used in the following applications within other clinical fields spanning across in vivo diagnostics and surgery guidance including:

Cancer diagnostics (breast cancer, lymph node tumours, oral and mucosal cancers, head and neck cancer, and skin cancer)

Fibrosis diagnostics

Enamel analysis

Brain surgery

The multiplexed polarized Raman technology can be implemented as a research tool in a microscope for lab research-based polarized Raman imaging. Importantly, in contrast to conventional Raman probes this probe is suitable for imaging. Embodiments of the invention may be used for multimodal imaging such as optical coherence tomography, confocal reflectance/fluorescence imaging or even multiphoton imaging.

Embodiments of the invention may be used outside the field, for example, in process analytical technology (PAT).

Further Applications and Testing

1. Raman Needle Arthroscopy for In Vivo Molecular Diagnostics of Early Stage Osteoarthritis Overview Embodiments of the invention described in this section, relate to in vivo molecular diagnostics of early stage osteoarthritis. The implementation of processing and analysis on the Raman spectra using multivariate regression to ascertain the contribution of individual spectra corresponding to the ECM constituents GAG, COL, and $H_2O$ to the cumulative Raman cartilage spectra is described in more detail.

The processing and analysing step of the present invention described above may further comprise decomposing and isolating relative contributions of major cartilage ECM constituents to the Raman spectra. The decomposing and isolating of the relative contributions of major cartilage ECM constituents to the Raman spectra may use regression coefficients derived from multivariate least-squares-regression analysis. This analysis may be performed by a machine learning program.

Methods

Raman Needle Arthroscopy Instrumentation

A custom polarized Raman needle arthroscopy system was developed for in vivo OA diagnostics by intra-articular entry through a hypodermic needle, as shown in FIG. 2.1a-c.

FIG. 2.1 shows in vivo Raman arthroscopy diagnostics. FIG. 2.1(a) shows a schematic of fiber-optic Raman needle arthroscopy probe for OA diagnostics. The Raman spectroscopy system consists of a near infrared (NIR) laser, a spectrometer with an NIR deep depletion CCD, and a novel needle Raman probe that enables simultaneous acquisition of both the parallel and perpendicular polarized Raman signal. FIG. 2.1(b) shows in vivo Raman spectroscopy assessment of ovine stifle joint. FIG. 2.1(c) shows a Raman probe in direct contact with femoral condyle as visualized by arthroscopic camera. FIG. 2.1(d) shows Raman spectra acquired in vivo of ovine femoral condyle articular cartilage. FIG. 2.1(e) shows 2D stacked area graph showing contribution of GAG, COL, H2O, and subchondral bone to composite ovine cartilage Raman spectra after multivariate linear.

Multivariate Statistical Analysis

The Raman spectral contribution of GAG and water are characteristically "buried" under the much stronger COL signal (FIG. 2.1(e)), thereby obscuring assessment of tissue GAG and water content. Here, we add to what is described above by decomposing and isolating the relative contribution of the major cartilage ECM constituents (GAG, COL, and $H_2O$) to the Raman cartilage spectra using regression coefficients derived from the multivariate least-squares-regression analysis:

$$Cartilage_{spectra} = GAG_{score}*(GAG_{REF}) + COL_{score}*(COL_{REF}) + H2O_{score}*(H2O_{REF}) \quad (1)$$

Where $GAG_{REF}$, $COL_{REF}$, and $H2O_{REF}$ are the component spectra of purified reference chemicals of each ECM constituent (FIG. 2.1(e)). The $GAG_{score}$, $COL_{score}$, and $H2O_{score}$ "scores" are the regression coefficients that reflect the contribution of the spectra of each constituent element to the cumulative Raman cartilage spectra. Further, we expect non-linear regression methods based on recent development in deep learning to be highly advantageous as it can model the optical properties of tissues.

Raman Arthroscopy GAG Measurements Ex Vivo

The capability of Raman arthroscopy and multivariate analysis to portray cartilage GAG content was assessed. Capitalizing on low ECM compositional heterogeneity, deep zone cartilage was extracted from explants (Ø5 mm±0.8 mm) of femoral condyle hyaline cartilage of 2-month-old calves (Green Village Packing Co, NJ; n=5 animals). To simulate the progressive loss of GAG observed in early stage OA, explants were subjected to stepwise GAG depletion using timed exposure (0, 4, 24, or 48 hours; n=10 explants per group) of 4M guanidine hydrochloride (GuHCl). Overnight exposure to 3 mg/mL hyaluronidase (HA-dase; 37° C. and pH 6.0) produced full GAG depletion. Raman spectra were acquired on the central region of each explant using a convex lens and compared to the GAG, COL, and $H_2O$ content and equilibrium compressive elastic modulus ($E_Y$) of a Ø3 mm central core.

Raman Arthroscopy Depth Selective Measurements Ex Vivo.

As cartilage degeneration occurs in a depth-dependent manner, initiating predominantly in the topmost regions of the tissue, we next investigated how depth selectivity affects the quantification of GAG using a shallow focusing (needle and 2 mm ball lens) and deep focusing lens (convex lens). To induce progressive depth dependent GAG reduction, mimicking early stage OA, full thickness bovine cartilage explants (Ø6 mm) were treated with 500 µg/mL trypsin (pH 7.2 at 4° C.) for 0, 0.5, 2, 4, or 8 hours (n=4 explants per group). Raman spectra were acquired at the articular surface using the surface-targeting ball lens and the deep focusing convex lens. Subsequently, explants were fixed, paraffin-embedded, sectioned, and stained with Safranin-O/Fast Green. Safranin-O colorimetric profiles were mapped through the depth using the red channel intensity and normalized to the average intensity at the 1.5 mm depth position. For each lens, profiles were multiplied by the DOP decay curves (see Results) and integrated through the tissue depth, yielding the colorimetric-based GAG content in the lens-specific Raman imaging window. For each lens, colorimetric GAG was compared to Raman GAG scores.

Raman Arthroscopy GAG Measurements in Human Explants Ex Vivo.

To establish the clinical relevance of the derived Raman GAG scores, Raman needle arthroscope measurements were performed on Ø4.0 mm chondral explants (n=13) excised from the distal femoral condyles of three cadaveric human knees (NDRI; age/sex: 70/♀, 75/♂, 65/♀; 4-5 explants per donor). Specimens exhibited no visual signs of surface damage or fibrillation (Outerbridge scores 0-1). Raman spectra were acquired with both the ball lens and convex lens. Subsequently, explants were diametrically cut in half. For one half, the topmost 500 μm of cartilage was excised for GAG content analysis. Histological sections from the other half were analysed for a modified-Mankin-based Safranin-O-Fast-Green (SOFG) stain uptake score, based on percentage depletion per total area of unmineralized articular cartilage, as described. Ball lens Raman GAG scores were compared to surface cartilage GAG content measures. Convex lens Raman GAG scores were compared to the SOFG stain uptake score. To illustrate Raman arthroscopy's ability to characterize the spatial variation in tissue composition along a contiguous joint surface, Raman GAG scores were acquired at discrete anatomical sites along the articular surface of an excised human femoral head specimen was obtained from a total hip arthroplasty procedure (50/♀; Kellgren-Lawrence grade 1). Raman GAG scores were acquired at three discrete anatomic sites along the articular surface and compared to corresponding Safranin-O intensities.

Polarized Raman Arthroscopic Assessment of Zonal Collagen Alignment Ex Vivo

We evaluated whether polarized Raman arthroscopy could evaluate loss of cartilage SZ during cartilage degeneration. Full thickness bovine explants were subjected to mechanical surface abrasion using a linearly reciprocating sander (600 grit) under 40 kPa of normal stress. Abrasion was used to remove sequential zonal layers (n=5 explants per group): no abrasion (SZ intact), mild abrasion (120±26 μm tissue removed, exposing the MZ), and severe abrasion (437±60 μm tissue removed, exposing the DZ). All explants were GAG depleted via HA-dase to mimic early stage OA GAG depletion. Using monochromic laser light excitation at a laser power of 140 mW, the parallel and perpendicular polarized Raman spectra (n=5), were collected from each sample over a 5 second acquisition time. A total of 25 individual sets of polarized Raman spectra were measured for each group, resulting in 75 sets of polarized Raman spectra. The depolarization ratio (perpendicular/(parallel+x)) of each spectral set was calculated using the arbitrary DC component to avoid near infinite values. The depolarization ratio was used for input to a partial least squares-discriminant analysis (PLS-DA), with leave-one-out cross validation to build an unbiased model that discriminated among the surface abrasion groups. PLS-DA is a powerful multivariate regression technique that can efficiently extract the spectral variations of interest such as changes associated with alignment or chemistry. Orthogonal latent variables were derived from Raman intensity peak positions highly associated with polarization sensitive collagen bands that maximized the covariance between spectral variation and abrasion group affinity. All statistical analysis was performed with Matlab using PLS-Toolbox.

Raman Arthroscopy Cartilage Thickness Measurements Ex Vivo

To assess cartilage thickness using Raman spectroscopy, the cartilage layer of bovine osteochondral explants was variably excised to achieve chondral thicknesses ranging from 0.3 mm to 2.1 mm. Raman spectra were acquired via the convex lens to better detect the Raman spectra from the subchondral bone through diffuse light scattering. Using known reference spectra of cartilage ECM (GAG, COL, $H_2O$) as well as bovine subchondral bone ($Bone_{REF}$; FIG. 2.1($e$)) and its regression coefficient ($Bone_{score}$), multivariate linear regression was applied to the aggregate Raman spectra.

Raman Arthroscopy for In Situ and In Vivo Diagnostics

Confounding factors related to in situ intra-articular Raman diagnostic measurements were further assessed, including: 1) interference from synovial fluid, 2) sensitivity of acquired Raman spectra to probe-to-cartilage surface incidence angle, and 3) sufficient acquisition time to achieve reliable Raman signal. Further, in situ measurements of cartilage ECM composition were performed on intact ex vivo bovine antebrachiocarpal (wrist) joints before and after intra-articular enzymatic GAG depletion treatment using the Raman arthroscopy probe inserted intra-articularly through a 10-gauge hypodermic needle trocar.

In vivo Raman arthroscopy was approval by University of Pennsylvania Veterinary School IACUC. Raman spectra were collected from the distal femoral condyle articular cartilage of a live skeletally-mature sheep via a mini arthrotomy of the stifle joint.

Results

Raman Arthroscopy GAG Quantification

FIG. 2.2 shows Raman arthroscopy GAG measurements. FIG. 2.2($a$) shows Guanidine hydrochloride (GuHCl) and hyaluronidase (HA-dase) induced GAG depletion of cartilage explants (Safranin-O histology and DMMB-measured GAG levels). Scale bar=1 mm. FIG. 2.2($b$) shows GuHCl/HA-dase-induced decrease of measured Raman arthroscopy spectra intensity at 1000-1100 $cm^{-1}$ and 1300-1450 $cm^{-1}$ wavenumbers (mean±standard deviation). FIG. 2.2($c$) shows regression coefficients (scores) for GAG, COL, $H_2O$ from multivariate linear regression decomposition of Raman spectra for GuHCl/HA-dase timed exposure groups. FIG. 2.2($d$) shows a 2D stacked area graph showing cumulative contribution of GAG, COL, $H_2O$ spectra to composite Raman cartilage spectra after multivariate linear regression. GAG spectral contribution attenuated after GAG depletion by GuHCL, while COL and $H_2O$ contributions relatively unaffected. Bi-variate regression between Raman GAG scores vs: FIG. 2.2($e$) assay-measured GAG content and FIG. 2.2($f$) compressive elastic modulus ($E_Y$) for explants.

Chemical treatments induced a stepwise depletion of GAG from cartilage explants (FIG. 2.2$a$). COL content (mean 4.4±0.9% per wet weight [% ww]) and $H_2O$ content (mean 86.7±2.6% ww) were minimally altered by these treatments. Concomitant with chemical-induced GAG depletion was a prominent decrease in Raman signal intensity at the 1000-1100 $cm^{-1}$ and 1200-1300 $cm^{-1}$ wavenumbers (FIG. 2.2$b$). Following multivariate regression analysis (equation 1), the Raman GAG score decreased in proportion to the reduction of GAG from the explants; the Raman scores for COL and $H_2O$ were less affected (FIG. 2.2$c$). The cumulative spectral contribution of the individual ECM constituents accounted for 94% of the variation of the composite cartilage spectra (FIG. 2.2$d$; $R^2$=0.94±0.01; $p<0.001$). The GAG scores predicted 95% of the variation in measured tissue GAG content (FIG. 2.2$e$; $R^2$=0.95; $p<0.001$; Table S1) and 75% of the variation in the measured compressive modulus ($E_Y$) for all explants (FIG. 2.2$f$; $R^2$=0.75; $p<0.001$), demonstrating the capacity of Raman spectroscopy to non-invasively predict progressive GAG and mechanical changes in hyaline cartilage material properties observed in early stage OA.

Raman Arthroscopy for Depth Selective Quantification

FIG. 2.3 shows Raman arthroscopy depth selective measurements. FIG. 2.3(*a*) shows lens-specific depth of penetration (DOP) based on measuring decay of polystyrene substrate Raman peak (988 cm$^{-1}$) intensity under variable cartilage thickness layers. DOP determined from cartilage thickness at which normalized peak decays to 37% of initial value (Beer-Lambert Law). FIG. 2.3(*b*) shows representative Safranin-O sections depicting trypsin-induced GAG depletion from the articular surface of cartilage explants. Scale bar=250 μm.

FIG. 2.3(*c*) shows bivariate linear regression between Raman arthroscopy-measured GAG scores and colorimetric Safranin-O-measured GAG content for deep focusing convex lens and surface-targeting ball lens.

The ball lens and convex lens exhibited different DOP values based on the Raman signal attenuation of polystyrene substrates under varying thickness cartilage layers (FIG. 2.3*a*). Cartilage explants exhibited progressive surface GAG depletion with increasing trypsin treatment time (FIG. 2.3*b*). Raman GAG scores deduced from Raman spectra obtained through the surface-targeting ball lens predicted 86% of the GAG tissue content (FIG. 2.3*c*; $R^2$=0.86; $p<0.001$; Table S2). However, Raman GAG scores deduced from spectra obtained through the deep focus convex lens, only predicted 40% of the GAG content ($R^2$=0.4; $p<0.001$; Table S2); GAG scores were influenced by residual GAG remaining in the deep zone, due to restricted diffusion of the GAG-depleting enzyme. These results show that Raman arthroscopy with a tight focusing lens is advantageous for quantification of early stage GAG depletion.

Raman Arthroscopy GAG Quantification in Human Explants

FIG. 2.4 shows Raman arthroscopy GAG measurements in human cartilage ex vivo. FIG. 2.4(*a*) shows representative Safranin-O histological sections of GAG-replete and GAG-depleted cartilage explants from human autopsy donors along with Raman GAG scores, GAG content, and SOFG stain uptake score. Scale bar=1 mm. FIG. 2.4(*b*) shows bivariate linear regression between Raman needle probe GAG scores (ball lens measured) and DMMB-measured GAG content of n=13 human explants ex vivo. FIG. 2.4(*c*) shows bivariate linear regression between Raman needle probe GAG scores (convex lens measured) and SOFG stain uptake scores. FIG. 2.4(*d*) shows representative radiographic and MRI sagittal plane images of arthritic hip joint, illustrating joint space narrowing at superior femoral head, corresponding to load bearing region of hip during standing. FIG. 2.4(*e*) shows GAG scores derived from multivariate Raman spectral decomposition acquired at discrete anatomic regions along a sagittal slice of a human femoral head articular joint surface ex vivo. GAG scores reflect depletion of GAG and cartilage thinning observed on MRI and histological section.

Human chondral explants exhibited a range of Safranin-O staining intensities and GAG contents (FIG. 2.4*a*). The ball-lens-acquired GAG scores predicted 66% of the variation of GAG content in the topmost 500 μm tissue layer (FIG. 2.4*b*; $R^2$=0.66; $p<0.001$; Table S3). Convex-lens-acquired GAG scores predicted 53% of the variation of a Safranin-O-Fast-Green (SOFG) stain uptake score (FIG. 2.4*c*; $R^2$=0.53; $p<0.01$; Table S3). Raman GAG scores were acquired at discrete anatomic sites along the articular surface of an excised human femoral head (FIG. 2.4*d-e*). Low Raman GAG scores were observed in the GAG-depleted hyaline cartilage, comprising the loaded region of the hip joint, while high GAG scores were observed in the GAG-replete hyaline cartilage comprising the unloaded region of the hip joint.

Polarized Raman Arthroscopy for Assessment of Zonal Collagen Alignment

FIG. 2.5 shows polarized Raman arthroscopy collagen alignment measurements. FIG. 2.5(*a*) shows mean polarized Raman spectra (perpendicular [colour lines] and parallel [black lines]) of cartilage with an intact SZ, mild abrasion and severe abrasion of the surface layer. FIG. 2.5(*b*) shows difference spectra of the polarization ratio (parallel/perpendicular) reveal differences in Raman spectra due to integrity of SZ collagen. FIG. 2.5(*c*) shows Partial least squares discriminant analysis (PLS-DA) scores showing good separation of the different erosion groups. FIG. 2.5(*d*) shows PLS-DA latent variable (LV) loadings LV1 and LV2. FIG. 2.5(*e*) shows Raman collagen alignment factor (RCAF) for detecting extent of SZ abrasion corresponding to LV2.

Consistent differences between the perpendicular and parallel polarization spectra were observed among the groups (no abrasion, mild abrasion, and severe abrasion) at Raman intensity peak positions highly associated with polarization sensitive collagen bands: 861, 930, 1257, 1448 and 1654 cm$^4$ (FIG. 2.5*a*). The depolarization ratio (i.e., difference intensity ratio between the perpendicular and parallel components of the Raman scattered light) revealed that differences in the polarized Raman spectra portrayed the varied zonal organization of the collagen fiber network (FIG. 2.5*b*). From PLS-DA, latent variable (LV) loadings LV1 and LV2 demonstrated good discriminatory separation among the abrasion groups (FIG. 2.5*c*) and incorporated diagnostically relevant spectral variations that reflected the integrity of the SZ collagen network (LV1:10.36% and LV2: 6.48%; FIG. 2.5*d*). Compared to LV1, LV2 better discriminated samples where the SZ was intact ($p<0.001$), therefore LV2 was used as a Raman collagen alignment factor (RCAF) to depict the extent that SZ collagen was retained (FIG. 2.5*e*). These results show that collagen alignment and SZ degeneration can be quantified by taking advantage of the polarization response of cartilage.

Raman arthroscopy cartilage thickness quantification FIG. 2.6 shows Raman arthroscopy cartilage thickness measurements. FIG. 2.6(*a*) shows a 2D stacked area graph showing contribution of GAG, COL, $H_2O$, and subchondral bone to composite Raman cartilage spectra after multivariate linear regression for osteochondral cartilage explants with a 0.3, 0.9, 1.5, and 2.1 mm thick cartilage layer. FIG. 2.6(*b*) shows bivariate regression between Raman arthroscopy measured subchondral bone score versus cartilage layer thickness.

Following multivariate regression analysis of the Raman spectra of variable thickness bovine osteochondral explants, the contribution of bone signal to the aggregate spectra decreased with increasing cartilage thickness (FIG. 2.6*a*). The regression coefficient for the subchondral bone contribution (bone score) to the cumulative Raman spectra varied inversely with thickness of the chondral layer, following an exponential decay function (FIG. 2.6*b*). The bone score predicted 90% of the variability in cartilage thickness. Hence, Raman spectroscopy offers an efficient method to quantify cartilage thickness changes that occur during OA associated tissue erosion.

Raman Arthroscopy In Situ and In Vivo Diagnostics

Assessments of potential confounding factors related to in situ Raman arthroscopy measurements demonstrated that: 1) The derived Raman GAG scores were insensitive to the presence of synovial fluid, 2) 20° variation from a normal (90°) probe incidence angle to the cartilage surface had no significant effect on measured Raman GAG and $H_2O$ scores ($p<0.05$), and 3) Integration time did not significantly affect Raman GAG, COL, and $H_2O$ scores due to the powerful features of multivariate analysis, indicating Raman arthroscopy measurements obtained in as little as 0.5 seconds will not compromise diagnostic capability. Further, for intra-articular Raman arthroscopy assessments on intact wrist joints, Raman GAG scores were reduced by 75% after trypsin treatment, corresponding to 86% reduction in cartilage GAG content: 4.3±0.6% ww control vs. 0.6±0.1% ww trypsin-treated tissue, thus demonstrating the ability of Raman arthroscopy to measure GAG in situ.

The distal femoral condyle articular cartilage of a live skeletally-mature sheep was accessed via a mini arthrotomy of the stifle joint (FIG. 2.1). The Raman needle probe was placed in gentle contact with the articular surface of the femoral condyle under image guidance. Raman spectra were acquired over a 10 second integration time to obtain the highest SNR for this in vivo demonstration. High quality Raman spectra were acquired in vivo (FIG. 2.1d), akin to ex vivo measures. The cumulative spectral contribution of the individual ECM constituents and subchondral bone derived by multivariate regression analysis accounted for 86% of the variation in the composite spectra (FIG. 2.1e; Raman scores: GAG=0.16, COL=0.58, $H_2O$=0.11, subchondral bone=0.10; $R^2$=0.86; $p<0.001$). This demonstration highlights the feasibility of in vivo Raman arthroscopy by demonstrating successful compositional quantification in vivo and the ability to manoeuvre the needle probe in a surgical setting.

Discussion

Early stage OA represents a critical clinical window when therapeutic strategies will be most effective in mitigating cartilage degeneration. However, the ability to diagnose OA early, before irreparable changes in tissue composition and structure ensue, remains a significant clinical challenge and hinders effective developments of therapeutics. We present a needle-based arthroscopic platform for achieving real-time, polarized Raman spectroscopy quantification of changes in cartilage ECM associated with early stage OA. Using both ex vivo bovine models of OA and aging human cartilage explants, we demonstrate that Raman needle arthroscopy accurately can quantify SZ cartilage GAG depletion and collagen disorganization responsible for the degradation in hyaline cartilage material behaviour. A critical innovation, described herein, is the implementation of multivariate regression to ascertain the contribution of individual spectra corresponding to the ECM constituents GAG, COL, and $H_2O$ to the cumulative Raman cartilage spectra. The derived regression coefficients (GAG scores) account for 95% of the variation of the GAG content of enzymatically depleted bovine explants, and 66% of the variation in the GAG content and 53% of the variation in SOFG staining score of human chondral explants. Additionally, the derived Raman $H_2O$ and COL scores portray damage to the integrity of the tensile collagen matrix that give rise to cartilage swelling in early stage OA.

To further evaluate the zone-dependent, anisotropic microstructure of the collagen matrix, we incorporate polarized Raman spectra into our platform to exploit differences between the perpendicular and parallel polarization spectra. This novel functionality, achieved by tightly focusing the distal ball lens to avoid bulk tissue polarization scrambling, enables assessment of the alignment and organization of the SZ collagen matrix. To maximize diagnostically relevant spectral variations that reflect the integrity of the SZ collagen, PLS-DA was applied to the spectral data, giving rise to latent variables (LV1, LV2) that incorporated Raman intensity peak positions highly associated with polarization sensitive collagen bands. LV2 efficiently discriminates an intact SZ and can therefore be used as an alignment factor to depict the extent that SZ collagen was retained.

While the diagnosis of early OA GAG and collagen loss requires utilization of a ball lens with tight focus that collects Raman signal predominantly from the topmost cartilage regions, Raman cartilage thickness measurements require a deep focusing lens to collect sufficient Raman signal from the subchondral bone. Thus, the lens configuration selected depends on the diagnostic metric to be quantified. In this study, to resolve Raman-based cartilage thickness, we used a large, non-needle-based lens to target the subchondral bone. In future iterations of our device, an interchangeable deep tissue lens (hemispherical lens or custom manufactured high DOP micro lens) will be incorporated into the needle probe.

To demonstrate the feasibility of translating Raman needle arthroscopy to the clinic as a novel point-of-care platform, we acquired high quality Raman spectra of articular cartilage comprising the ovine femoral condyle in vivo that were similar to ex vivo assessments. Clinical translation is further supported by establishing: 1) Raman spectra can be obtained in as little as 0.5 seconds, 2) the derived Raman GAG scores are insensitive to the presence of synovial fluid, and 3) the probe incidence angle can vary up to 20° from normal to the cartilage surface without compromising diagnostic accuracy. Further, in situ intra-articular Raman spectra acquired on intact bovine diarthrodial joints before and after enzymatic-induced degradation validated that Raman GAG scores were consistent with measured GAG content.

There has been growing interest in Raman spectroscopy as a potential OA diagnostic technology. Prior ex vivo work has examined Raman spectral changes in explanted late stage OA cartilage tissues or cartilage subjected to mechanical damage. With the exception of Unal et al., who used high-wavenumber Raman peak ratios to measure cartilage water content but not GAG or collagen, prior Raman assessments have consisted of univariate peak analysis or principle component analysis (PCA), which do not provide quantification of biochemical or structural tissue changes relevant to the tissue's functional performance. Further, with the exception of Esmonde-White et al., which used a probe to measure cartilage erosion, previous Raman investigations have been performed on benchtop microscopy systems that are incompatible with in situ intra-articular Raman evaluations. Our study represents the first in vivo Raman diagnostic investigation to utilize a clinically compatible needle arthroscopy probe to measure the pathognomonic changes of early stage OA: superficial region GAG depletion and SZ collagen loss.

Our Raman needle arthroscopy platform complements and exceeds other state-of-the-art OA diagnostic platforms (MRI (T1ρ, dEGEMRIC), ultrasound, contrast enhanced CT, OCT) in portraying changes in cartilage composition, structure, and material properties. While these imaging modalities are non-invasive and can image the entire joint, they are limited by spatial resolution of the cartilage surface, systemic administration of potentially toxic contrast agents, extended imaging times, expense, lack of portability, and infrastructure requirements. Owing to its portability, Raman needle arthroscopy can serve as a transformative platform that achieves rapid, easy-to-implement, real-time assessments of the key compositional and structural features of hyaline cartilage responsible for its functional performance without patient exposure to radiation or toxic contrast agent.

Clinically, we envision Raman needle arthroscopy to be performed as a point-of-care office procedure in combination with other intra-articular procedures, such as synovial fluid aspiration or drug infusion. The platform can achieve targeted anatomical site-specific assessments through interfacing with arthroscopy image guidance (e.g., Arthrex NanoScope). As a point-of-care platform, Raman arthroscopy provides a cost-effective method to identify early stage cartilage degeneration in patient populations known to be at high risk for developing OA as a consequence of acute or chronic traumatic joint injury, internal derangement, obesity, joint malalignment, and genetic predisposition. The periodic monitoring of commonly affected joints (knee, hip, shoulder, elbow, ankle) may allow for the timely prescription of chondroprotective therapies, such as biologics (e.g., growth factors, platelet-rich plasma), viscosupplements (hyaluronan, synthetic lubricin), lifestyle changes (weight loss, activity cessation), physical therapy, or surgical reconstruction (joint realignment), as well as microfracture, autologous cell implantation, or graft implantation to reconstitute irreparable hyaline cartilage. Through assessment of developing GAG deposition and collagen matrix organization, Raman arthroscopy enables objective monitoring of treatment outcomes. In addition to clinical diagnostics, Raman arthroscopy can serve as a research tool, evaluating the efficacy of emerging therapeutics in pre-clinical animal models. In conclusion, Raman arthroscopy is a practical, minimally invasive, point-of-care, clinical tool capable of diagnosing OA before irreparable changes in cartilage biochemical and biophysical properties are evident radiographically, a requisite for the effective implementation of OA treatments.

2. Raman Plate Reader for Quantitative Molecular Monitoring of Live Cartilage Explants Overview Embodiments of the invention described in this section below are directed to a high-throughput Raman plate reader to non-invasively monitor compositional changes in live cartilage specimens over time. Described below are a long-distance focusing Raman probe and a Raman-compatible tissue culture chamber to achieve in situ Raman measurements on explant specimens while they are maintained in culture. In more detail, we describe below an ex vivo Raman plate-reader for assessments of the composition of live tissues. The Raman plate reader can serve as a high-throughput, non-destructive platform to monitor the composition of musculoskeletal connective tissue explants (e.g. cartilage, meniscus, tendons, ligaments, intervertebral disk) and cultured engineered tissues over time. This platform has outstanding utility for studying tissue behaviour in response to mechanochemical stimuli, mechanisms of pathologic tissue degeneration, and the efficacy of therapeutics to inhibit or reverse degeneration, and the development of engineered tissues.

Introduction

Figure 3A:
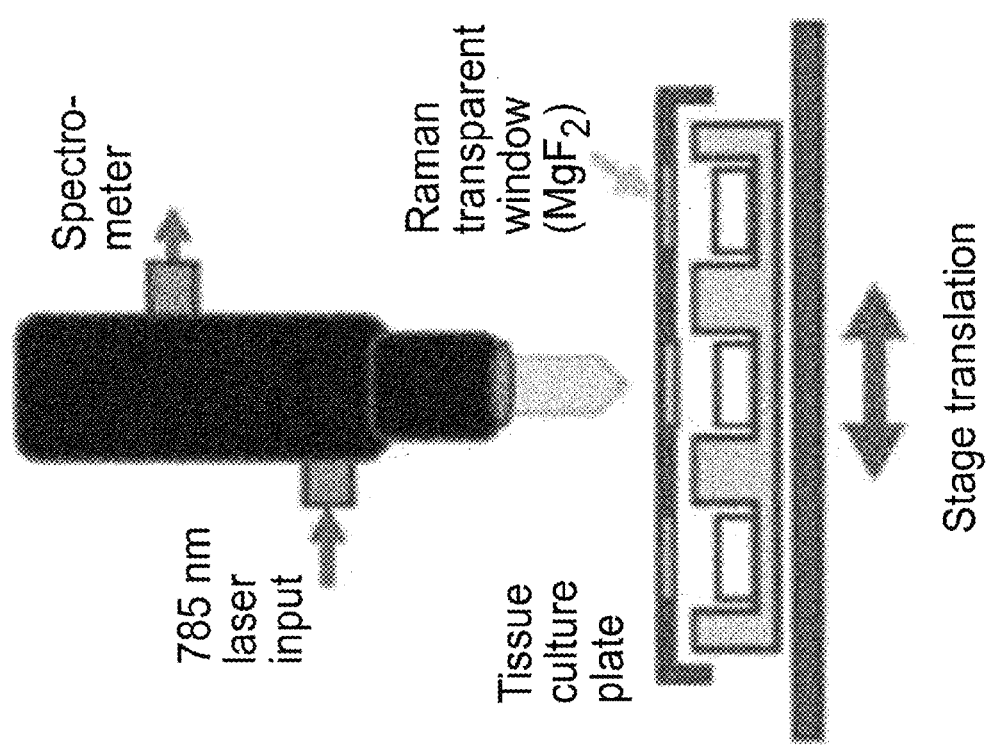
FIG. 3A shows a Raman plate reader for monitoring composition of live cartilage explants in culture.
Figure 3B:
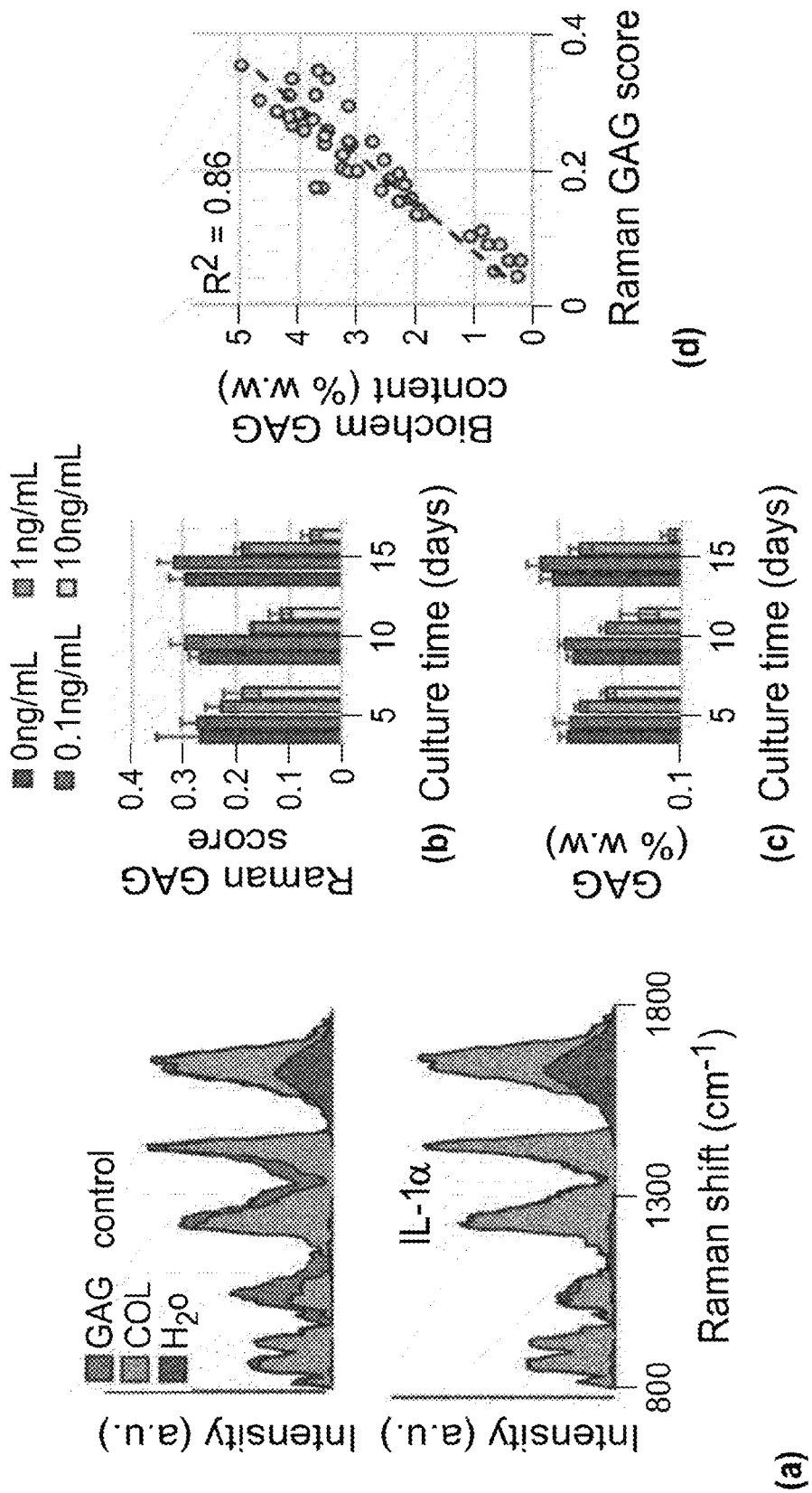
FIG. 3B shows: (a) Representative 2D stacked area plot of spectral contribution of GAG, COL, H2O to cartilage Raman spectra with or without IL-1α treatment at day 15 (b) Raman GAG scores and (c) assay-measured GAG content of explants treated with varying dose/duration regimens of IL-1α. (d) Linear correlation between Raman GAG score and GAG content of IL-1α-treated explants.
Figure 3C:
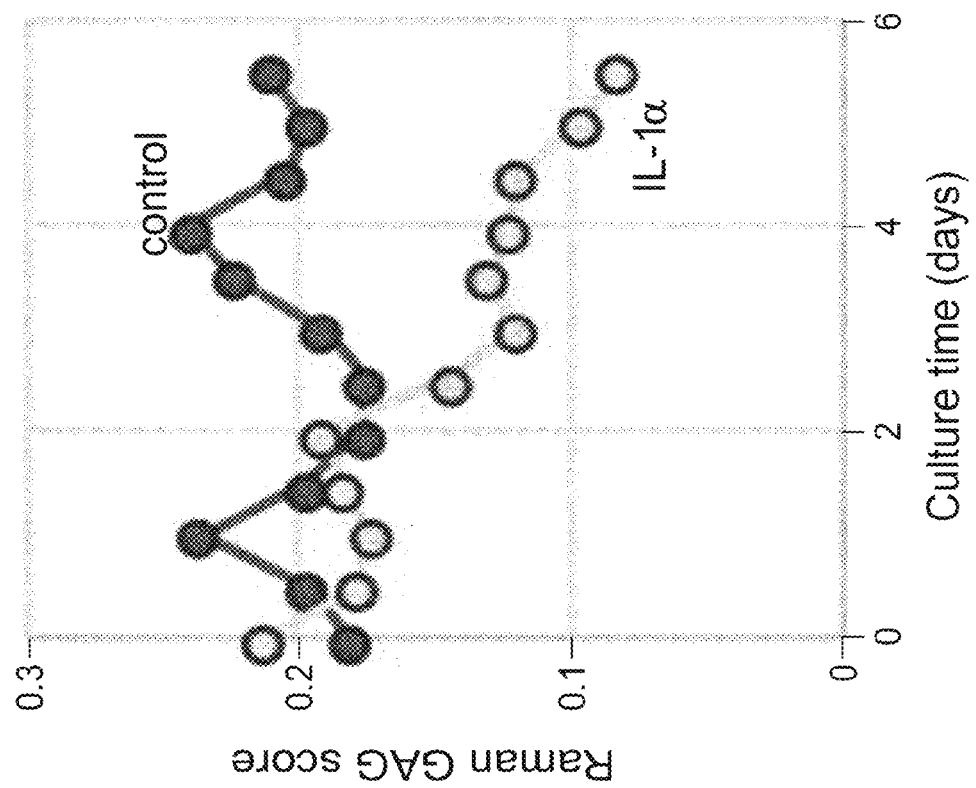
FIG. 3C shows a Raman plate reader repeated-measured GAG scores of live explants treated with or without IL-1α over 6 days.
Figure 4A:
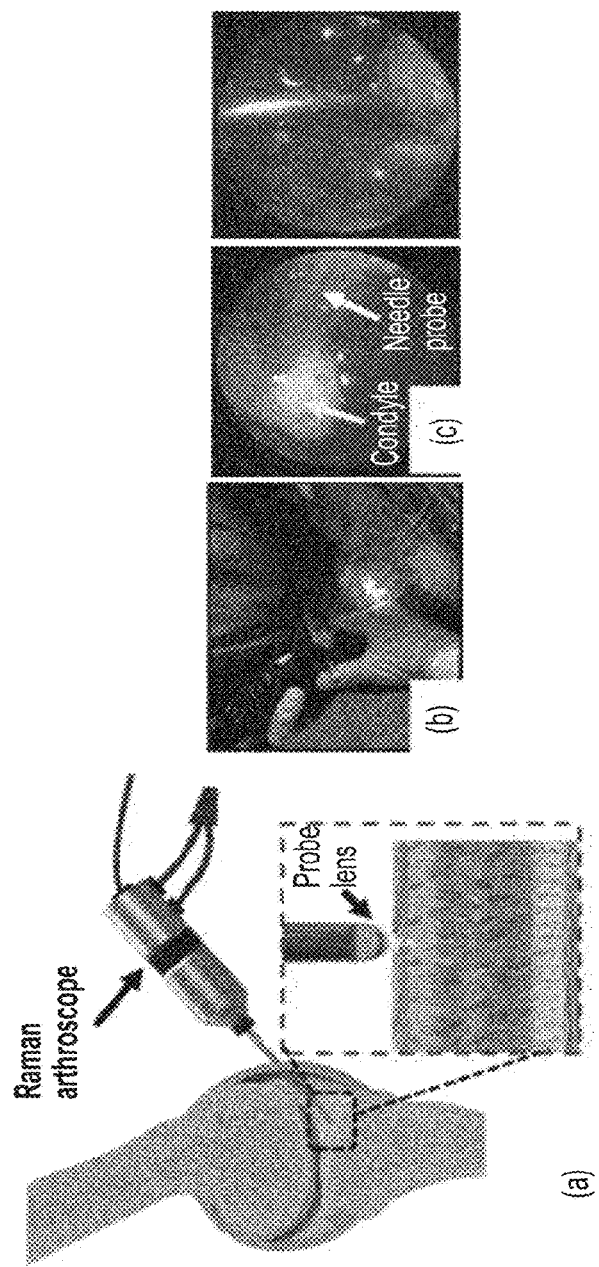
FIG. 4A shows: (a) Schematic of Raman needle arthroscope for degeneration diagnostics. (b) In vivo Raman assessment of ovine stifle joint. (c) Raman probe in direct contact with femoral condyle as visualized by arthroscopic camera. (d) Raman spectra acquired in vivo of ovine femoral condyle. (e) 2D stacked area graph showing contribution of GAG, COL, H2O, and subchondral bone to composite ovine cartilage Raman spectra after multivariate linear regression.
Figure 4A:
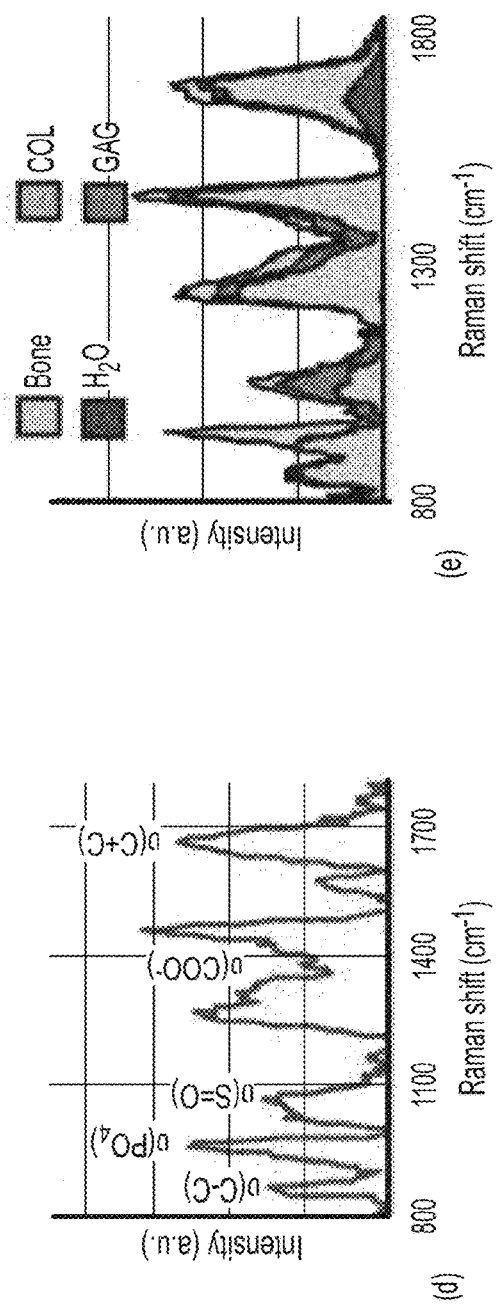
Figure 4B:
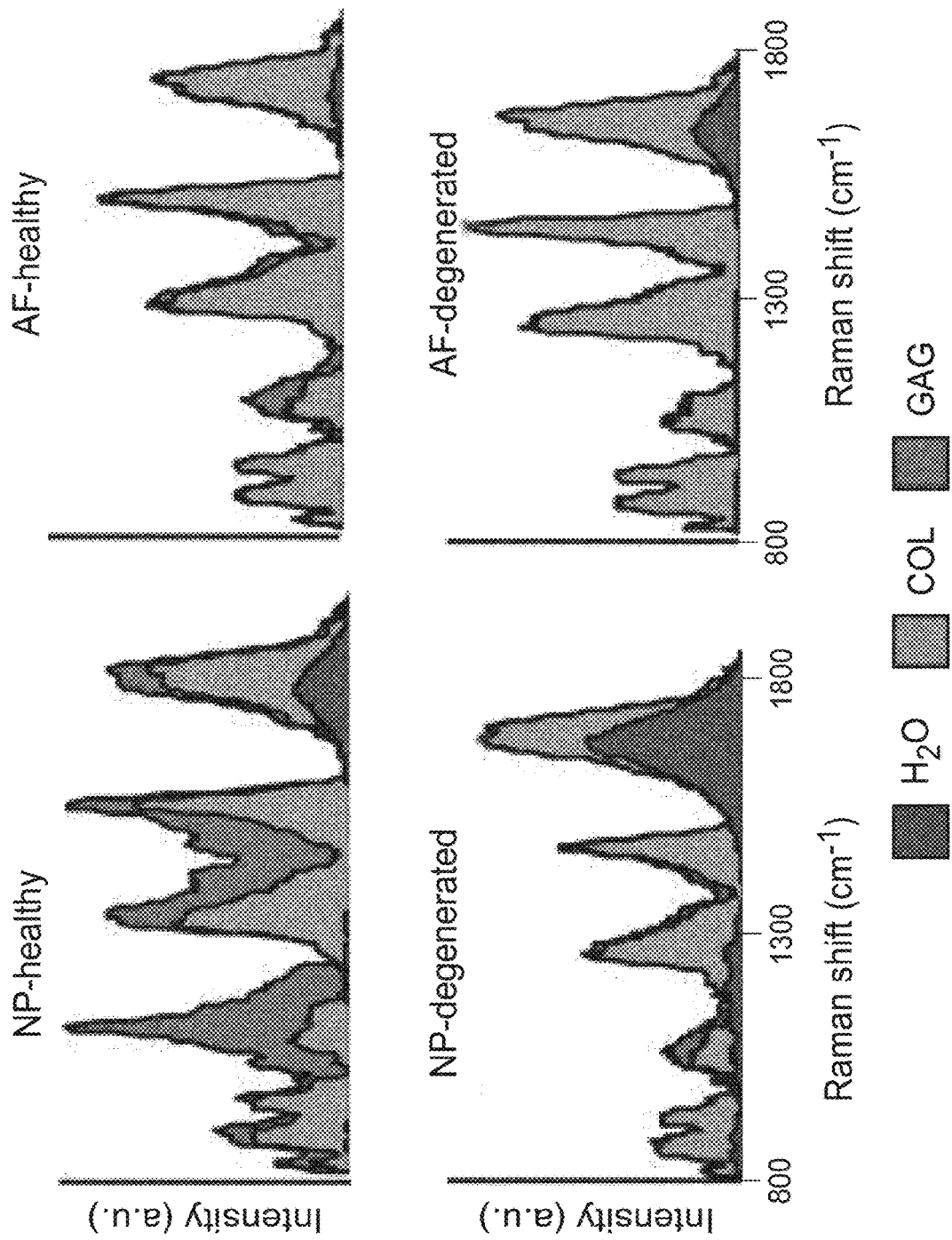
FIG. 4B shows a 2D stacked area graph of GAG, COL, H2O contribution to IVD Raman spectra in nucleus pulposus (NP) and annulus fibrosus (AF) of IVD before and after degeneration.
Figure 4C:
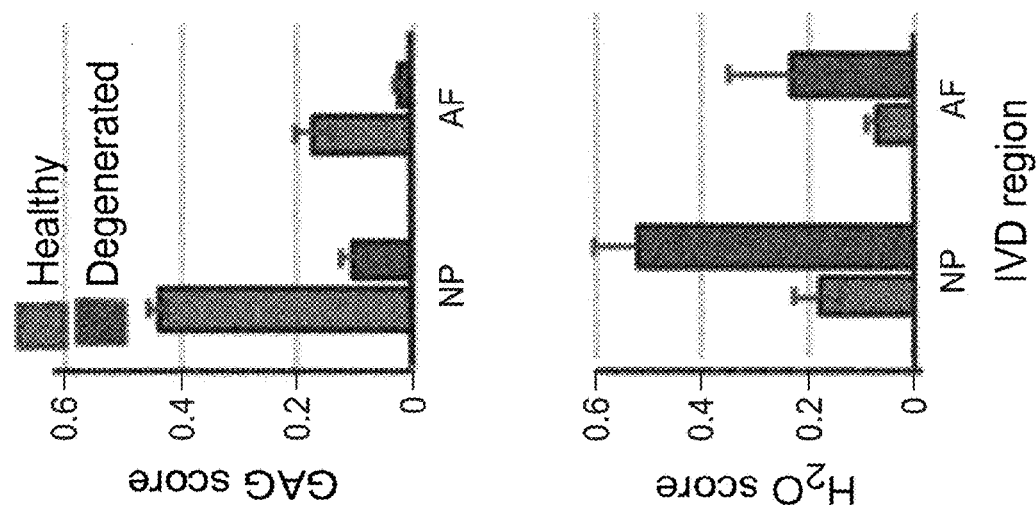
FIG. 4C shows Raman GAG and H2O scores of NP and AF before and after degeneration.

The cultivation of live explanted cartilage tissues ex vivo has long served as an important platform for studying tissue behaviour in response to mechanochemical stimuli, providing insights into cartilage regulatory mechanisms, osteoarthritis progression, and the efficacy of emerging therapeutics. Cartilage assessments focus predominantly on measures of compositional changes of the major ECM constituents in cartilage that give rise to the load supporting, low friction mechanical functionality of the tissue: collagen (COL), glycosaminoglycans (GAG), and water. Conventionally, ECM composition is assessed via biochemical assays, notably the DMMB assay for GAG, OHP assay for COL, and gravitational weight measures for water content. However, biochemical assays invoke considerable study limitations: they are 1) time intensive—requiring laborious sample processing and 2) sample destructive—thus preventing repeated measure assessments of cartilage compositional changes over time. Raman spectroscopy is an inelastic light scattering technique that provides an optical fingerprint of a tissue specimen that reflects specific molecular building blocks (amides, sulfates, carboxylic acids, hydroxyls). Above, we demonstrated that a novel Raman arthroscopic probe and multivariate statistical regression models can be used to predict the chemical composition (GAG, COL, $H_2O$) of devitalized cartilage explants with exceptional accuracy, evidenced by near unity correlation coefficients ($R^2$=0.95) between Raman metrics and GAG content. In the current study, we develop a novel high-throughput Raman plate reader to non-invasively monitor compositional changes in live cartilage specimens over time (FIG. 3.1). Here, we introduce a long-distance focusing Raman probe and a Raman-compatible tissue culture chamber to achieve in situ Raman measurements on explant specimens while they are maintained in culture. Our Raman plate reader can achieve high throughput, repeated measures of cartilage composition, allowing for longitudinal monitoring of cartilage explant ECM changes in response to mechanochemical stimuli. Here, we examine the sensitivity of our Raman plate reader by comparing endpoint Raman assessments to direct biochemical assay measures of explants exposed to the osteoarthritis-associated catabolic cytokine interleukin-1α (IL-1α). Subsequently, we perform repeated-measure Raman compositional monitoring on live explants exposed to IL-1α with high temporal-resolution (every 12 hours).

Method

Tissue Source

Live cartilage disks (Ø5×1 mm) were harvested from immature bovine femoral condyles and maintained in a low Raman interference phenol-red-free DMEM supplemented with L-glutamine, L-proline, antibiotic/antimycotic, and 10 nM dexamethasone.

Raman Monitoring Platform

Our custom Raman plate reader consists of an NIR diode laser ($\lambda_{ex}$=785 nm, 500 mW, B&W Tek) and a fiber-coupled spectrograph (QEPro, Ocean Optics). The distal part of the probe consists of a long-distance plano-convex lens (N-BK7, Ø9 mm, 10 mm focal length) that achieves a ~540 μm depth of penetration into cartilage. Explants were maintained in a modified 96-well polystyrene plate chamber to allow for Raman acquisitions without plastic interference while cartilage explants remain in culture. Here, a Raman transparent $MgF_2$ window was inserted in a cut-out in the plate lid and a thin aluminium disk was inserted below each explant (FIG. 3.1). Raman spectra of cartilage explants were acquired (10 s acquisition time) through the $MgF_2$ window and subjected to pre-processing. Raman spectra (fingerprint range) were subjected to multivariate linear regression, using the following model:

$$\text{Cartilage}_{spectra} = \text{GAG}_{score} * (\text{GAG}_{REF}) + \text{COL}_{score} * (\text{COL}_{REF}) + \text{H2O}_{score} * (\text{H2O}_{REF}) \tag{1}$$

where $GAG_{REF}$, $COL_{REF}$, $H2O_{REF}$ are the component spectra of purified reference chemicals, used to extract the regression coefficients or "scores" that reflect the contribution of the spectra of each constituent element.

Raman-Biochemical Correlation

Explants were exposed to IL-1a at 0, 0.1, 1, or 10 ng/mL for 5, 10, or 15 days of culture. At culture completion, a central Ø3 mm subcore of each explant was subjected to Raman plate reading and GAG content measures (DMMB assay).

Repeated-Measure Live Cartilage Raman Monitoring

Live explants were maintained in the Raman monitoring plate throughout culture and treated with or without 10 ng/mL IL-1α. At 12 h intervals over a 6-day period, plates were briefly removed from the incubator and each explant specimen was subjected to Raman plate reading.

Results

Raman-Biochemical Correlation

Multivariate regression models were able to describe the measured cartilage Raman spectra-cumulative contribution of the individual ECM constituents accounted for 87% of the variation of the composite cartilage spectra. Raman GAG scores decreased with IL-1α exposure, decreasing with dose and culture time (FIG. 3.2a-b). Raman COL scores exhibited a modest increase with IL-1α treatment and $H_2O$ scores were relatively unaltered (not shown). Similarly, assay-measured GAG content decreased with IL-1a dose and culture time (FIG. 3.2c). Raman GAG score predicted 86% of the variation in assay-measured GAG content (FIG. 3.2d; $R^2=0.86$; $p<0.001$).

Repeated-Measure Live Cartilage Raman Monitoring

In the absence of IL-1α, cartilage explants maintained near-constant Raman GAG scores over 6 days. In response to IL-1α, Raman GAG scores decreased by 61% over 6 days (FIG. 3.3). No viability loss (Live-Dead imaging) was observed in either group after 6 days.

Discussion

This study demonstrates the ability of our Raman plate reader platform to perform accurate, non-destructive, repeated-measure monitoring of the ECM composition of live explanted cartilage specimens. Through the development of a novel long-range Raman probe and compatible testing chamber, we can obtain high quality Raman spectra of live cartilage explants while maintaining them in their culture plate, thus allowing for rapid, easy-to-acquire compositional assessments without risking tissue contamination or viability loss. In the future, we aim to interface our Raman plate reader with an automated 2D translation stage and GUI, allowing for high-throughput monitoring (96 explants in ~2 min), akin to an absorbance/fluorescence microplate reader. A further critical innovation is the implementation of multivariate regression analysis to ascertain the contribution of individual spectra corresponding to ECM constituents GAG, COL, and $H_2O$ to the cumulative Raman spectra. Accordingly, our Raman plate reader can monitor the key compositional changes associated with cartilage degeneration, notably GAG depletion and increased hydration from tissue swelling. Here, we demonstrate the ability of our Raman plate reader to monitor GAG loss in response to the osteoarthritis-associated catabolic cytokine IL-1α. Raman GAG scores account for 86% of the variation of GAG content in IL-1α degenerated cartilage, thus establishing the platform's ability to robustly monitor tissue degeneration.

Significance

Our novel Raman plate reader can serve as a high-throughput, non-destructive platform to monitor the composition of musculoskeletal connective tissue explants (cartilage, meniscus, tendons, ligaments, intervertebral disk) over time. This platform has outstanding utility for studying tissue behaviour in response to mechanochemical stimuli, mechanisms of pathologic tissue degeneration, and the efficacy of novel therapeutics.

FIG. 3.1 shows a Raman plate reader for monitoring composition of live cartilage explants in culture.

FIG. 3.2 shows: (a) Representative 2D stacked area plot of spectral contribution of GAG, COL, $H_2O$ to cartilage Raman spectra with or without IL-1α treatment at day 15 (b) Raman GAG scores and (c) assay-measured GAG content of explants treated with varying dose/duration regimens of IL-1α. (d) Linear correlation between Raman GAG score and GAG content of IL-1α-treated explants.

FIG. 3.3 shows a Raman plate reader repeated-measured GAG scores of live explants treated with or without IL-1α over 6 days.

3. Raman Needle Arthroscopy for In Vivo Diagnostics of Musculoskeletal Connective Tissues Overview Embodiments of the invention described in this section below are directed to in vivo diagnostics of musculoskeletal connective tissues including measurements of GAG/water content in the intervertebral disk (for disk degeneration diagnostics).

Introduction

Connective tissue degenerative disorders, such as osteoarthritis ([OA]-characterized by degradation of articular cartilage) and degenerative disc disease (degradation of the intervertebral disc [IVD]), are painful, highly debilitating conditions that impact a large and growing percentage of the adult population. There is a growing viewpoint that early stages of disease progression, before substantial tissue breakdown has transpired represent a critical clinical window when therapeutics may be most efficacious. However, the ability to diagnose early stage tissue degeneration remains a significant clinical challenge; state-of-the-art imaging modalities (e.g., CT, MRI) are predominantly sensitive for diagnosing late stage degeneration after irreversible changes in tissue composition have occurred-worsening prognosis and limiting treatment options. Raman spectroscopy is an inelastic light scattering technique with exceptional potential for diagnosing tissue compositional changes by providing a highly quantitative optical fingerprint that reflects specific molecular building blocks (amides, sulfates, carboxylic acids, hydroxyls) in a tissue specimen. Recently, we developed a novel Raman arthroscopic platform to diagnose compositional changes associated with early connective tissue degeneration. The platform includes: 1) a Raman probe that can achieve intra-articular tissue assessments through a hypodermic needle cannula, and 2) the implementation of multivariate regression statistical models extracts measures of tissue biochemical composition (GAG, collagen, water), enabling assessments of early degeneration GAG depletion and tissue swelling. In ex vivo models we have demonstrated the capability of Raman arthroscopy to predict early-OA-associated GAG depletion in articular cartilage with outstanding accuracy, marked by predicting 95% of the variation of GAG content in enzymatically-depleted cartilage explants. In the current study, we aim to significantly advance this platform by examining: 1) the feasibility of performing Raman diagnostic measurements in vivo, and 2) the feasibility of performing Raman diagnostics on additional connective tissue systems. Here, in vivo assessments are performed on the articular cartilage of the distal femur in a sheep. Expanded tissue assessments are performed ex vivo on IVDs of sheep at different anatomical regions and in response to degenerative treatments.

Methods

Raman Arthroscope

Our custom Raman needle arthroscope for intra-articular entry through a hypodermic needle (FIG. 4.1a) consists of an NIR diode laser ($\lambda_{ex}$=785 nm, 500 mW, B&W Tek) and a fiber-coupled spectrograph (QEPro, Ocean Optics). Laser light is directed through the distal part of the probe through the needle probe (ø=2 mm, 1=50 mm) and tightly focused onto the tissue using a 2.0 mm sapphire ball lens.

Spectral Processing

After pre-processing, Raman spectra were subjected to multivariate linear regression, using the following model:

$$Cartilage_{spectra}=GAG_{score}*(GAG_{REF.})+COL_{score}*(COL_{REF})+H2O*(H2O_{REF})+Bone_{score}*(Bone_{REF})$$

where $GAG_{REF}$, $COL_{REF}$, $H_2O_{REF}$, $Bone_{REF}$ are the component spectra of purified reference chemicals or subchondral bone (bovine source), used to extract the regression coefficients or "scores" that reflect the contribution of the spectra of each constituent element.

In Vivo Cartilage Arthroscopy

The distal femoral condyle articular cartilage of a live skeletally-mature sheep was accessed via a mini arthrotomy of the stifle joint (FIG. 4.1b-c). The Raman needle probe was placed in gentle contact with the articular surface of the femoral condyle under image guidance. Raman spectra were acquired over a 10 s integration time to obtain the highest SNR for this in vivo demonstration.

Ex Vivo IVD Diagnostics

L-spine IVDs were isolated from skeletally-mature sheep. Raman measurements were performed at 5 discrete points within the nucleus pulposus (NP) and annulus fibrosus (AF) of one freshly excised IVD and an IVD subjected to degeneration. Degeneration consisted of an 18 h incubation in PBS supplemented with 2 mg/mL trypsin, which induced a combination of swelling and GAG depletion, akin to compositional changes during IVD degeneration pathology. After Raman acquisitions, discrete Ø2 mm cylindrical cores of IVD specimens were assessed for GAG and water contents.

Results

In Vivo Cartilage Arthroscopy

Through a mini arthrotomy, we were able to acquire high quality in vivo Raman spectra (FIG. 4.1d), akin to those from our prior work ex vivo. The cumulative spectral contribution of the individual ECM constituents and subchondral bone derived by multivariate regression analysis accounted for 86% of the variation in the composite spectra (FIG. 4.1e), yielding Raman scores of GAG=0.16, COL=0.58, $H_2O$=0.11, subchondral bone=0.10; $R^2$=0.86; p<0.001), consistent with prior ex vivo measures on healthy articular cartilage specimens.

Ex Vivo IVD Diagnostics

Relative to the AF, the NP exhibited higher GAG (NP: 7.3±0.9% ww vs AF: 4.0±0.4% ww) and water (NP: 84.3±7.7% ww vs AF: 70.9±2.5% ww) content. Degeneration treatment decreased GAG content in the NP (0.90.1% ww) and AF (1.2±0.6% ww), and increased water content in the NP (95.3±1.0% ww) and AF (80.5±2.4% ww). The cumulative spectral contribution of the ECM constituents by multivariate regression accounted for 77% of the variation in the IVD composite spectra (FIG. 4.2) (p<0.01). Raman scores reflected the biochemical composition of the IVD, as marked by: 1) higher Raman GAG and $H_2O$ scores for NP relative to AF, and 2) decreased GAG scores and increased $H_2O$ scores in both the NP and AF with degeneration (FIG. 4.3).

Discussion

We present a novel, needle-based arthroscopic platform for achieving real-time, Raman-based diagnostics of the compositional changes associated with musculoskeletal connective tissue degeneration. Building upon our recent ex vivo characterizations, we now demonstrate the feasibility of translating Raman needle arthroscopy to the clinic by acquiring high quality Raman spectra of ovine femoral condyle articular cartilage in vivo. Further, the performance of IVD Raman measures demonstrates the feasibility of expanding Raman diagnostics towards connective tissues beyond articular cartilage. Here we show that Raman arthroscopy can readily distinguish the GAG and water composition between the NP and AF of the IVD, and between health and degeneration. Clinically, Raman needle arthroscopy can serve as quantitative adjunct to current joint arthroscopy for assessment of tissue degeneration and response to treatments. For articular cartilage, Raman arthroscopy can guide the timely prescription of chondroprotective therapies, such as biologics, viscosupplements, lifestyle changes (weight loss, activity cessation), physical therapy, or surgical reconstruction. For the IVD, Raman arthroscopy provides a method to extend discography to assess composition before and after treatment with injection of large molecular weight aggrecans to augment and reconstitute the GAG-depleted NP.

Significance

Raman arthroscopy can serve as a transformative diagnostic platform, offering quantitative assessments of the critical compositional tissue changes in the early stages of tissue degeneration. Raman arthroscopy can serve as: 1) a valuable clinical/pre-clinical research tool to advance the development of novel therapeutics, and 2) a clinical diagnostic platform to guide treatment courses.

FIG. 4.1 shows: (a) Schematic of Raman needle arthroscope for degeneration diagnostics. (b) In vivo Raman assessment of ovine stifle joint. (c) Raman probe in direct contact with femoral condyle as visualized by arthroscopic camera. (d) Raman spectra acquired in vivo of ovine femoral condyle. (e) 2D stacked area graph showing contribution of GAG, COL, $H_2O$, and subchondral bone to composite ovine cartilage Raman spectra after multivariate linear regression.

FIG. 4.2 shows a 2D stacked area graph of GAG, COL, $H_2O$ contribution to IVD Raman spectra in nucleus pulposus (NP) and annulus fibrosus (AF) of IVD before and after degeneration.

FIG. 4.3 shows a Raman GAG and H$_2$O scores of NP and AF before and after degeneration.

4. Raman Needle Probe Monitoring of Engineered Cartilage Growth

Overview

In this section, the application of the Raman probe system to measurements of the growth of engineered cartilage tissues (i.e. biomolecular synthesis) is described with reference to FIG. 5. Here, immature bovine chondrocytes were seeded in agarose hydrogel scaffolds and cultivated in chondrogenic medium in the absence or presence of 10 ng/mL TGF-beta3 (administered for initial 2 weeks). After 0, 14, 28, 42, 56 days of culture, explants were subjected to Raman probe measures and DMMB biochemical assay GAG measures. Spectra were proceed via previously described multivariate linear regression using reference chemicals of agarose, chondroitin sulfate, type-II collagen, and water.

Figure 5:
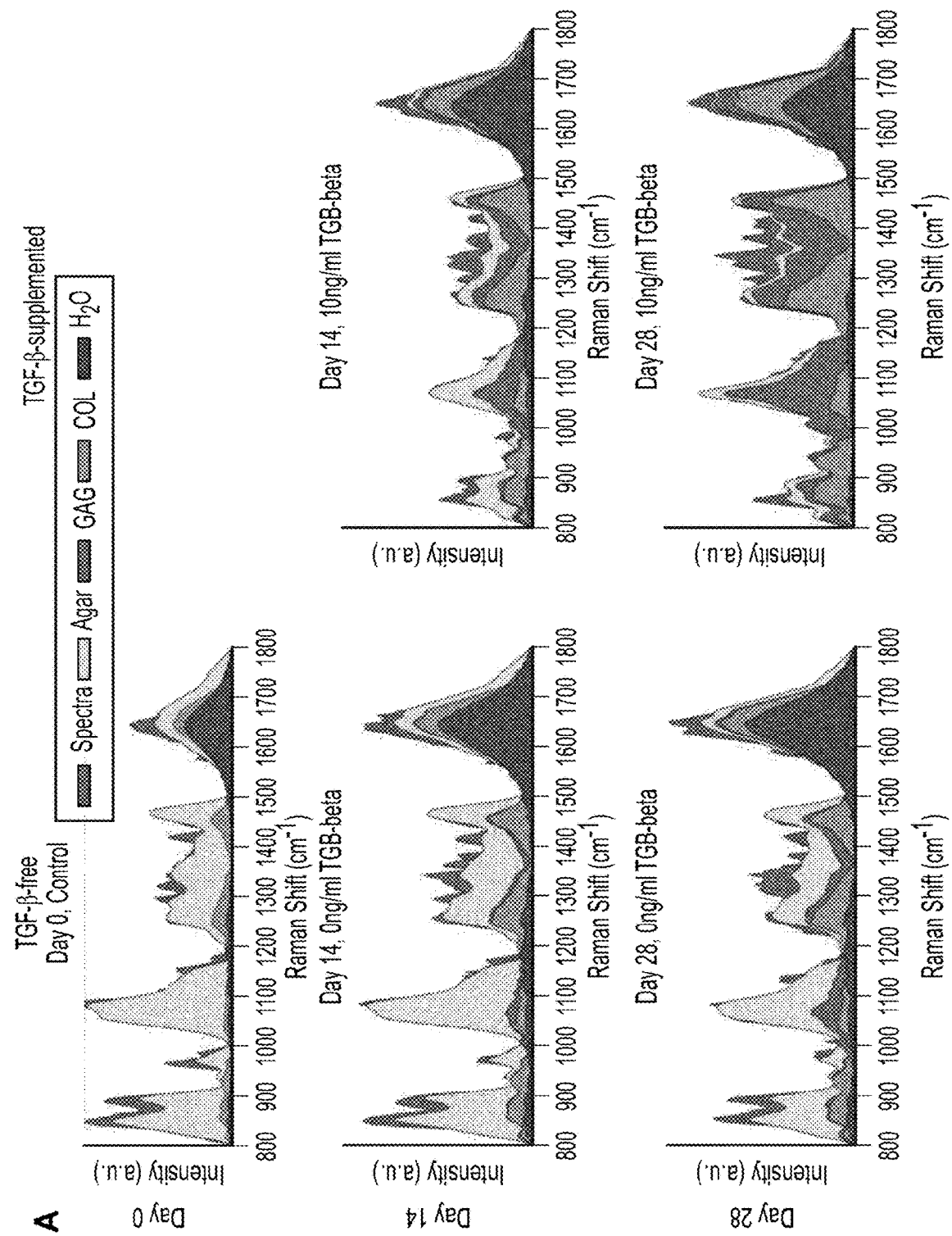
FIG. 5 shows Raman needle probe monitoring of engineered cartilage growth.
Figure 5:
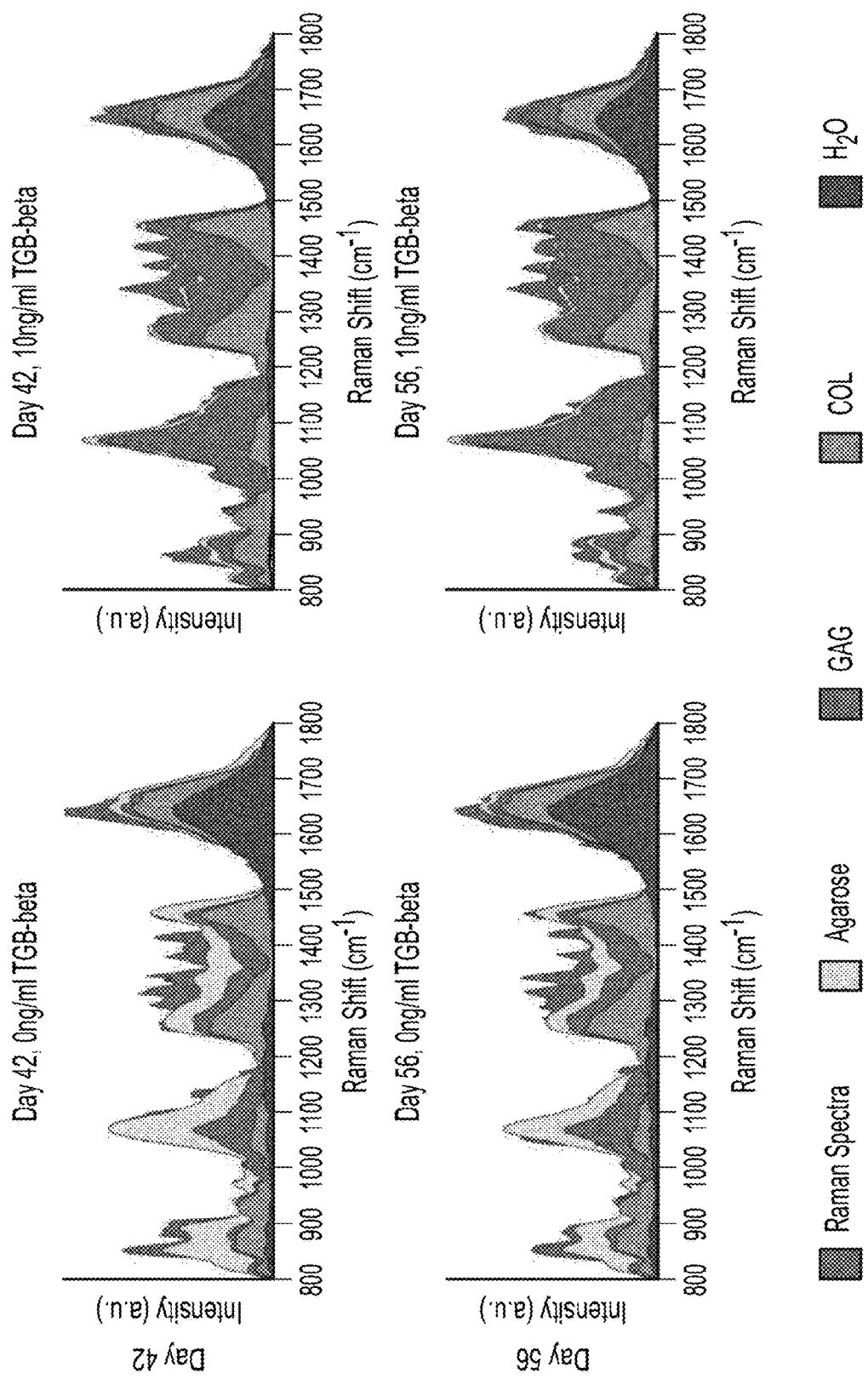
Figure 5:
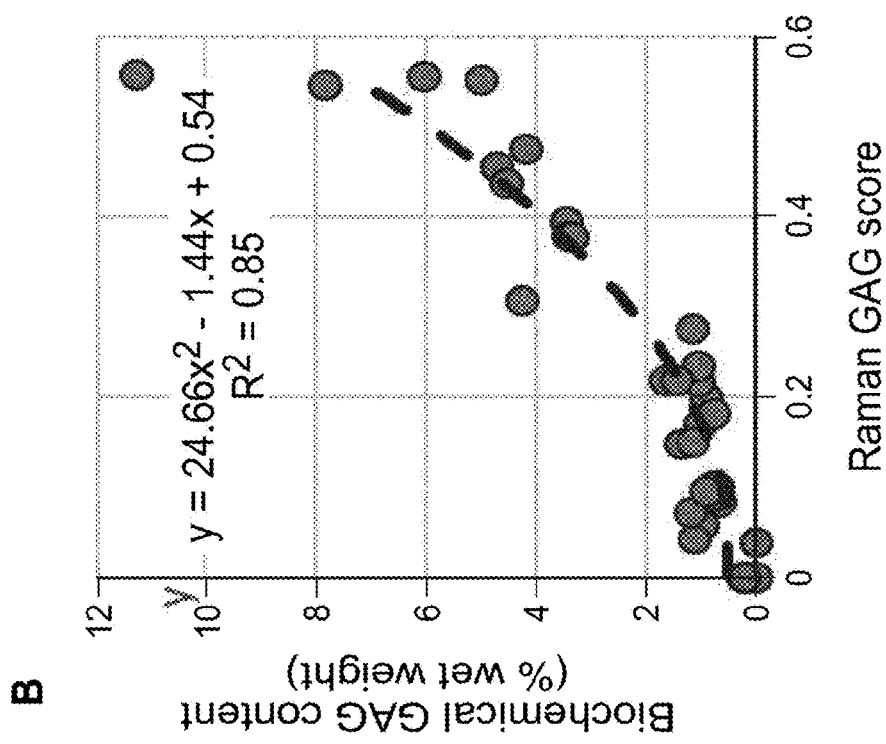

FIG. 5 shows Raman needle probe monitoring of engineered cartilage growth. FIG. 5(A) shows 2D stacked area plots depicting representative contribution of agarose scaffold, glycosaminoglycans (GAG), collagen (COL), and water (H$_2$O) to Raman spectra of engineered cartilage constructs after multivariate regression analysis. FIG. 5(B) shows bivariate correlation between Raman GAG scores and biochemical assay measured GAG content in engineered cartilage constructs. Raman probe can predict characteristic elevated in engineered cartilage GAG content over time and with the supplementation of anabolic growth factor TGF-β.

5. Multiplexed Polarized Raman Spectroscopy for Diagnosis of Oral Cancers

Overview

In this section, applications of methods and systems described above to identifying cancerous tissue are described.

Background

Oral cancers are severe life-limiting diseases, particularly when discovered in the later stages. Early detection in precancerous or early cancer stages (i.e., carcinoma in situ) is among the most important measures for reducing morbidity and mortality rates in oral cancer patients. Conventional diagnosis relies on gross inspection and biopsy of the oral cavity which has resulted in 5 year survivals of up to 90% for early tumors. This survival rate however declines to 50% for advanced cancers, highlighting the necessity of early diagnosis as a primary factor in determining patient outcomes. Conventional diagnosis based on visual inspection suffers from inter-observer dependence and an inherent inability to reveal biomolecular or microscopic information about the tissue. Tumor depth, local/distant spread assessment (staging) and grading (aggression), and margin assessment of cancer lesions also represent major challenges to selecting appropriate treatment or surveillance strategies. Taking into account these existing clinical challenges, it is highly desirable to develop minimally invasive diagnostic technologies to improve the early diagnosis, surveillance, margin assessment and management of our oral cancer patients.

Raman spectroscopy is a point-wise label-free optical technique that offers a comprehensive optical fingerprint of a myriad of inter- and intracellular building blocks (i.e., proteins, lipids and DNA). Because cellular constituents undergo biomolecular changes with disease onset and progression, the Raman technique can facilitate real-time "optical biopsy" with high biochemical specificity. Our previous work has shown that this technology can be applied in vivo in the oral cavity, head & neck, esophagus, stomach and colon with accuracies in the range of 70-85%. Conventional Raman spectroscopy is however limited to provide information about tissue composition but does not offer insight into the tissue structure such as connective tissue organisation. It is well known that tissue structure (i.e., connective tissue) is disrupted during carcinogenesis. We hypothesize that by taking advantage of this complementary information using polarized Raman spectroscopy this could provide a new contrast mechanism of cancer and potentially in the long term lead to more accurate diagnosis.

Here, we demonstrate a novel polarized Raman approach for the biostructural analysis of changes that occur in between normal and cancerous human oral tissue. By tightly focusing the laser light on the tissue surface, we are able to preserve polarized Raman signals from bulk cancer tissue, allowing us to extract both biochemical and structural information from human tissue.

Material and Methods

We investigated the capability of the polarized Raman approach to detect biostructural changes in bulk oral cancerous tissue. Bulk human oral tissues (n=2) were procured from the Guy's and St Thomas Thrust Biobank after grant of ethics. Tissues were fixed in paraformaldehyde (PFA) and washed in saline prior to Raman analysis. The polarized Raman needle system has been described in detail elsewhere. The distal lens was placed above the tissue oriented normal to the surface and sets of polarized Raman spectra (perpendicular and parallel) were measured.

Results

Figure 7A:
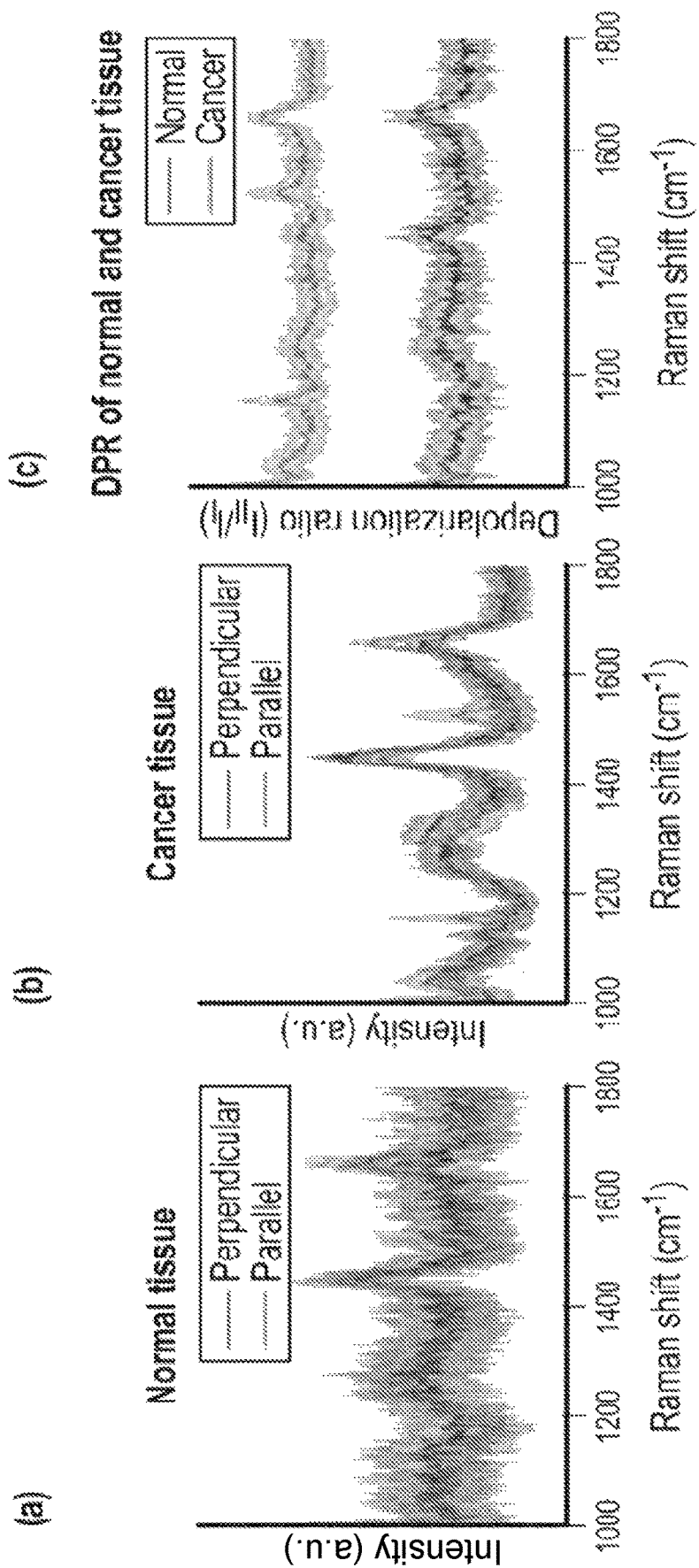
FIG. 7A shows how methods and systems described herein may be applied to identifying cancerous tissue. Polarisation difference (Parallel-Perpendicular) spectra±1 SD for the (a) normal tissue zone (n=20 spectra) and (b) cancer tissue (n=20) (c) Depolarisation ratio of normal and cancer tissue, showing distinct peaks associated with human tissue.
Figure 7B:
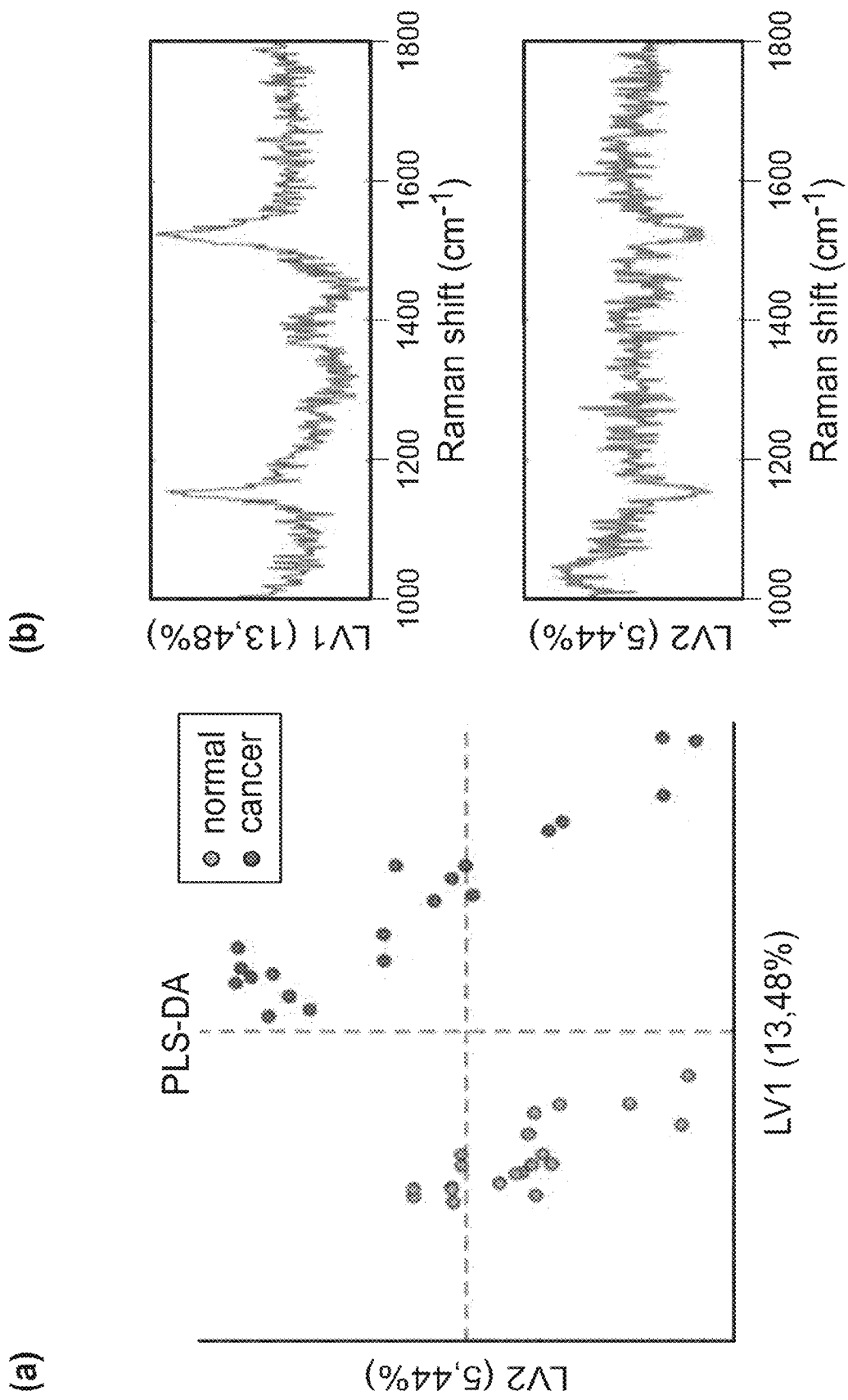
FIG. 7B shows (a) PLS-DA score plot showing the separation of normal and cancer tissue (b) PLS-DA latent variable (LV) loading of the depolarisation ratio Raman spectra showing distinct peaks associated with human tissue.

FIG. 7.1*a-b* shows polarized Raman spectra of the normal and cancerous tissue area (mean±1 standard deviation (SD)). A total of 40 spectra measured using a 10 s acquisition time to obtain a very high signal-to noise ratio (SNR), that is; cancer (n=20 spectra) and normal margin (n=20 spectra). Intense Raman peaks were observed for both polarizations at 1335, 1446, and 1660 cm$^{-1}$ (FIG. 7.1). The peaks tentatively correspond to DNA, lipids and proteins respectively showing biochemical information can be obtained. More importantly for this work, we found consistent differences between the parallel and perpendicular polarization in both normal and cancer tissue, in particular at 1446, 1660, 1154 and 1520 cm$^{-1}$. We therefore calculated the depolarization Raman spectra (DPR) (parallel/(perpendicular+n)); here n is an arbitrary number, used to avoid near infinite values in the spectra. The size of n is arbitrary and does not affect the comparison and analysis of the zones (see FIG. 7.1*c*). The differences in DPR suggests that the organisation (tissue structure) changes significantly for cancerous tissue compared to normal tissues. To take advantage of the full range of polarized Raman peaks associated with tissue structure (rather than tissue biochemistry alone), we employed partial least squares discriminant analysis (PLS-DA) on the DPR spectra. We utilised cross-validation (leave one measurement out) to determine model complexity of two latent variables (LVs). FIG. 7.2*a* shows a scatter plot of the PLS scores for the cancer tissue zones. We found clear discrimination between the normal and cancer tissue (100% accuracy using a linear discriminator). FIG. 7.2b shows the loading for the two LVs from the PLS-DA. LV1 accounted for a total of 13.41% of the variance in the X-Block and 83.75% in the Y-Block. LV2 accounted for a total of 5.17% of the variance in the X-Block and 13.27% in the Y-Block. Several peaks were prominent across the two LVs suggesting that polarized Raman spectroscopy offers novel insights into the tissue structure (i.e., connective tissue) and that the loss of tissue architecture alone can be used for very accurate diagnostics.

Summary

We measured polarized Raman spectra (parallel and perpendicular) of oral cancer and normal tissues. Our results showed that based on features of the tissue structure (i.e., DPR) (rather than only tissue composition) we could perform diagnosis of cancer providing a new contrast mechanism.

The Computer System

Figure 6:
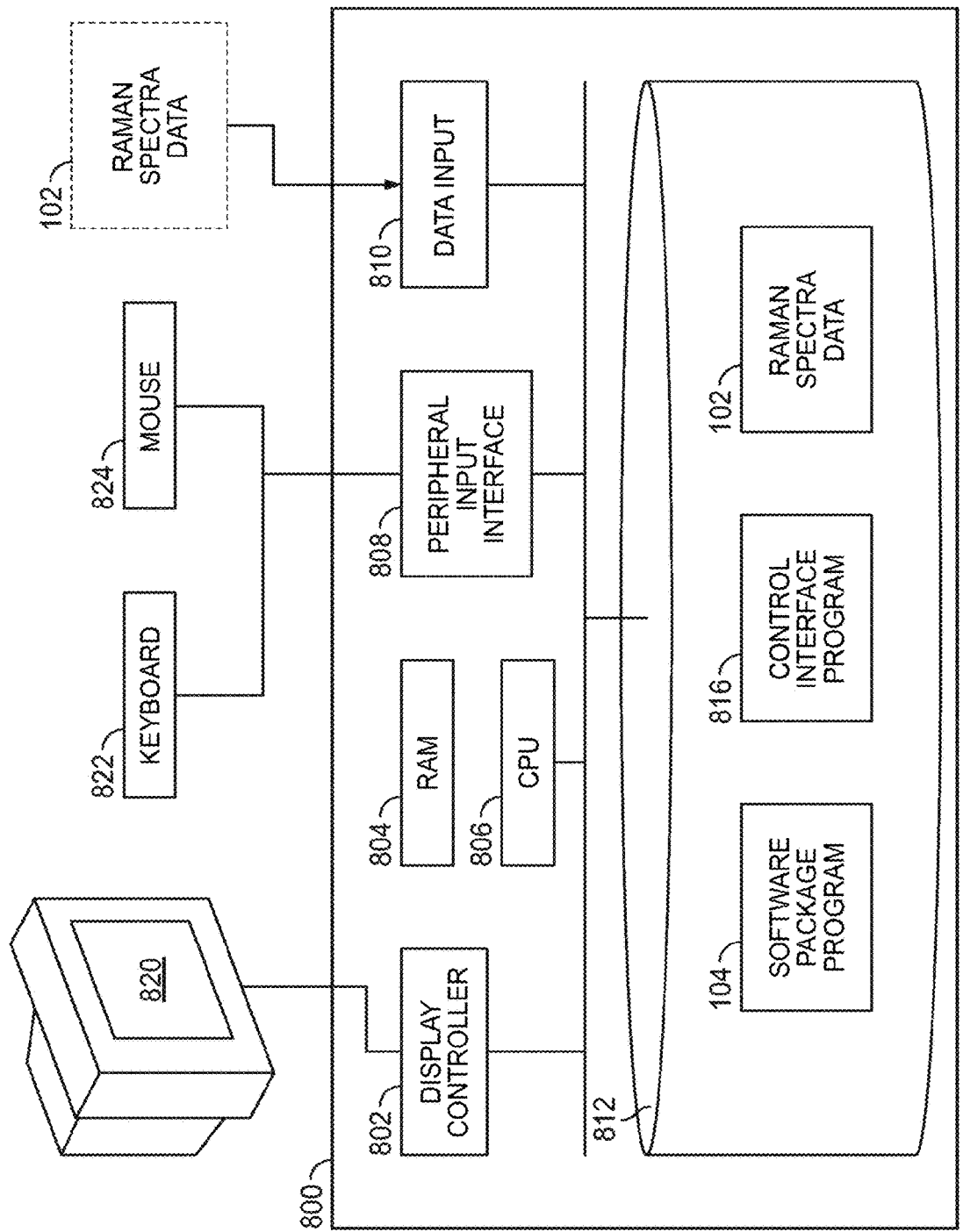
FIG. 6 is a block diagram of a system according to an embodiment of the present invention.

An example of a computer system used to perform embodiments of the present invention is shown in FIG. 6.

FIG. 6 is a block diagram illustrating an arrangement of a system according to an embodiment of the present invention. Some embodiments of the present invention are designed to run on general purpose desktop or laptop computers. Therefore, according to an embodiment, a computing apparatus 800 is provided having a central processing unit (CPU) 806, and random access memory (RAM) 804 into which data, program instructions, and the like can be stored and accessed by the CPU. The apparatus 800 is provided with a display screen 820, and input peripherals in the form of a keyboard 822, and mouse 824. Keyboard 822, and mouse 824 communicate with the apparatus 800 via a peripheral input interface 808. Similarly, a display controller 802 is provided to control display 820, so as to cause it to display images under the control of CPU 806. Raman spectra data 102, can be input into the apparatus and stored via data input 810. In this respect, apparatus 800 comprises a computer readable storage medium 812, such as a hard disk drive, writable CD or DVD drive, zip drive, solid state drive, USB drive or the like, upon which Raman spectra data 102 can be stored. Alternatively, the Raman spectra data 102 could be stored on a web-based platform, e.g. a database, and accessed via an appropriate network. Computer readable storage medium 812 also stores various programs, which when executed by the CPU 806 cause the apparatus 800 to operate in accordance with some embodiments of the present invention.

In particular, a control interface program 816 is provided, which when executed by the CPU 806 provides overall control of the computing apparatus, and in particular provides a graphical interface on the display 820, and accepts user inputs using the keyboard 822 and mouse 824 by the peripheral interface 808. The control interface program 816 also calls, when necessary, other programs to perform specific processing actions when required. For example, a software package program 104 may be provided which is able to operate on Raman spectra data 102 indicated by the control interface program 816. The operations of the program 104 are described in more detail above. Software package program 104 is described above. Program 104 may read out one or more, e.g. two, Raman spectra simultaneously and performs pre-processing, and multivariate analysis on the Raman spectra (perpendicular+parallel) and analysis of the perpendicular and parallel polarized Raman spectra for collagen analysis.

The detailed operation of the computing apparatus 800 will now be described. Firstly, the user launches the control interface program 816. The control interface program 816 is loaded into RAM 804 and is executed by the CPU 806. The user then launches a program 104. The program 104 acts on the input data 102 as described above.

Various modifications whether by way of addition, deletion, or substitution of features may be made to above described embodiment to provide further embodiments, any and all of which are intended to be encompassed by the appended claims.

The invention claimed is:

1. A system for obtaining structural information relating to tissue, the system comprising:
   (i) a probe configured to direct polarized light to the tissue and collect Raman scattering;
   (ii) a lens mounted at a distal tip of the probe, wherein the lens is configured to focus the polarized light onto the tissue such that the polarized light is reflected from the tissue, producing Raman scattering which is collected by the probe;
   (iii) a beam splitter configured to split the Raman scattering into two polarized components;
   (iv) respective optical waveguides to guide the two polarized components; and
   (v) a spectrometer configured to receive the two polarized components via the respect optical waveguides and to simultaneously and separately image the two polarized components to produce two Raman spectra.

2. A system according to claim 1, the system further comprising:
   a processor; and
   a memory including computer program code,
   the memory and the computer program code configured to, with the processor, cause the processor to process and analyze the two produced Raman spectra to obtain structural information relating to the tissue.

3. A system according to claim 1, wherein the system simultaneously obtains biochemical and structural information relating to the tissue.

4. A system according to claim 3, wherein the processing and analyzing of the two produced Raman spectra obtains biochemical information and structural information relating to the tissue.

5. A system according to claim 1, wherein a first polarized component of the two polarized components is parallel to polarization of the polarized light, and a second polarized component of the two polarized components is perpendicular to polarization of the polarized light; and wherein the structural information is obtained by calculating a difference between the first and second polarized components and/or a ratio between the first and second polarized components and/or an anisotropy between the first and second components.

6. A system according to claim 1, wherein the structural information comprises a measure of structural alignment in the tissue.

7. A system according to claim 4, wherein the biochemical information is obtained by quantifying relative contributions of extracellular matrix constituents of the produced Raman spectra.

8. A system according to claim 4, wherein the biochemical information is obtained by calculating a sum of the first and second polarized components.

9. A system according to claim 7, wherein the quantifying of the relative contributions of extracellular matrix constituents of the produced Raman spectra comprises using regression coefficients derived from multivariate least-squares-regression analysis; and wherein the least-squares-regression analysis comprises comparing the produced Raman spectra to reference Raman spectra of the extracellular matrix constituents.

10. A system according to claim 7, wherein the extracellular matrix constituents comprise one or more of glycosaminoglycan, collagen, and/or water.

11. A system according to claim 1, wherein the biochemical and/or structural information is obtained in real-time; and/or wherein the tissue is a musculoskeletal connective tissue.

12. A system according to claim 1, wherein the biochemical and/or structural information is used to identify tissue abnormalities; and optionally wherein the tissue abnormalities are cancerous.

13. A system according to claim 1, wherein the biochemical and/or structural information is used to diagnose and/or monitor connective tissue degenerative disorders, such as osteoarthritis and/or degenerative disc disease; and/or wherein the tissue is engineered tissue and the biochemical and/or structural information is used to measure growth and/or regeneration of the engineered tissue; and/or wherein a source of the light or polarized light is a laser.

14. A system according to claim 1, wherein the probe comprises a needle, and the lens is mounted at a tip of the needle and configured to be in contact with the tissue; and/or wherein the lens is a sapphire ball lens.

15. A system according to claim 1, wherein the probe comprises a long distance focusing Raman probe; and wherein the method further comprises directing the polarized light to the tissue through a Raman transparent window in a tissue plate containing the tissue.

16. A method for obtaining structural information relating to tissue, the method comprising:
    (i) directing polarized light to the tissue using a probe;
    (ii) focusing the polarized light onto the tissue using a lens, wherein the lens is mounted at a distal tip of the probe and focuses the polarized light onto the tissue such that the polarized light is reflected from the tissue, producing Raman scattering;
    (iii) collecting the Raman scattering using the probe;
    (iv) splitting the Raman scattering into two polarized components using a beam splitter;
    (v) guiding the two polarized components via respective optical waveguides to a spectrometer;
    (vi) simultaneously and separately imaging the two polarized components to produce two Raman spectra; and
    (vii) processing and analyzing the two produced Raman spectra using a computer program to obtain structural information relating to the tissue,
    wherein the method simultaneously obtains biochemical and structural information relating to the tissue.

17. A system for simultaneously obtaining biochemical and structural information relating to tissue, the system comprising:
    (i) a probe configured to direct polarized light to the tissue and collect Raman scattering;
    (ii) a lens mounted at a distal tip of the probe, wherein the lens is configured to focus the polarized light onto the tissue such that the polarized light is reflected from the tissue, producing Raman scattering which is collected by the probe;
    (iii) a beam splitter configured to split the Raman scattering into two polarized components;
    (iv) respective optical waveguides to guide the two polarized components; and
    (v) a spectrometer configured to receive the two polarized components via the respective optical waveguides and to simultaneously and separately image the two polarized components to produce two Raman spectra;
    (vi) a processor; and
    (vii) a memory including computer program code, the memory and the computer program code configured to, with the processor, cause the processor to process and analyze the two produced Raman spectra to obtain biochemical information and structural information relating to the tissue.

18. A method for simultaneously obtaining biochemical and structural information relating to tissue, the method comprising:
    i) directing polarized light to the tissue using a probe;
    ii) focusing the polarized light onto the tissue using a lens, wherein the lens is mounted at a distal tip of the probe and focuses the polarized light onto the tissue such that the polarized light is reflected from the tissue, producing Raman scattering;
    iii) collecting the Raman scattering using the probe;
    iv) splitting the Raman scattering into two polarized components using a beam splitter;
    v) guiding the two polarized components via respective optical waveguides to a spectrometer;
    vi) simultaneously and separately imaging the two polarized components to produce two Raman spectra; and
    vii) processing and analyzing the two produced Raman spectra using a computer program to obtain biochemical information and structural information relating to the tissue.

* * * * *